(12) United States Patent
Dagdeviren et al.

(10) Patent No.: US 10,842,388 B2
(45) Date of Patent: Nov. 24, 2020

(54) SYSTEMS, DEVICES, AND METHODS FOR CONTACT MEASUREMENT AND MODULATION OF MATERIAL PROPERTIES

(71) Applicants: Arizona Board of Regents on Behalf of the University of Arizona, Tucson, AZ (US); BOARD OF TRUSTEES OF UNIVERSITY OF ILLINOIS, Urbana, IL (US)

(72) Inventors: Canan Dagdeviren, Cambridge, MA (US); John A. Rogers, Urbana, IL (US); Marvin J. Slepian, Tucson, AZ (US)

( * ) Notice: Subject to any disclaimer, the term of this patent is extended or adjusted under 35 U.S.C. 154(b) by 173 days.

(21) Appl. No.: 15/567,239

(22) PCT Filed: Apr. 17, 2016

(86) PCT No.: PCT/US2016/028017
§ 371 (c)(1),
(2) Date: Oct. 17, 2017

(87) PCT Pub. No.: WO2016/168789
PCT Pub. Date: Oct. 20, 2016

(65) Prior Publication Data
US 2018/0103852 A1 Apr. 19, 2018

Related U.S. Application Data

(60) Provisional application No. 62/148,946, filed on Apr. 17, 2015, provisional application No. 62/157,710, filed on May 6, 2015.

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/0051* (2013.01); *A61B 5/442* (2013.01);
(Continued)

(58) Field of Classification Search
CPC ........ A61B 2562/02; A61B 2562/0261; A61B 2562/12; A61B 5/442; A61N 1/0492; A61N 1/0504
See application file for complete search history.

(56) References Cited

U.S. PATENT DOCUMENTS 7,533,571 B2  5/2009  Ariav et al.
8,552,299 B2  10/2013 Rogers et al.
(Continued)

FOREIGN PATENT DOCUMENTS

WO   2010135516      10/2010
WO   2015051085 A1   4/2015

OTHER PUBLICATIONS

International Search Report for PCT/US2016/028017 datd Jul. 18, 2016.
(Continued)

*Primary Examiner* — Christine H Matthews
(74) *Attorney, Agent, or Firm* — Thomas|Horstemeyer, LLP

(57) ABSTRACT

Materials and devices are provided for the sensing and manipulation of biomechanical and physiochemical properties of tissues or tissue surfaces. Examples of use include soft tissues such as skin or adipose tissues or more dense tissues such as muscle or heart or dense tissues such as bone. The materials and devices provide for in vivo measurements of biomechanical properties at the tissue surface, e.g. near surface regions of the epidermis or dermis or underlying structures. The devices can be non-invasive and/or non-destructive to the material and, especially for the biomate-
(Continued)

rials, can be biocompatible and/or biodegradable. The materials and devices can use ultrathin, stretchable networks of mechanical actuators and sensors constructed with nanoribbons of piezoelectric materials.

21 Claims, 34 Drawing Sheets

(51) Int. Cl.
*G16H 20/17* (2018.01)
*A61N 1/04* (2006.01)
*A61N 1/05* (2006.01)
*B81C 1/00* (2006.01)

(52) U.S. Cl.
CPC ............ *A61B 5/444* (2013.01); *A61N 1/0492* (2013.01); *A61N 1/0504* (2013.01); *B81C 1/00031* (2013.01); *G16H 20/17* (2018.01); *A61B 2562/02* (2013.01); *A61B 2562/0261* (2013.01); *A61B 2562/12* (2013.01)

(56) References Cited

U.S. PATENT DOCUMENTS

| | | |
|---|---|---|
| 2012/0226130 A1 | 9/2012 | De Graff et al. |
| 2013/0041235 A1 | 2/2013 | Rogers et al. |
| 2014/0374872 A1 | 12/2014 | Rogers et al. |

OTHER PUBLICATIONS

X. Liang, et al., "Biomechanical Properties of In Vivo Human Skin From Dynamic Optical Coherence Elastography", NIH Public Access IEEE Trans Biomed Eng. Apr. 2010 ; 57(4): 953-959.

C. Dagdeviren, et al., "Conformable amplified lead zirconate titanate sensors with enhanced piezoelectric response for cutaneous pressure monitoring", Nature Communications, Aug. 1-10, 2014.

C. Dagdeviren, et al., "Conformal piezoelectric energy harvesting and storage from motions of the heart, lung, and diaphragm", CrossMark, 2014, vol. 111, 5, 1927-1932.

$V_{act}$

SYSTEMS, DEVICES, AND METHODS FOR CONTACT MEASUREMENT AND MODULATION OF MATERIAL PROPERTIES

CROSS-REFERENCE TO RELATED APPLICATIONS

This application is the 35 U.S.C. § 371 national stage application of PCT Application No. PCT/US2016/028017, filed Apr. 17, 2016, which claims priority to, and the benefit of, U.S. provisional application entitled "SYSTEMS, DEVICES, AND METHODS FOR CONTACT MEASUREMENT AND MODULATION OF MATERIAL PROPERTIES" having Ser. No. 62/148,946, filed Apr. 17, 2015 and U.S. provisional application entitled "SYSTEMS, DEVICES, AND METHODS FOR CONTACT MEASUREMENT AND MODULATION OF MATERIAL PROPERTIES" having Ser. No. 62/157,710, filed May 6, 2015, all of which are hereby incorporated by reference in their entireties.

STATEMENT REGARDING FEDERALLY SPONSORED RESEARCH OR DEVELOPMENT

This invention was made with government support under award # DE-FG02-07ER46471 awarded by the U.S. Department of Energy. The government has certain rights in the invention.

FIELD OF THE DISCLOSURE

This disclosure is generally in the field of materials, devices, and methods for sensing and manipulation of material properties, in particular soft tissue materials.

BACKGROUND

Non-invasive determination of material properties, in particular of soft materials, remains a challenge. This is particularly relevant in the area of biomaterials such as soft tissues. Human skin is the largest organ of the body; its epidermal and dermal layers serving as the external envelope for containment of all viscera, fluids and tissue constituents, as a protective barrier to environmental hazards, pathogens and toxins, as a sensory interface for transduction of physical stimuli, e.g. pressure and cold, and as a modulating membrane for control of water, electrolytes and other biochemical mediators. Despite these essential roles, there is much that is unknown about the basic physical properties of skin, including details related to its responses to mechanical loads. Precise measurements of the elastic modulus of skin under various conditions can facilitate the assessment of a variety of pathophysiologic conditions, may predict reactions to exogenous substances and environmental factors, can help in gauge the effectiveness of cosmetic products and further establish mechanisms associated with growth, repair and aging. Mechanical properties specifically are centrally important in the diagnosis and treatment of disorders such as scleroderma, Ehlers-Danlos syndrome, psoriasis, eczema, melanoma, and other cutaneous pathologies, all of which involve changes in the elastic modulus of the skin. Further, the outermost layer of the skin, the stratum corneum (SC), is important in mechano-protection, somato-sensory reception and thermal regulation. Understanding the mechanical properties of the SC alone is relevant to the design of percutaneous penetration strategies and optimization of topical therapy to treat damaged skin. Presently, methods for in vivo measurement of the elasticity and physical durability of skin involve pressure-based suction, torsion, traction, nanoindentation and ultrasound elastography. Although these techniques can provide important insights into the mechanics of skin, the measurements typically involve large uncertainties and the associated tools are not amenable to wearable device architectures for continuous monitoring or to non-invasive use on sensitive or highly curved regions of the skin.

SUMMARY OF THE DISCLOSURE

Materials and devices are provided for the sensing and manipulation of materials such as, e.g., the determination of biomechanical and physiochemical properties of tissues or tissue surfaces. Examples of use include soft tissues such as skin or adipose tissues or more dense tissues such as muscle or heart or dense tissues such as bone. The materials and devices provide for in vivo measurements of biomechanical properties at the tissue surface, e.g. near surface regions of the epidermis or dermis or underlying structures. The devices can be non-invasive and/or non-destructive to the material and, especially for the biomaterials, can be biocompatible and/or biodegradable. The materials and devices can use ultrathin, stretchable networks of mechanical actuators and sensors constructed with nanoribbons of lead zirconate titanate (PZT). In some embodiments, soft, reversible lamination onto the skin enables rapid, quantitative assessment of the viscoelastic moduli, with ability for spatial mapping. The materials and devices can provide accurate and reproducible measurements of both the storage and loss moduli for a variety of substrates and conditions. The disclosure discloses methods of making the devices and methods of using the devices for sensing and manipulation of material properties, including soft tissue such as the skin.

In various aspects, devices for contact sensing of a material property are provided. The devices can contain actuating elements and sensing elements mechanically coupled to the actuating elements on a thin elastomeric substrate. The sensing element can be substantially aligned with the actuating element, e.g. the device can contain a plurality of the actuating elements and a plurality of the sensing elements and each of the sensing elements is mechanically coupled to one or more of the actuating elements. The sensing element can be substantially aligned with the actuating element, e.g. wherein the sensing element and the actuating element are separated by less than 1.0 mm. The devices can be stretchable and/or conformable to a material surface.

The devices can contain pairs of electrodes, e.g. for addressing each of the sensing and actuating elements. In various aspects, a first pair of electrodes can be in electrical contact with the actuating element and a second pair of electrodes in electrical contact with the sensing element. The interconnects can be stretchable conductive interconnects, e.g. serpentine metal interconnects.

The actuating and/or sensing elements can be made from a piezoelectric material. Examples of the piezoelectric material can be selected from the group consisting of Berlinite ($AlPO_4$), Sucrose (table sugar), Quartz, Rochelle salt, Topaz, Tourmaline-group minerals, Gallium orthophosphate ($GaPO_4$), Langasite ($La_3Ga_5SiO_{14}$), Barium titanate ($BaTiO_3$), Lead titanate ($PbTiO_3$), Lead zirconate titanate ($Pb[Zr_xTi_{1-x}]O_3$, $0<x<1$) (commonly referred to as PZT), Potassium niobate ($KNbO_3$), Lithium niobate ($LiNbO_3$), Lithium tantalate ($LiTaO_3$), Sodium tungstate ($Na_2WO_3$), Zinc oxide (ZnO), $Ba_2NaNb_5O_5$, $Pb_2KNb_5O_{15}$, Sodium potassium niobate ((K,Na)Nb03) (also known as NKN), Bismuth ferrite (BiFe03), Sodium niobate (NaNb03), Bismuth titanate (BUT^On), Sodium bismuth titanate (Nao.sBio.5Ti03), polyvinylidene fluoride (PVDF), poly [(vinylidenefluoride-co-trifluoroethylene] [P(VDF-TrFE)3, and combinations thereof. The device can be constructed such that the neutral mechanical plane passes through the piezoelectric material. The piezoelectric material can have a thickness of 100 nm to 1,000 nm.

The device can have a plurality of the actuating elements and a plurality of the sensing elements and each of the sensing elements can be mechanically coupled to one or more of the actuating elements. For example, in various aspects the sensing elements are interdigitated within the actuating elements.

The devices can be used to sense a variety of material properties. In various aspects, the sensing element has an output that is linearly proportional to the material property over a range of values. The output of the sensing element can be an output voltage, an output current, an output resistance, or a combination thereof. The material property can include the modulus of the material over a range of values from 1 kPa to 5,000 kPa. In various aspects, the sensing element is capable of producing a detectable change in the output in response to a change of at least 1% in the material property. In various aspects, the output voltage from the sensing element is independent of a surface roughness of the material, the surface roughness extending over a range of roughness from 0.1 to 100 μm.

Various methods of making the devices are also provide. The methods can include forming a top electrode by photolithography with an electrode material selected from the group consisting of Ag, Al, Au, Co, Cr, Cu, Fe, Mo, Nb, Ni, W, Zn, Zr, Ti, Pt, and combinations thereof; deposition, patterning, or etching of a piezolelectric layer with a piezoelectric material selected from the group consisting of Berlinite (AlPO4), Sucrose (table sugar), Quartz, Rochelle salt, Topaz, Tourmaline-group minerals, Gallium orthophosphate (GaP04), Langasite (La3Ga5SiOi4), Barium titanate (BaTi03), Lead titanate (PbTi03), Lead zirconate titanate (Pb[ZrxTii^]03, 0<x<l) (commonly referred to as PZT), Potassium niobate (KNb03), Lithium niobate (LiNb03), Lithium tantalate (LiTa03), Sodium tungstate (Na2W03), Zinc oxide (ZnO), Ba2NaNb505, Pb2KNb5Oi5, Sodium potassium niobate ((K,Na)Nb03) (also known as NKN), Bismuth ferrite (BiFe03), Sodium niobate (NaNb03), Bismuth titanate (BUT^On), Sodium bismuth titanate (Nao.sBio.5Ti03), polyvinylidene fluoride (PVDF), poly [(vinylidenefluoride-co-trifluoroethylene] [P(VDF-TrFE)3, and combinations thereof; and deposition, patterning, or etching of a bottom electrode with an electrode material selected from the group consisting of Ag, Al, Au, Co, Cr, Cu, Fe, Mo, Nb, Ni, W, Zn, Zr, Ti, Pt, and combinations thereof. The methods can include transferring the actuating element and the sensing element to a thin elastomeric substrate. The substrate can be silicon or a silicon containing polymer. The methods can include encapsulating one or both of the actuating element and the sensing element with a barrier layer such as polyimide.

Methods of contact sensing of material properties using the devices are also provided. The methods can include applying the device to a surface of a material; activating one or more actuation element to manipulate the material; and receiving an output from the sensing element in response to the manipulation of the material The device can bind to the material surface by van der Waals interactions. The device can be applied to the material surface in a fluent or semi-fluent state and then stimulated to render it non-fluent and conformed to the material surface. The device can be applied in vivo. The methods can include removing the device and reapplying the device to the same surface or to a second material surface.

The methods can be used to measure a variety of material properties. In various aspects, the property is selected from the group consisting of pH, surface tension, electrical conductivity, permittivity, hardness, flexural modulus, flexural strength, plasticity, shear modulus, shear strength, Young's modulus, surface roughness, ductility, Poisson's ratio, resilience, fracture toughness, compressive strength, creep, stress relaxation, coefficient of friction, hysteresis, temperature, thermal conductivity, acoustic absorption or reflection, and combinations thereof. In various aspects, the material is the skin and the material property is indicative of a physiological state selected from the group consisting of a hydration level of the skin, a healing progress of the skin, and a disease state of the skin. The physiological state can be the disease state of the skin and the disease state is selected from the group consisting of a fibrosis level and a presence of a lesion in or below the skin. In some aspects, the material is the skin and the material property is indicative of an effector response to an exogenous agent. For example, the exogenous agent can be selected from the group consisting of heat, a cooling applied drug, radiation, physical manipulation, and ultrasound. The material can be an organ and the material property is indicative of a physiological state selected from the group consisting of a hydration level of the organ, a healing progress of the organ, and a disease state of the organ. For example, the organ can be selected from the group consisting of a heart, a liver, a lung, and an intestine. In various aspects, the physiological state is the disease state of the organ and the disease state is selected from the group consisting of a fibrosis level and a presence of a lesion in or below the surface of the organ.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 1A depicts a cross sectional illustration of the edge of a single PZT nanoribbon in a capacitor structure on a $SiO_2$/Si wafer. FIG. 1B depicts a cross sectional illustration of the same region an intermediate state of undercut etching with dilute HF solution. FIG. 1C depicts the process of retrieving the PZT sensor and actuator arrays with a PDMS stamp, leaving them adhered to the surface of the stamp. FIG. 1D depicts the result after transfer printing onto a temporary substrate. FIG. 1E depicts the completed CMS system on temporary substrate, at a reduced magnification view. FIG. 1F depicts a process of retrieving the system with a PDMS stamp. FIG. 1G depicts the result after transfer printing onto a thin silicone substrate.

FIG. 2A is an optical microscope image of a photoresist patterned on gold (Au) to define electrodes for capacitor structures. FIG. 2P are optical microscope images of a pattern of the arrays with serpentine interconnections after etching PI.

FIG. 5A depicts modulus values for normal and lesion skin on the back region or a male subject diagnosed with fibrous histocytoma. FIG. 5B depicts modulus values for normal and lesion skin on the temple region of a male subject diagnosed with seborrheic ketatosis, irritated and inflamed. FIG. 5C depicts modulus values for normal and lesion skin on the back region of a female subject diagnosed with basal cell carcinoma. FIG. 5D depicts modulus values for normal and lesion skin on the armpit region of a female subject diagnosed with compound nevus. FIG. 5E depicts p modulus values for normal and lesion skin on the shoulder region of a male patient diagnosed with basal cell carcinoma.

FIG. 6A depicts modulus values for normal and lesion skin on the temple region of a patient diagnosed with actinic keratosis. FIG. 6B depicts modulus values for normal and lesion skin on the hand region of a female patient diagnosed with squamous cell carcinoma. FIG. 6C depicts modulus values for normal and lesion skin on the arm region of a female patient diagnosed with seborrheic keratosis, irritated. FIG. 6D depicts modulus values for normal and lesion skin on the abdomen region of a male patient diagnosed with irritated hemangioma. FIG. 6E depicts modulus values for normal and lesion skin on the breast region of a female patient diagnosed with compound nevus.

FIG. 7A depicts modulus values for normal and lesion skin on the cheek region of a male patient diagnosed with seborrheic keratosis, irritated and inflamed. FIG. 7B depicts modulus values for normal and lesion skin on the abdomen region of a female patient diagnosed with a fibroepithelial polyp. FIG. 7C depicts modulus values for normal and lesion skin on the arm region of a male patient diagnosed with superficial perivascular and interface lymphocytic dermatitis. FIG. 7D depicts modulus values for normal and lesion skin on the leg region of a female patient diagnosed with a severely atypical compound melanocytic proliferation.

FIG. 8A is a graph of sensor voltage as a function of actuator voltage before (base) and after 1000 cycles of stretching to 30% tensile strain. FIG. 8B is a graph of sensor voltage as a function of actuator voltage before application onto the skin (base) and after 500 cycles of application and removal.

FIG. 9A is an optical micrograph of serpentine interconnections and arrays of sensors and actuators at 0% strain. FIG. 9B is an optical micrograph of serpentine interconnections and arrays of sensors and actuators at 2% strain. FIG. 9C is an optical micrograph of serpentine interconnections and arrays of sensors and actuators at 5% strain. FIG. 9D is an optical micrograph of serpentine interconnections and arrays of sensors and actuators at 10% strain. FIG. 9E is an optical micrograph of serpentine interconnections and arrays of sensors and actuators at 15% strain. FIG. 9F is an optical micrograph of serpentine interconnections and arrays of sensors and actuators at 30% strain.

FIG. 10A illustrates the initial state of the sensors and actuators at the interface between the supporting substrate (top) and the sample under test (bottom; PDMS) FIG. 10B is a schematic distribution of pressure induced by expansion of the leftmost actuator element. FIG. 10C depicts expansion of the actuator after applying a voltage.

FIG. 12A is the voltage output of sensor #1, i.e., the sensor adjacent to the active actuator, as a function of actuator voltage, measured on nine different PDMS substrates with known moduli, separately evaluated by quasi-static dynamical mechanical analysis. FIG. 12B is the output voltage from sensor #1 as a function of modulus of the substrate under test, for four actuator voltages ($V_{act}$). FIG. 12C is the output voltages for each of the different sensors in the array (i.e. sensor #1, #2, etc) measured during use with $E_{PDMS}$=1800 kPa at three different frequencies, all at an actuation voltage of 5 V. FIG. 12D is the output voltages for each of the different sensors in the array (i.e. sensor #1, #2, etc) measured during use with $E_{PDMS}$=30 kPa at three different frequencies, all at an actuation voltage of 5 V. FIG. 12E is a graph of Tan δ as a function of actuation frequency.

FIG. 13A is the sensor voltage as a function of distance to the actuator for samples with moduli of 33 kPa, 200 kPa, 930 kPa, respectively. FIG. 13B is the sensor voltage as a function of distance to the actuator for samples with moduli of 67 kPa, 235 kPa, 1385 kPa, respectively. FIG. 13C is the sensor voltage as a function of distance to the actuator for samples with moduli of 88 kPa, 366 kPa, 1764 kPa, respectively.

FIG. 16A depicts sensor voltage and CMS modulus values at an actuation voltage and frequency of 5 V and 1 kHz, respectively, for ex vivo female (left graph) and male (right graph) abdominal skin for both young and old cases, at different times following application of 1% AMPS. FIG. 16B depicts sensor voltage and CMS modulus values for in vivo female skin at different times following application of 1% AMPS; and FIG. 16C depicts sensor voltage and CMS modulus values for in vivo male skin at different times following application of 1% AMPS. The measurements at 0 min correspond to unmodified skin (baseline), before application of AMPS. Measurements were performed on Young (Y) and Old (O) skin at three locations: Abdomen, Back, and Forearm.

FIG. 17A is a graph of the modulus values for young and old female skin before (0 min) and at various times after application of 3% glycerin solution. FIG. 17B is a graph of the modulus values for young and old male skin before (0 min) and at various times after application of 3% glycerin solution. FIG. 17C is a graph of the modulus values for young and old female skin before (0 min) and at various times after application of 3% urea solution. FIG. 17D is a graph of the modulus values for young and old male skin before (0 min) and at various times after application of 3% urea solution.

FIG. 18A is a graph of modulus values for young female and male skin before (0 min) and at various times after application of 1% AMPS. FIG. 18B is a graph of modulus values for young female and male skin before (0 min) and at various times after application of 3% glycerin solution. FIG. 18C is a graph of modulus values for young female and male skin before (0 min) and at various times after application of 3% urea solution. FIG. 18D is a graph of modulus values for old female and male skin before (0 min) and at various times after application of 1% AMPS. FIG. 18E is a graph of modulus values for old female and male skin before (0 min) and at various times after application of 3% glycerin solution. FIG. 18F is a graph of modulus values for old female and male skin before (0 min) and at various times after application of 3% urea solution.

FIG. 19A is a graph of the modulus values before (0 min) and at various times after application of (from left to right) 1% AMPS, 3% glycerin, and 3% urea solutions for young female skin. FIG. 19B is a graph of the modulus values before (0 min) and at various times after application of (from left to right) 1% AMPS, 3% glycerin, and 3% urea solutions for old female skin. FIG. 19C is a graph of the modulus values before (0 min) and at various times after application of (from left to right) 1% AMPS, 3% glycerin, and 3% urea solutions for young male skin. FIG. 19D is a graph of the modulus values before (0 min) and at various times after application of (from left to right) 1% AMPS, 3% glycerin, and 3% urea solutions for old male skin.

FIG. 20A is a graph of the modulus of young and old female abdominal skin before and after application of 1% AMPS, 3% Glycerin and 3% Urea solutions. FIG. 20B is a graph of the modulus of young and old male abdominal skin before and after application of 1% AMPS, 3% Glycerin and 3% Urea solutions.

FIG. 21A is a graph of CMS modulus values at an actuation voltage and frequency of 5 V and 1 kHz, respectively, for data collected on skin in the breast region under normal conditions and with lesions. FIG. 21B is a graph of CMS modulus values at an actuation voltage and frequency of 5 V and 1 kHz, respectively, for data collected on skin in the leg region under normal conditions and with lesions. FIG. 21C is a graph of CMS modulus values at an actuation voltage and frequency of 5 V and 1 kHz, respectively, for data collected on skin in the near nose region under normal conditions and with lesions. FIG. 21D is a graph of CMS modulus values at an actuation voltage and frequency of 5 V and 1 kHz, respectively, for data collected on skin in the forehead region under normal conditions and with lesions. FIG. 21E is a graph of CMS modulus values at an actuation voltage and frequency of 5 V and 1 kHz, respectively, for data collected on skin in the near eye region under normal conditions and with lesions. FIG. 21F is a graph of CMS modulus values at an actuation voltage and frequency of 5 V and 1 kHz, respectively, for data collected on skin in the neck region under normal conditions and with lesions.

FIG. 22A is a graph of the modulus values for young female skin on the abdomen, cheek, palm, back, arm, forearm, ear and forehead. FIG. 22B is a graph of the modulus values for old female skin on the abdomen, cheek, palm, back, arm, forearm, ear and forehead. FIG. 22C is a graph of the modulus values for young male skin on the abdomen, cheek, palm, back, arm, forearm, ear and forehead. FIG. 22D is a graph of the modulus values for old male skin on the abdomen, cheek, palm, back, arm, forearm, ear and forehead.

FIG. 23A is a graph of the modulus values for young female skin on the abdomen, cheek, palm, back, arm, forearm, ear and forehead. FIG. 23B is a graph of the modulus values for old female skin on the abdomen, cheek, palm, back, arm, forearm, ear and forehead. FIG. 23C is a graph of the modulus values for young male skin on the abdomen, cheek, palm, back, arm, forearm, ear and forehead. FIG. 23D is a graph of the modulus values for old male skin on the abdomen, cheek, palm, back, arm, forearm, ear and forehead.

FIG. 24A is a graph of the modulus values for young female skin on the abdomen, cheek, palm, back, arm, forearm, ear and forehead. FIG. 24B is a graph of the modulus values for old female skin on the abdomen, cheek, palm, back, arm, forearm, ear and forehead. FIG. 24C is a graph of the modulus values for young male skin on the abdomen, cheek, palm, back, arm, forearm, ear and forehead. FIG. 24D is a graph of the modulus values for old male skin on the abdomen, cheek, palm, back, arm, forearm, ear and forehead.

FIG. 25A is a graph of the modulus for young skin; and FIG. 25B is a graph of the modulus for old skin.

FIG. 27A is a graph of the modulus values obtained from lesion (L) and normal (N) skin near and at the locations of skin cancers on the nose of a patient. FIG. 27B is a graph of the modulus values obtained from lesion (L) and normal (N) skin near and at the locations of skin cancers on the finger of a patient. FIG. 27C is a graph of the modulus values obtained from lesion (L) and normal (N) skin near and at the locations of skin cancers on the lip of a patient.

FIG. 38A is a photograph of a CMS device placed on a hear apex. FIG. 38B is a photograph of a CMS device placed on a left ventricle (LV). FIG. 38C is a photograph of a CMS device placed on a right ventricle (RV). FIG. 38D is a photograph of a CMS device placed on a lung. FIG. 28A is a graph of stress-strain curves from the CMS device placed on a hear apex, left ventricle (LV), right ventricle (RV), and lung. FIG. 28B is a graph of the modulus values extracted from the data in FIG. 28A and from CMS measurements (actuation voltage and frequency of 5 V and 1 kHz, respectively), as a function of sensor voltage. FIG. 28C shows the variation in modulus of a piece of explanted LV as a function of time.

DETAILED DESCRIPTION

Figures 1A, 1B, 1C, 1D, 1E, 1F, 1G:
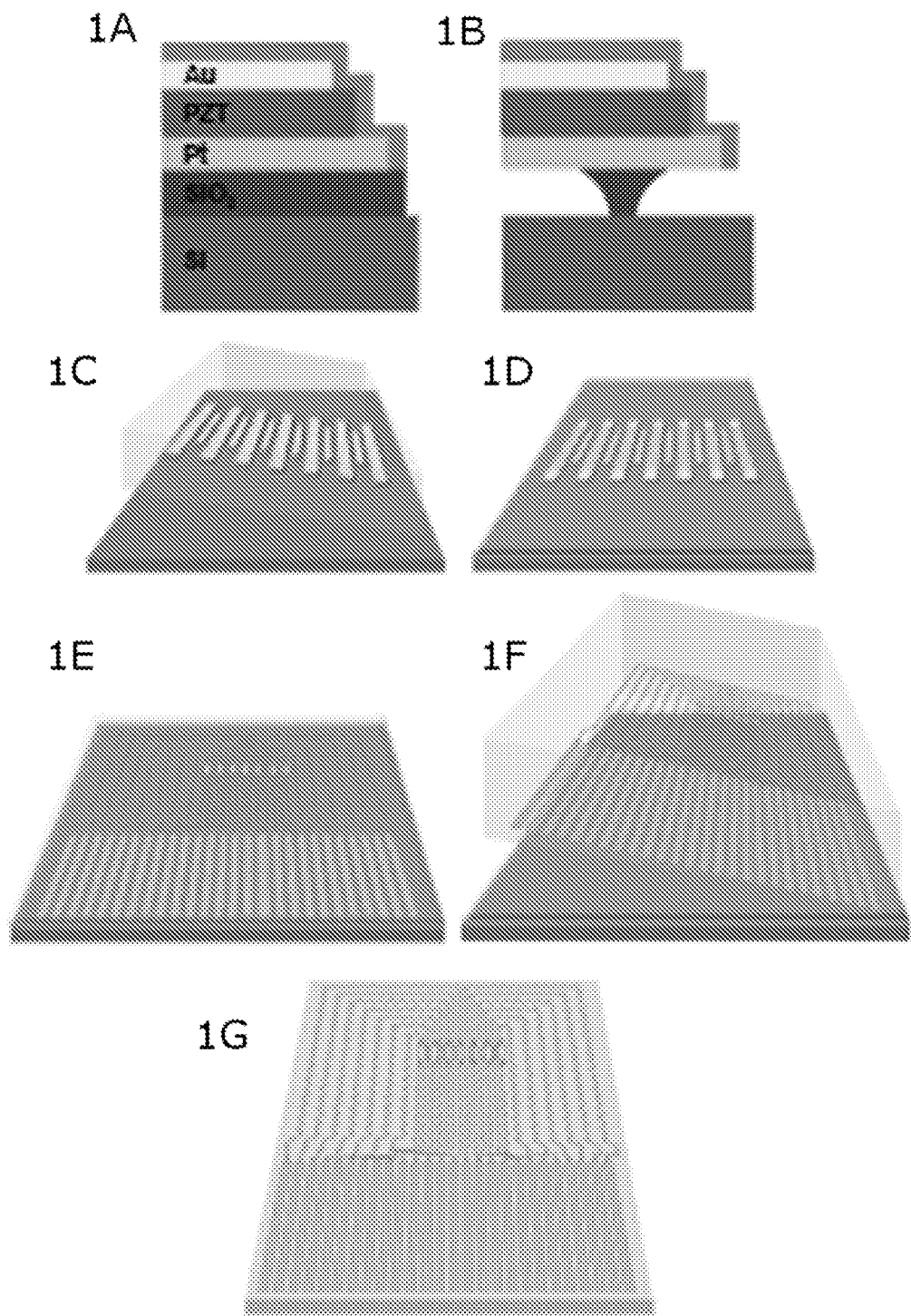
FIGS. 1A-1G depict a schematic illustration of procedures for fabricating a lead zirconate titanate (PZT) compliant modulus sensor (CMS) on a silicone substrate.

Materials and devices are provided for the sensing and manipulation of materials such as, e.g., the determination of biomechanical and physiochemical properties of tissues or tissue surfaces. Examples of use include soft tissues such as skin or adipose tissues or more dense tissues such as muscle or heart or dense tissues such as bone. The materials and devices provide for in vivo measurements of biomechanical properties at the tissue surface, e.g. near surface regions of the epidermis or dermis or underlying structures. The devices can be non-invasive and/or non-destructive to the material and, especially for the biomaterials, can be biocompatible and/or biodegradable. The materials and devices can use ultrathin, stretchable networks of mechanical actuators and sensors constructed with nanoribbons of lead zirconate titanate (PZT). In some embodiments, soft, reversible lamination onto the skin enables rapid, quantitative assessment of the viscoelastic moduli, with ability for spatial mapping. The materials and devices can provide accurate and reproducible measurements of both the storage and loss moduli for a variety of substrates and conditions. The disclosure discloses methods of making the devices and methods of using the devices for sensing and manipulation of material properties, including soft tissue such as the skin.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting. The skilled artisan will recognize many variants and adaptations of the embodiments described herein. These variants and adaptations are intended to be included in the teachings of this disclosure and to be encompassed by the claims herein.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Embodiments of the present disclosure will employ, unless otherwise indicated, techniques of molecular biology, microbiology, nanotechnology, organic chemistry, biochemistry, mycology, botany and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'x, y, z, or greater' should be interpreted to include the specific ranges of 'about x', 'about y', and 'about z' as well as the ranges of 'greater than x', greater than y', and 'greater than z'. In some embodiments, the term "about" can include traditional rounding according to significant figures of the numerical value. In addition, the phrase "about 'x' to 'y'" includes "about 'x' to about 'y'".

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The terms "subject" and "patient," as interchangeably used herein, refer to both human and non-human or veterinary subjects to which the devices described herein can be attached. The subject can be a mammal, including both a human and non-human mammals such as mice, rats, rabbits, and primates. Subject can include vertebrates, such other primates, dogs, cats, horses, and cows or invertebrates. When the subject is a human, the human can be a fetus (for in utero use), an infant (about 0 to 18 months), child (about 1.5 to 12 years), adolescent (about 12-18 years), young adult (about 18 to 35 years), middle adult (about 35 to 55 years), or late adult (over about 55 years).

The term "tissue surface", as used herein, refers broadly to the outer border or perimeter of a tissue, i.e. its ectoluminal surface or external perimeter. In addition this may include any exposed surface to which the described construct may be applied, e.g. an internal surface now exposed via surgery or other manipulation. Tissue surfaces include the area occupied outside of organ or organ component structures or other somatic materials, e.g. endothelial cells and matter attached a tissue layer, i.e. extracellular matrix materials, such as collagen, proteoglycans, glycoproteins, elastin, fibrin, plaque, agent, other molecules, or combinations thereof. The tissue surface can be a "soft tissue" surface. The term "soft tissue", as used herein, refers to all organs, organ components or other tissue or somatic structures that have some element of pliability as is understood by the biomedical community. This may include soft tissues that are now hardened by disease such as calcification or fibrosis. In biomedical parlance hard tissues implies bone and teeth and other normally mineralized tissues and structures. The tissue surface can be skin, e.g. the dermis, epidermis, or the stratum corneum (outermost layer of the epidermis).

The terms "skin device" and "epidermal device", as used interchangeably herein, refer to devices that can be placed on the skin e.g. that are capable of conformal contact with the skin surface. The tissue surface can be a serosal surface, i.e. the surface of the serosa or serous membrane on the surface of an organ. Serous membranes can be characterized by a single layer of mesothelial cells attached to the surface of a thin layer of collagenous tissue, which is connected to the underlying endothoracic-transversalis fascia. Serous membranes can be found encompassing organs such as the heart, liver, intestines, and lungs. Serous membranes include pleura, peritoneal membranes and pericardium. The term "serosal device", as used herein, refers to a device capable of making conformal contact with a serosal surface. The tissue surface can be a luminal surface, i.e. a surface on the interior of a body lumen or body passageway. A lumen or a body passageway can be an existing lumen or a lumen created by surgical intervention. As used in this specification, the terms "lumen" or "body passageway," and "vessel" should have a broad meaning and encompasses any duct (e.g., natural or iatrogenic) or cavity within the human body and can include a member selected from the group comprising: blood vessels, respiratory ducts, gastrointestinal ducts. The term "endoluminal", as used herein, refers to or describes objects that can be placed inside or moved through a lumen or a body passageway in a human or animal body. The term "endoluminal device" describes devices that can be placed inside or moved through any such lumen. The term "ectoluminal device" describes devices that can be placed on the ectoluminal or outer surface. The term "endomural device" describes devices that can be placed inside or in the middle of a tissue.

The term "biomechanical property", as used herein with regards to tissue properties, refers to one or more mechanical properties, electrical properties, physical properties, or material properties of a biological tissue. Biomechanical properties include, but are not limited to, the tissue response to a mechanical load, the elastic modulus, the Young's modulus, the stress, the strain, stress relaxation properties, creep properties, fracture and tensile properties, the density, the Poisson's ratio, the viscosity, the thermo-elasticity, the thermal-conductivity, displacement, velocity, acceleration, mass, damping, stiffness, force, pressure, temperature, hydration, water/fluid content or electrical measures such as capacitance, voltage, current, or resonance.

The terms "conformable" and "conformal", as used herein, refer to a device, material or substrate which has a bending stiffness sufficiently low to allow the device, material or substrate to adopt the contour profile of the surface onto which it is attached, for example a contour profile allowing for conformal or otherwise intimate contact with a surface having a pattern of relief or recessed features. In certain embodiments, a desired contour profile is that of a tissue surface in a biological environment, for example skin (stratum corneum), a serous membrane such as the peritoneum, the pleura, or the pericardium, or a luminal surface such as the endoluminal surface of blood vessels, respiratory ducts, or gastrointestinal ducts.

The term "conformal contact", as used herein, refers to contact established between a device and a receiving surface, which may for example be a target tissue in a biological environment. In one aspect, conformal contact involves a macroscopic adaptation of one or more surfaces (e.g., contact surfaces) of a device to the overall shape of a tissue surface. In another aspect, conformal contact involves a microscopic adaptation of one or more surfaces (e.g., contact surfaces) of a device to a tissue surface resulting in an intimate contact substantially free of voids. In an embodiment, conformal contact involves adaptation of a contact surface(s) of the device to a receiving surface(s) of a tissue such that intimate contact is achieved, for example, wherein less than 20% of the surface area of a contact surface of the device does not physically contact the receiving surface, or optionally less than 10% of a contact surface of the device does not physically contact the receiving surface, or optionally less than 5% of a contact surface of the device does not physically contact the receiving surface. Conformal contact includes large area conformal contact, for example, wherein conformal contact between a tissue and device component is over an area of about 100 $\mu m^2$, 500 $\mu m^2$, 1,000 $\mu m^2$, 10,000 $\mu m^2$, 50,000 $\mu m^2$, 0.1 $mm^2$, 1 $mm^2$, 100 $mm^2$, 1,000 $mm^2$, or 10,000 $mm^2$, or greater.

The terms "bendable" and "flexible", as used interchangeably herein, refer to the ability of a material, structure, device or device component to be deformed into a curved or bent shape without undergoing a transformation that introduces significant strain, such as strain characterizing the failure point of a material, structure, device or device component. In some embodiments, a flexible material, structure, device or device component may be deformed into a curved shape without introducing strain of about 50%, 40%, 30%, 25%, 10%, 5%, 1%, or larger, and for yet other embodiments larger than or equal to 0.5% in strain-sensitive regions. As used herein, some, but not necessarily all, flexible structures are also stretchable. A variety of properties provide flexible structures (e.g., device components), including materials properties such as a low modulus, bending stiffness and flexural rigidity; physical dimensions such as small average thickness (e.g., less than 100 microns, optionally less than 10 microns and optionally less than 1 micron) and device geometries such as thin film and mesh geometries.

In this description, a "bent configuration" refers to a structure having a curved conformation resulting from applying a force. Bent structures may have one or more folded regions, convex regions, concave regions, and any combinations thereof. Useful bent structures, for example, may be in a coiled conformation, a wrinkled conformation, a buckled conformation, a serpentine conformation, and/or a wavy (i.e., wave-shaped) configuration. Bent structures, such as stretchable bent interconnects, may be bonded to a flexible substrate, such as a polymer and/or elastic substrate, in a conformation wherein the bent structure is under strain. In some embodiments, the bent structure, such as a bent ribbon structure, is under a strain equal to or less than 30%, optionally a strain equal to or less than 10%, optionally a strain equal to or less than 5% or optionally a strain equal to or less than 1%. In some embodiments, the bent structure, such as a bent ribbon structure, is under a strain selected from the range of 0.5% to 30%, optionally a strain selected from the range of 0.5% to 10%, and optionally a strain selected from the range of 0.5% to 5%. Alternatively, the stretchable bent interconnects may be bonded to a substrate that is a substrate of a device component, including a substrate that is itself not flexible, The substrate itself may be planar, substantially planar, curved, have sharp edges, or any combination thereof. Stretchable bent interconnects are available for transferring to any one or more of these complex substrate surface shapes.

The term "stretchable", as used, refers to the ability of a material, structure, device or device component to be strained without undergoing fracture. In some embodiments, a stretchable material, structure, device or device component may undergo strain of about 0.5%, 1%, 5%, 10%, 15%, 25%, 30%, 40%, 50%, or larger without fracturing. A used herein, many stretchable structures are also flexible. Some stretchable structures (e.g., device components) are engineered to undergo compression, elongation and/or twisting to be able to deform without fracturing. Stretchable structures include thin film structures comprising stretchable materials, such as elastomers; bent structures capable of elongation, compression and/or twisting motion; and structures having an island-bridge geometry. Stretchable device components include structures having stretchable interconnects, such as stretchable electrical interconnects.

The term "bending stiffness", as used herein, is a mechanical property of a material, device or layer describing the resistance of the material, device or layer to an applied bending moment. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

The terms "young's modulus" and "modulus", as used interchangeably herein, refer to a mechanical property of a material, device or layer that refers to the ratio of stress to strain for a substance. Young's modulus may be provided by the expression:

$$E = \frac{(\text{stress})}{(\text{strain})} = \left(\frac{L_0}{\Delta L}\right)\left(\frac{F}{A}\right),$$

where E is Young's modulus, $L_0$ is the equilibrium length, $\Delta L$ is the length change under the applied stress, F is the force applied and A is the area over which the force is applied. Young's modulus may also be expressed in terms of Lame constants via the equation:

$$E = \frac{\mu(3\lambda + 2\mu)}{\lambda + \mu},$$

where $\lambda$ and $\mu$ are Lame constants. High Young's modulus (or "high modulus") and low Young's modulus (or "low modulus") are relative descriptors of the magnitude of Young's modulus in a material, layer or device. In some embodiments, a high Young's modulus is larger than a low Young's modulus, preferably 10 times larger for some applications, more preferably 100 times larger for other applications and even more preferably 1000 times larger for yet other applications. "Inhomogeneous Young's modulus" refers to a material having a Young's modulus that spatially varies (e.g., changes with surface location). A material having an inhomogeneous Young's modulus may optionally be described in terms of a "bulk" or "average" Young's modulus for the entire layer of material. "Low modulus" refers to materials having a Young's modulus less than or equal to 10 MPa, less than or equal to 5 MPa, or optionally less than or equal to 1 MPa and optionally for some applications less than or equal to 0.1 MPa.

The term "compression", as used herein, is similar to the strain, but specifically refers to a force that acts to decrease a characteristic length, or a volume, of a substrate, such that $\Delta L < 0$.

The term "elastomer", as used herein, refers to a polymeric material which can be stretched or deformed and return to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers useful include, but are not limited to, thermoplastic elastomers, styrenic materials, olefenic materials, polyolefin, polyurethane thermoplastic elastomers, polyamides, natural and synthetic rubbers, PDMS, polybutadiene, polyisobutylene, poly(styrene-butadiene-styrene), polyurethanes, polychloroprene and silicones. In some embodiments, an elastomeric stamp can be an elastomer. Exemplary elastomers include, but are not limited to silicon containing polymers such as polysiloxanes including poly(dimethyl siloxane) (i.e. PDMS and h-PDMS), poly (methyl siloxane), partially alkylated poly(methyl siloxane), poly(alkyl methyl siloxane) and poly(phenyl methyl siloxane), silicon modified elastomers, thermoplastic elastomers, styrenic materials, olefenic materials, polyolefin, polyurethane thermoplastic elastomers, polyamides, synthetic rubbers, polyisobutylene, poly(styrene-butadiene-styrene), polyurethanes, polychloroprene and silicones. In an embodiment, a flexible polymer is a flexible elastomer.

The terms "biocompatible" and "biologically compatible", as used interchangeably herein, refer to materials that are, with any metabolites or degradation products thereof, generally non-toxic to the recipient, and cause no significant adverse effects to the recipient. Generally speaking, biocompatible materials are materials which do not elicit a significant inflammatory or immune response when administered to a patient. In some embodiments a biocompatible material elicits no detectable change in one or more biomarkers indicative of an immune response. In some embodiments, a biocompatible material elicits no greater than a 10% change, no greater than a 20% change, or no greater than a 40% change in one or more biomarkers indicative of an immune response.

The term "biodegradable", as used herein, means that the material, structure, device, or device component degrades or breaks down into its component subunits, or digestion products, e.g., by a chemical (hydration) or biochemical process, of the material into smaller (e.g., non-polymeric) subunits. In some embodiments, a biodegradable material, structure, device, or device component degrades into $CO_2$, $H_2O$, and other biomass materials. In some embodiments, the degradation occurs over a period less than 30 days, less than 60 days, less than 90 days, less than 120 days, less than 180 days, less than 1 year. In some embodiments the degradation occurs over a period greater than 30 days, greater than 60 days, greater than 90 days, greater than 120 days, greater than 180 days, or greater than 1 year. In certain embodiments degradation of a material, structure, device, or device component is said to be complete when at least 80% by mass has degraded, when at least 85% by mass has degraded, when at least 90% by mass has degraded, when at least 95% by mass has degraded, or when at least 99% by mass has degraded. The biodegradation rate depends upon several factors, both environmental and material. Non-limiting examples of environmental factors influencing biodegradation rates include temperature, pH, oxygen concentrations, and microbial and enzymatic activities. Non-limiting examples of material properties influencing biodegradation rates include degree of branching of the polymer chains, the presence and amount of hydrophilic groups, stereochemistry, molecular weight, the degree of crystalinity, the crosslinking, surface roughness, and the surface to volume ratio.

The term "time-limited", as used herein, means that the material, structure, device, or device component degrades, breaks down, or loses some aspect of intended function over time. In some embodiments this can be via biodegradation. Time-limited can mean the degradation occurs by other intrinsic or exogenous means, such as specific changes in physiological conditions, pH, or temperature. In some cases time-limited materials do not begin to degrade or do not begin to significantly degrade until after a specific stimulus, i.e. an electrical, ultrasonic, or chemical signal may be employed to initiate degradation of one or more materials such that degradation can be initiated at a specific time that need not be predetermined. The degradation of time-limited materials can occur via hydrolysis, oxidation, reduction, enzymatic degradation, radicals, Norrish type I mechanisms, Norrish type II mechanisms, or by other mechanisms known in the art such as the biodegradation of polyethylene or paraffin as described in "The mechanism of biodegradation of polyethylene" by Albertsson et al., *Polymer Degradation and Stability,* 18:73-87 (1987).

The terms "component" and "element", as used interchangeably herein, broadly refer to a material or individual component used in a device. An "interconnect" is one example of a component and refers to an electrically conducting material capable of establishing an electrical connection with a component or between components. An interconnect may establish electrical contact between components that are separate and/or can move relative to each other. Depending on the desired device specifications, operation, and application, an interconnect can be made from a suitable material. For applications where a high conductivity is required, typical interconnect metals may be used, including but not limited to copper, silver, gold, aluminum and the like, and alloys thereof. Suitable conductive materials further include semiconductors, such as silicon and GaAs and other conducting materials such as indium tin oxide. In certain embodiments the interconnect is an organic semiconductor, preferably a polymeric organic semiconductor. Components include, but are not limited to a capacitor, resistor, photodiode, LED, TFT, electrode, semiconductor, other light-collecting/detecting components, transistor, integrated circuit, contact pad capable of receiving a device component, thin film devices, circuit elements, control elements, microprocessors, transducers and combinations thereof.

An interconnect that is "stretchable" or "flexible" is used herein to broadly refer to an interconnect capable of undergoing a variety of forces and strains such as stretching, bending and/or compression in one or more directions without adversely impacting electrical connection to, or electrical conduction from, a device component A stretchable interconnect may be formed of a relatively brittle material, such as GaAs, yet remain capable of continued function even when exposed to a significant deformatory force (e.g., stretching, bending, compression) due to the interconnect's geometrical configuration. In an exemplary embodiment, a stretchable interconnect may undergo strain larger than 1%, optionally 10% or optionally 30% or optionally up to 100% without fracturing. In an example, the strain is generated by stretching an underlying elastomeric substrate to which at least a portion of the interconnect is bonded. For certain embodiments, flexible or stretchable interconnects include interconnects having wavy, meandering or serpentine shapes. Flexible serpentine interconnects are described, for example, in U.S. Pat. No. 8,552,299, the description of which is incorporated by reference herein.

The terms "actuating element" and "actuator", as used interchangeably herein, refer to a device component useful for interacting with, stimulating, controlling, or otherwise affecting an external structure, material or fluid, for example a biological tissue. Useful actuating elements include, but are not limited to, electrode elements, electromagnetic radiation emitting elements, light emitting diodes, lasers and heating elements. Actuating elements include electrodes for providing a voltage or current to a tissue. Actuating elements include sources of electromagnetic radiation for providing electromagnetic radiation to a tissue. Actuating elements include ablation sources for ablating tissue. Actuating elements include thermal sources for heating tissue. Actuating elements include displacement sources for displacing or otherwise moving a tissue.

The terms "sensing element" and "sensor", as used interchangeably herein, refer to a device component useful as a sensor and/or useful for detecting the presence, absence, amount, magnitude or intensity of a physical property, object, radiation and/or chemical. Sensors in some embodiments function to transduce a biological signal into an electrical signal, optical signal, wireless signal, acoustic signal, etc. Useful sensing elements include, but are not limited to electrode elements, chemical or biological sensor elements, pH sensors, optical sensors, photodiodes, temperature sensors, capacitive sensors strain sensors, acceleration sensors, movement sensors, displacement sensors, pressure sensors, acoustic sensors or combinations of these.

The term "coincident", as used herein, refers to the relative position of two or more objects, planes or surfaces, for example a surface that is positioned within or is adjacent to a layer, such as a functional layer, substrate layer, or other layer.

The term "dielectric", as used herein, refers to a non-conducting or insulating material. In an embodiment, an inorganic dielectric can be a dielectric material substantially free of carbon. Specific examples of inorganic dielectric materials include, but are not limited to, silicon nitride and silicon dioxide.

The term "semiconductor" refers to any material that is an insulator at a low temperature, but which has an appreciable electrical conductivity at temperatures of about 300 Kelvin. Use of the term semiconductor is consistent with this term in the art of microelectronics and electronic devices. In some embodiment the semiconductor is an inorganic semiconductor. In some embodiments the semiconductor is an organic semiconductor. In some embodiments the semiconductor is a polymeric organic semiconductor. Useful inorganic semiconductors include those comprising element semiconductors, such as silicon, germanium and diamond, and compound semiconductors, such as group IV compound semiconductors such as SiC and SiGe, group III-V semiconductors such as AlSb, AlAs, Aln, AlP, BN, GaSb, GaAs, GaN, GaP, InSb, InAs, InN, and InP, group III-V ternary semiconductors alloys such as $Al_xGa_{1-x}As$, group II-VI semiconductors such as CsSe, CdS, CdTe, ZnO, ZnSe, ZnS, and ZnTe, group I-VII semiconductors CuCl, group IV-VI semiconductors such as PbS, PbTe and SnS, layer semiconductors such as $PbI_2$, $MoS_2$ and GaSe, oxide semiconductors such as CuO and $Cu_2O$. The term semiconductor includes intrinsic semiconductors and extrinsic semiconductors doped with one or more selected materials, including semiconductor having p-type doping materials and n-type doping materials, to provide beneficial electronic properties useful for a given application or device. The term semiconductor includes composite materials comprising a mixture of semiconductors and/or dopants. Specific semiconductor materials useful for in some embodiments include, but are not limited to, Si, Ge, SiC, AlP, AlAs, AlSb, GaN, GaP, GaAs, GaSb, InP, InAs, GaSb, InP, InAs, InSb, ZnO, ZnSe, ZnTe, CdS, CdSe, ZnSe, ZnTe, CdS, CdSe, CdTe, HgS, PbS, PbSe, PbTe, AlGaAs, AlInAs, AlInP, GaAsP, GaInAs, GaInP, AlGaAsSb, AlGaInP, and GaInAsP.

Porous silicon semiconductor materials are useful for applications of aspects described herein in the field of sensors and light emitting materials, such as light emitting diodes (LEDs) and solid state lasers. Useful organic semiconductors include acenes, perylenes, fullerenes, phthalocyanines, oligothiophenes, and substituted derivatives thereof. Particular organic semiconductor compounds include sexithiophene, α,ω-dihexylsexithiophene, quinquethiophene, quaterthiophene, α,ω-dihexylquaterthiophene, α,ω-dihexylquinquethiophene, bis(dithienothiophene), anthradithiophene, dihexylanthradithiophene, polyacetylene, polythienylenevinylene, $C_{60}$, [6,6]-phenyl-$C_{61}$-butyric acid methyl ester, copper(II) hexadecafluorophthalocyanine, and N,N'-bis(pentadecafluoroheptylmethyl)naphthalene-1, 4,5,8-tetracarboxylic diimide. Useful polymeric organic semiconductors include polyacetylenes, polydiacetylenes, polypyroles, polythiophenes, polyphenylenes, poly(arylene vinylenes), polyanilies, and copolymer and derivatives thereof. Particular polymeric organic semiconductors include poly(3-hexylthiophene), poly(phenylene vinylene), and poly(pyrrole). Organic semiconductors offer several advantages including inexpensive, easy shaping and manufacturing, a wide range of tunable properties via synthetic modifications, high degree of flexibility (especially in thin film devices), and their compatibility with a wide variety of substrates.

The term "electrical contact", as used herein, refers to the condition that allows two or more materials and/or structures to transfer charge between each other, such as in transferring electrons or ions. Electrical communication refers to a configuration of two or more components such that an electronic signal or charge carrier can be directly or indirectly transferred from one component to another. As used herein, electrical communication includes one-way and two-way electrical communication. In some embodiments, components in electrical communication are in direct electrical communication wherein an electronic signal or charge carrier is directly transferred from one component to another. In some embodiments, components in electrical communication are in indirect electrical communication wherein an electronic signal or charge carrier is indirectly transferred from one component to another via one or more intermediate structures, such as circuit elements, separating the components.

The term "functional layer", as used herein, refers to a layer in a device or device component that imparts some functionality to the device or device component. The functional layer may be a thin film such as a semiconductor layer. Alternatively, the functional layer may have multiple layers, such as multiple semiconductor layers separated by support layers. The functional layer may have a plurality of patterned elements, such as interconnects running between device-receiving pads or islands. The functional layer may be heterogeneous or may have one or more properties that are inhomogeneous. "Inhomogeneous property" refers to a physical parameter that can spatially vary, effecting the position of the neutral mechanical surface (NMS) within the multilayer device.

The term "substrate" refers to a material having a surface capable of supporting a structure, including an electronic device or electronic device component. A structure that is "bonded" to the substrate refers to a portion of the structure in physical contact with the substrate and unable to substantially move relative to the substrate surface to which it is bonded. Unbonded portions are capable of substantial movement relative to the substrate.

The term "ultrathin", as used herein, refers to devices of thin geometries that exhibit extreme levels of bendability. In one embodiment, ultrathin refers to circuits having a thickness of about 10,000 nm, 5,000 nm, 1,000 nm, 600 nm, 500 nm, 400 nm, 200 nm, or less. In some embodiments, a multilayer device that is ultrathin has a thickness of about 50,000 nm, 25,000 nm, 20,000 nm, 15,000 nm, 10,000 nm, 5,000 nm, 1,000 nm, 500 nm, or less.

The term "spatially aligned", as used herein, refers to positions and/or orientations of two or more structures that are defined regarding each other. Spatially aligned structures may have positions and/or orientations that are preselected regarding each other, for example, preselected to within 1 micron, preferably for some applications to within 500 nanometers, and more preferably for some applications to within 50 nanometers.

The term "spatial variation", as used, refers to a parameter that has magnitude that varies over a surface, and is useful for providing two-dimensional control of component relief features, providing spatial control over the bendability of a device or device component.

The term "barrier layer", as used herein, refers to a device component spatially separating two or more other device components or spatially separating a device component from a structure, material or fluid external to the device. In one embodiment, a barrier layer encapsulates one or more device components. In embodiments, a barrier layer separates one or more device components from an aqueous solution, a biological tissue and/or a biological environment. In some embodiments, a barrier layer is a passive device component. In some embodiments, a barrier layer is a functional, but non-active, device component. In a specific embodiment, a barrier layer is a moisture barrier. As used herein, the term "moisture barrier" refers to a barrier layer which provides protection to other device components from bodily fluids, ionic solutions, water or other solvents. In one embodiment, a moisture barrier provides protection to an external structure, material or fluid, for example, by preventing leakage current from escaping an encapsulated device component and reaching the external structure, material or fluid. In a specific embodiment, a barrier layer is a thermal barrier.

As used herein, the term "thermal barrier" refers to a barrier layer which acts as a thermal insulator, preventing, reducing or otherwise limiting transferring heat from one device component to another or from a device component to an external structure, fluid or material. Useful thermal barriers include those comprising materials having a thermal conductivity of 0.3 W/m-K or less, such as selected over the range of 0.001 to 0.3 W/m-K. In some embodiments, a thermal barrier can have active cooling components, such as components known in the art of thermal management, such as thermoelectric cooling devices and systems. Thermal barriers also include those barriers comprising thermal management structures, such as structures useful for transporting heat away from a portion of a device or tissue; in these and other embodiments, a thermal barrier can be a thermally conductive material, for example material having a high thermal conductivity, such as a thermal conductivity characteristic of a metal.

The term "encapsulate", as used herein, refers to the orientation of one structure such that it is at least partially, and sometimes completely, surrounded by one or more other structures. "Partially encapsulated" refers to the orientation of one structure such that it is partially surrounded by one or more other structures. "Completely encapsulated" refers to the orientation of one structure such that it is completely surrounded by one or more other structures. The invention includes implantable devices having partially or completely encapsulated electronic devices, device components and/or inorganic semiconductor components and/or electrodes.

The term "selectively permeable", as used herein, refers to a property of a material to allow certain substances to pass through the material while preventing other substances from being passed through. In one embodiment, a selectively permeable material allows one or more target chemicals, molecules and/or biomolecules to be passed through the material while preventing water, ionic solutions, bodily fluids, salts, proteins and other substances from being passed through the material. In an embodiment, the barrier layer of a device has spatially patterned permeable regions, impermeable regions or a combination of both permeable regions and impermeable regions.

Devices for Sensing and Manipulation of Materials

Devices are provided that can be used for contact sensing and manipulation of a material to determine one or more properties. The terms "contact sensing" and "contact manipulation", as used herein refer to methods of sensing and manipulation that can be accomplished through contacting a surface of a material. The contact methods can be non-destructive to the material. For example, with regard to biomaterials the contact sensing and contact manipulation can be performed non-invasively. The devices can be used for biomechanical sensing and manipulation of tissue, in particular soft tissue and soft tissue surfaces. Biomechanical sensing and manipulation, as used herein, refers to forms of contact sensing and contact manipulation, respectively, where the sensing and manipulation can be performed non-invasively, where the sensing and/or manipulation is capable of sensing changes or manipulating materials on a scale that is relevant for biochemical properties.

The devices can be multi-layer devices, especially multi-layer devices with thin, flexible structures. The devices can be conformable. For example, the devices can be capable of making conformal contact with the surface of a material such as, e.g., a soft tissue. Suitable soft tissue surfaces can include the skin, luminal surfaces, or a serosal surface of a soft tissue or organ. Other suitable materials can include ceramics, glasses, metals, rubbers, polymers, and combinations thereof. In some embodiments, the devices can be applied and can make conformal contact with the surface of ceramics, glasses, metals, polymers, and combinations thereof. The deformation energy of the material to the device being adhered to the material surface can be smaller in magnitude than the adhesion energy of the device to the material, sometimes at least 10%, 20%, 30%, 40%, or 50% smaller.

The devices can be stretchable, flexible, and/or thin. In some embodiments the devices have a thickness of about 1 mm, 0.8 mm, 0.6 mm, 0.4 mm, 0.2 mm, 100,000 nm, 50,000 nm, 20,000 nm, 10,000 nm, 5,000 nm, 2,000 nm, 1,000 nm, or less. The devices can be conformable. In some embodiments the devices are capable of making conformal contact with the surface of a soft tissue over an area of about 100 $\mu m^2$ to 1 $mm^2$, about 1,000 $\mu m^2$ to 500,000 $\mu m^2$, about 10,000 µm² to 100,000 µm², about 100 µm² to 10,000 mm², about 100,000 µm² to 1,000 mm², or about 1 mm² to 100 mm².

The devices can be stable of long periods of repeated use. For example, the devices in some embodiments can be adhered to the surface, removed, and re-adhered to the same surface or a different surface. This can be done both non-destructively and/or non-invasively. An electrical performance characteristic of the device can be stable after from about 10 to 10,000, about 10 to 5,000 about 50 to 5,000, about 50 to 1,000, about 50 to 500, or about 100 to 500 bending cycles with a uniaxial strain of about 5%, 10%, 15%, 20%, 25%, 30%, 40%, 50%, or more. The electrical performance characteristic can be any electrical signal from the device, for example the output voltage of a sensing element, the output current of a sensing element, the output resistance of a sensing element, or a combination thereof.

The devices can be used for biomechanical sensing of soft tissues and soft tissue surfaces. The devices can include one or more sensing elements. The biomechanical sensing can include detecting, measuring, and/or mapping of a biomechanical property of the soft tissue or tissue surface. Biomechanical properties can include, for example, elasticity, elastic modulus, stress, strain, rigidity, displacement, force, and combinations thereof.

The devices can be used for manipulation of materials such as, e.g., soft tissues and soft tissue surfaces. The manipulation can include biomechanical manipulation of the soft tissue or soft tissue surface. The manipulation can include biomechanical manipulation, electrical manipulation, chemical manipulation, or a combination thereof. In some embodiments, the biomechanical manipulation can include physical manipulations such as applying a force to depress, displace, or stretch the soft tissue or soft tissue surface. For example, the devices can include an actuator element that induces mechanical motions in the device and in the soft tissue or soft tissue surface to which the device is attached.

Elastomeric Substrate

The device can include an elastomeric substrate. The elastomeric substrate forms a scaffold that supports one or more elements or components. The elements are capable of locally monitoring, sensing, enhancing, attenuating, and/or impacting the function of a soft tissue or soft tissue surface. In some embodiments the elastomeric substrate is biocompatible and/or biodegradable. In some embodiments, the elastomeric substrate also serves as a controlled release matrix or contains a controlled release polymer matrix for delivery of one or more therapeutic, prophylactic, or diagnostic agents.

Useful elastomers can include, but are not limited to, thermoplastic elastomers, styrenic materials, olefenic materials, polyolefin, polyurethane thermoplastic elastomers, polyamides, natural and synthetic rubbers, PDMS, polybutadiene, polyisobutylene, poly(styrene-butadiene-styrene), polyurethanes, polychloroprene and silicones. In some embodiments, an elastomeric stamp can be an elastomer. Exemplary elastomers include, but are not limited to silicon containing polymers such as polysiloxanes including poly (dimethyl siloxane) (i.e. PDMS and h-PDMS), poly(methyl siloxane), partially alkylated poly(methyl siloxane), poly (alkyl methyl siloxane) and poly(phenyl methyl siloxane), silicon modified elastomers, thermoplastic elastomers, styrenic materials, olefenic materials, polyolefin, polyurethane thermoplastic elastomers, polyamides, synthetic rubbers, polyisobutylene, poly(styrene-butadiene-styrene), polyurethanes, polychloroprene and silicones. In an embodiment, a flexible polymer is a flexible elastomer.

The elastomeric substrate can be a flexible, elastomeric material. The elastomeric substrate can be a material with a low Young's modulus, for example about 50 MPa, 30 MPa, 25 MPa, 20 MPa, 15 MPa, 10 MPa, or less. The elastomeric substrate can have any thickness depending upon the application, the properties of the elastomeric material, etc. The elastomeric substrate can in some embodiments have a thickness of about 10 nm to 10 µm, about 50 nm to 10 µm, about 50 nm to 5 µm, about 100 nm to 5 µm, or about 100 nm to 1 µm.

The elastomeric substrate can be polymers such as thermosettable, thermoplastic, polymerizable oligomers that polymerize in response to free radical or ion formation such as by photopolymerization, chemically or ionic crosslinking (i.e., through agents such as glutaraldehyde or ions like calcium ions). Either non-biodegradable or biodegradable materials can be used. For internal application to tissues to prevent inflammation, enlargement and/or overproliferation, it is preferred to use polymers degrading substantially within two months, six months, or twelve months after implantation.

Suitable materials are commercially available or readily synthesizable using methods known to those skilled in the art. These materials include: soluble and insoluble, biodegradable and non-biodegradable natural or synthetic polymers. These can be hydrogels or thermoplastics, homopolymers, copolymers or blends, natural or synthetic. As used herein, a hydrogel is defined as an aqueous phase with an interlaced polymeric component, preferably with 90% of its weight as water.

Representative natural polymers include proteins such as, e.g., zein, modified zein, casein, gelatin, gluten, serum albumin, or collagen, and polysaccharides, such as cellulose, dextrans, hyaluronic acid, polymers of acrylic and methacrylic esters and alginic acid. These are not preferred due to higher levels of variability in the characteristics of the final products, and in degradation following administration. Synthetically modified natural polymers include alkyl celluloses, hydroxyalkyl celluloses, cellulose ethers, cellulose esters, and nitrocelluloses, acrylic or methacrylic esters of above natural polymers to introduce unsaturation into the biopolymers.

Representative synthetic polymers are: poly(hydroxy acids) such as poly(lactic acid), poly(glycolic acid), and poly(lactic acid-glycolic acid), poly(lactide), poly(glycolide), poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terephthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and copolymers thereof, derivatized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt (jointly referred to herein as "synthetic celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly (hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-coaprolactone), derivatives, copolymers and blends thereof. Synthetic polymers can include polyesters, polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polysiloxanes, polyurethanes and copolymers thereof. Other polymers include celluloses such as methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, acrylates such as poly(methyl methacrylate), poly(ethyl methacrylate), poly(butyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(vinyl acetate), polyvinyl chloride, polystyrene, polyvinyl pyrrolidone, and polyvinylphenol. Representative bioerodible polymers include polylactides, polyglycolides and copolymers thereof, poly(hydroxy butyric acid), poly(hydroxyvaleric acid), poly(lactide-co-caprolactone), poly[lactide-co-glycolide], polyanhydrides, polyorthoesters, derivatives, blends and copolymers thereof. As used herein, "derivatives" include polymers having substitutions, additions of chemical groups, for example, alkyl, alkylene, hydroxylations, oxidations, and other modifications routinely made by those skilled in the art.

Examples of biodegradable polymers include polymers of hydroxyacids such as lactic acid and glycolic acid, and copolymers with PEG, polyanhydrides, poly(ortho)esters, polyurethanes, poly(butyric acid), poly(valeric acid), poly (lactide-coaprolactone), Tyrosine-based pseudo-peptide polymers and the like, blends and copolymers thereof. Examples of preferred non-biodegradable polymers include ethylene vinyl acetate, poly(meth)acrylic acid, polyamides, copolymers and mixtures thereof. The biodegradable materials degrade either by enzymatic hydrolysis or exposure to water in vivo, or by surface or bulk erosion.

Substrate materials can also include tissue adhesives. In one form, fibrin is used. This has the advantage it can be formed easily in situ using the patient's own fibrinogen, blood or serum, by addition of thrombin and calcium chloride. The materials described above can also be used. Other polymeric tissue adhesives commercially available include cyanoacrylate glues, GRF (gelatin-resorcinol-formaldehyde) and polyethyleneglycol-poly(lactic acid and/or glycolic acid)-acrylates, both of which are applied as liquids and then photopolymerized.

Actuating Elements and Sensing Elements

The devices can contain an actuating element, such as any actuating element described herein. The devices can also contain a sensing element, many of which are described herein. The sensing element can be mechanically coupled to the actuating element. The sensing element and the actuating element can be mechanically coupled. The term "mechanically coupled", as applied herein, refers to the combination of material properties and spatial orientation between elements or components in the device such that a mechanical force or manipulation by or at a first element in the device induces a mechanical manipulation or a detectable mechanical displacement at a second element if the second element is mechanically coupled to the first element. For example, a sensing element can be said to be mechanically coupled to an actuating element when a biomechanical force or manipulation by the actuating element can be detected by the sensing element. The mechanical coupling can include coupling through an elastomeric substrate, through the material or the material surface, or both. For example, an actuating element can induce a biomechanical manipulation in the adjacent tissue or tissue surface; and a sensing element is biomechanically coupled to the actuating element when the biomechanical manipulation can be detected by the sensing element in the adjacent tissue or tissue surface, either by mechanical coupling through the soft tissue or soft tissue surface or by mechanical coupling through the substrate of the device. A sensing element can be mechanically coupled to one or more actuating elements, one or more other elements, one or more other sensing elements, and vice versa.

In some embodiments the device for contact sensing of a material property includes a thin elastomeric substrate, an actuating element, and a sensing element mechanically coupled to the actuating element. The sensing element can be, for example, substantially aligned with the actuating element. The term "substantially aligned", as used herein, refers to the relative orientation of two components or elements being such that the long axis of each of the components (the long axis being the longest straight-line distance through the component) is within 40°, within 30°, within 25°, within 20°, within 15° within 10°, or within 5° of being parallel. In some embodiments the long axes of two components that are substantially aligned are parallel or are within 1°, 2°, 3, or 4° of being parallel. The sensing element and the actuating element can be spatially localized in the device or on the substrate. Two components are spatially localized when the components are separated (center of mass to center of mass distance) by less than 5.0 mm, less than 4.0 mm, less than 3.0 mm, less than 2.5 mm, less than 2.0 mm, less than 1.5 mm, less than 1.0 mm, less than 0.75 mm, less than 0.5 mm, less than 0.25 mm, or less. In some embodiments the sensing element and the actuating element are both substantially aligned and spatially localized.

The device can contain one or more actuating element, one or more sensing element, or a combination of both. The device can contain 1, 2, 3, 4, 5, 6, 7, 8, or more actuating elements. Likewise the device can contain 1, 2, 3, 4, 5, 6, 7, 8, or more sensing elements. In some embodiments the device contains a plurality of actuating elements and a plurality of sensing elements. In some embodiments the number of sensing elements is less than (sometimes one less than) the number of actuating elements. Each of the sensing elements can be mechanically coupled to one or more actuating elements. The sensing elements and actuating elements can be substantially aligned and/or spatially localized. For example, each of the sensing elements can be substantially aligned and/or spatially localized with one or more actuating elements. One or more sensing element can be positioned between actuating elements such that the sensing and actuating elements are interdigitated.

The actuating elements and sensing elements can take any shape or structure known to those skilled in the art. In some embodiments the actuating elements, the sensing elements, or both will comprise a capacitor-type structure. A capacitor-type structure refers generally herein to any layered or quasi-layered structure where an active layer is between a first electrode and a second electrode. In some embodiments the actuating elements, the sensing elements, or both will comprise a transistor-type structure. A transistor-type structure refers generally to a structure where the active layer is between two electrodes and atop a gate electrode capable of inducing charge carriers in the active layer. The active layer can be a dielectric material, a semiconductor material, and/or a piezoelectric material. The sensing element can have an output that is linearly proportional to the material property of a range of values. For example, when the material property is the modulus of the material the output of the sensing element can vary linearly over about 1 kPa to 100,000 kPa, about 10 kPa to 100.00 kPa, about 10 kPa to 10,000 kPa, about 10 kPa to 5,000 kPa, about 20 kPa to 4,000 kPa, about 40 kPa to 2,000 kPa, or about 100 kPa to 1,000 kPa. The sensing element can be highly sensitive to slight changes in the material property, for example capable of producing a detectable change in the output signal in response to a change of at least 0.1%, 0.5%, 1%, 2%, 3%, or more of the material property.

The sensing element can also have an output voltage that, under the same conditions, varies reliably and predictably with changes in the actuator voltage and/or changes in the material property. For example, the output voltage can vary linearly over a range of actuator input voltages ranging from about 0.01 to 100 V, about 0.1 to 100 V, about 0.1 to 50 V, about 0.1 to 10 V, about 0.5 to 10 V, or about 1 to 10 V. When the material property is the modulus, the sensing element can have an output that varies linearly over the modulus from about 1 kPa to 100,000 kPa, about 10 kPa to 100.00 kPa, about 10 kPa to 10,000 kPa, about 10 kPa to 5,000 kPa, about 20 kPa to 4,000 kPa, about 40 kPa to 2,000 kPa, or about 100 kPa to 1,000 kPa. In some embodiments the sensing element has an output voltage that is independent of the roughness of the material surface from about 0.01 to 1,000 µm, about 0.1 to 1,000 µm, about 0.1 to 100 µm, about 1 to 100 µm, about 2 to 100 µm, or about 10 to 50 µm.

The sensing elements, actuating elements, or both can have any size suitable for the application and configuration of the elements. In some embodiments the sensing elements have a lateral area that is at least 2, 3, 5, 10, 50, 100, or 500 times smaller than the lateral area of the actuating element. The actuating elements can have a lateral area that is about 10,000 µm$^2$ to 1,000 mm$^2$, about 10,000 µm$^2$ to 100 mm$^2$, about 100,000 µm$^2$ to 100 mm$^2$, about 100,000 µm$^2$ to 50 mm$^2$, about 100,000 µm$^2$ to 10 mm$^2$, about 500,000 µm$^2$ to 10 mm$^2$, or about 1 mm$^2$ to 10 mm$^2$. The sensing elements can be smaller than the actuating elements. In some embodiments the sensing elements has a lateral area that is about 10 µm$^2$ to 100 mm$^2$, about 10 µm$^2$ to 10 mm$^2$, about 100 µm$^2$ to 10 mm$^2$, about 100 µm$^2$ to 1 mm$^2$, about 100 µm$^2$ to 100,000 µm$^2$, about 500 µm$^2$ to 100,000 µm$^2$, about 1,000 µm$^2$ to 100,000 µm$^2$, about 10,000 µm$^2$ to 100,000 µm$^2$, or about 10,000 µm$^2$ to 50,000 µm$^2$.

The actuating elements, the sensing elements, or both can include a piezoelectric material. Suitable piezoelectric materials can include Berlinite ($AlPO4$), Sucrose (table sugar), Quartz, Rochelle salt, Topaz, Tourmaline-group minerals, Gallium orthophosphate ($GaPO_4$), Langasite ($La_3Ga_5SiO_{14}$), Barium titanate ($BaTiO_3$), Lead titanate ($PbTiO_3$), Lead zirconate titanate ($Pb[Zr_xTii^]O_3$, $0<x<1$) (commonly referred to as PZT), Potassium niobate ($KNbO_3$), Lithium niobate ($LiNbO_3$), Lithium tantalate ($LiTaO_3$), Sodium tungstate ($Na2WO_3$), Zinc oxide (ZnO), $Ba_2NaNb_5O5$, $Pb_2KNb_5Oi_5$, Sodium potassium niobate ($(K,Na)NbO_3$) (also known as NKN), Bismuth ferrite ($BiFeO_3$), Sodium niobate ($NaNbO_3$), Bismuth titanate (BUT^On), Sodium bismuth titanate ($Nao.sBio.5TiO_3$), polyvinylidene fluoride (PVDF), poly [(vinylidenefluoride-co-trifluoroethylene] [P(VDF-TrFE)3, or combinations thereof.

The piezoelectric material can have any thickness necessary for the application so long as it is thin enough to maintain the desired level of device flexibility. The piezoelectric material can have a thickness of about 10 nm to 10 µm, about 10 nm to 5 µm, about 50 nm to 5 µm, about 50 nm to 1.5 µm, about 100 nm to 1.5 µm, about 100 nm to 1,000 nm, about 200 nm to 1,000 nm, about 200 nm to 800 nm, or about 300 nm to 800 nm.

Neutral Mechanical Plane

The device can include a neutral mechanical plane. In some embodiments the neutral mechanical plane passes through the piezoelectric material in the sensing elements, in the actuating elements, or both. The neutral mechanical plane is defined mathematically below with respect to FIG. 15. The neutral mechanical plane can be understood as the zero-stress plane within the device when under a bending stress, i.e. the plane through where the stresses within the layers transition between compression and tension when under a bending force. In embodiments where the device contains a plurality of elements having a piezoelectric material, the neutral mechanical plane can pass through the piezoelectric material in each of the elements. If the device is a multi-layer device having a piezoelectric layer, the neutral mechanical plane can be within the piezoelectric layer. In some embodiments, this reduces the strain on the piezoelectric material during bending. For example, in some embodiments the piezoelectric material exhibits a strain of less than 5%, less than 4%, less than 3%, less than 2%, less than 1%, less than 0.5%, less than 0.1%, or less than 0.05% for a bending radius of the device from about 10 mm to 1,000 mm, about 10 mm to 500 mm, about 10 mm to 200 mm, about 20 mm to 200 mm, about 20 mm to 500 mm, about 20 mm to 1,000 mm, about 30 mm to 200 mm, or about 30 mm to 500 mm Electrodes The device can contain one or more electrodes. In some embodiments the device contains a first pair of electrodes in electrical contact with the actuating element, and in some embodiments a second pair of electrodes in electrical contact with the sensing element. The device can contain a plurality of electrodes or electrode pairs, with each in electrical contact with an element or component. For example, each of the sensing elements in a plurality of sensing elements, each of the actuating elements in a plurality of actuating elements, or both can be in electrical contact with a different pair of electrodes, each of which can be individually accessed for independent control of each element in the device. The electrodes can be Ag electrodes, Al, electrodes Au, Co electrodes, Cr electrodes, Cu electrodes, Fe electrodes, Mo electrodes, Nb electrodes, Ni electrodes, W electrodes, Zn electrodes, Zr, Au/Ti electrodes, Cr/Au electrodes, Pt/Cr electrodes, Ti/Au electrodes, Ti/Pt electrodes, or some combination thereof.

Methods of Making the Devices

Methods of making devices for contact sensing and manipulation of material properties are provided. Methods can include making any of the devices described herein. The methods can include a variety of conventional deposition, patterning, and etching techniques known to those skilled in microfabrication. The methods can further include various methods of organic synthesis, for example for synthesis of the elastomeric materials, procedures well known to those skilled in the art of materials synthesis.

Electronic components in the devices such as actuating elements, sensing elements, and the like can generally be made by methods of microfabrication. The methods can include forming the element on a suitable substrate. For example, a sensing element or an actuating elements can be formed on a suitable substrate. Suitable substrates can include semiconducting substrates such as silicon wafers. The substrate can be a transparent substrate such as glass or quartz. The substrate can be a metal oxide substrate.

The methods can include the deposition of one or more layers of a material to form the elements of the device. The deposition techniques can include thermal oxidation of a substrate to form an oxide layer. For example, a silicon oxide layer can be formed by thermal oxidation of a silicon wager substrate. The deposition techniques can include chemical vapor deposition (CVD). The chemical vapor deposition can include, for example, the deposition of a metal electrode material. Many suitable metals can be deposited by CVD using precursors known to those skilled in the art. Aluminum can be deposited from triisobutylaluminium. Titanium can be deposited from the corresponding pentachloride. In some embodiments one or more materials is deposited at moderate pressures of about 1 Torr to 1,000 Torr or about 100 Torr to 800 Torr using metalorganic chemical vapour deposition. In some embodiments the piezoelectric material can be deposited by metalorganic chemical vapour deposition. For example, lead zirconate titanate (PZT) can be deposited by metalorganic chemical vapour deposition. The deposition can also include physical vapor deposition techniques such as sputtering and evaporative deposition methods.

The methods can include patterning methods such as photolithography to pattern one or more layers. For example, the piezoelectric material and/or the electrode can be patterned by photolithography with a suitable photoresist. The layers can be optically patterned with a photoresist material. The suitable photoresist will depend upon the chemical nature of the layer being patterned and the etching technique being used. Such selections are within the capability of those skilled in the art. The photoresist can be a standard photoresist of a curable photoresist. The photoresist can be a positive photoresist or a negative photoresist. The methods can include applying a layer of a photoresist, for example by spin coating the photoresist material. The methods can further include patterning the photoresist with a light source, typically a UV light source. The photoresist can be AZ5214E, AZ4620, or other photoresist available from AZ Electronic Materials.

The methods can include etching of a layer or material to remove all or a portion of a layer. A variety of etching processes are known in the art. The etching can include plasma etching, reactive ion etching, or wet/chemical etching. The layer can have a photoresist patterned to formed structures in the layer during etching. Etchants for various metal electrode materials, for example, are known in the art. The etchants can be, for example, with a gold etchant, a chromium etchant, or the like. The etchant can also include acidic solutions such as hydrochloric acid, nitric acid, hydrofluoric acid, and mixtures thereof.

In some embodiments the actuating element, the sensing element, or both are formed by depositing, patterning and/or etching a top electrode by photolithography; depositing, patterning, and/or etching a piezolelectric layer with a piezoelectric material; and depositing, patterning, or etching of a bottom electrode with an electrode material. The electrode material can include Ag, Al, Au, Co, Cr, Cu, Fe, Mo, Nb, Ni, W, Zn, Zr, Ti, Pt, and combinations thereof. The piezoelectric material can be Berlinite (AlPO4), Sucrose (table sugar), Quartz, Rochelle salt, Topaz, Tourmaline-group minerals, Gallium orthophosphate (GaP0$_4$), Langasite (La$_3$Ga$_5$SiOi$_4$), Barium titanate (BaTi0$_3$), Lead titanate (PbTi0$_3$), Lead zirconate titanate (Pb[Zr$_x$Tii^]0$_3$, 0<x<1) (commonly referred to as PZT), Potassium niobate (KNb0$_3$), Lithium niobate (LiNb0$_3$), Lithium tantalate (LiTa0$_3$), Sodium tungstate (Na2W0$_3$), Zinc oxide (ZnO), Ba$_2$NaNb$_5$05, Pb$_2$KNb$_5$Oi$_5$, Sodium potassium niobate ((K, Na)Nb0$_3$) (also known as NKN), Bismuth ferrite (BiFe0$_3$), Sodium niobate (NaNb0$_3$), Bismuth titanate (BUT^On), Sodium bismuth titanate (Nao.sBio.5Ti0$_3$), polyvinylidene fluoride (PVDF), poly[(vinylidenefluoride-co-trifluoroethylene] [P(VDF-TrFE)3, or a combinations thereof. The elements can be formed on a temporary substrate and the method can include removing or etching away the temporary substrate.

The methods can include depositing a first electrode layer on a substrate; depositing a piezoelectric layer on the first electrode layer; and depositing a second electrode layer on the piezoelectric layer. The methods can include photolithography with a photoresist on the second electrode layer to form a second electrode pattern (top electrode pattern); and etching the second electrode pattern into the second electrode layer to form a second electrode (top electrode). The methods can include photolithography with another photoresist on the piezoelectric layer to form an element pattern; and etching the element pattern into the piezoelectric layer to form the element. The element can be a sensing element, actuating element, or another element. The methods can also include photolithography with another photoresist on the first electrode layer to form a first electrode pattern; and etching the first electrode pattern into the first electrode layer to form a first electrode (bottom electrode). The substrate can be temporary and the methods can include applying a protective photoresist layer and etching away the temporary substrate. The piezoelectric layer can have a thickness of about 10 nm to 10 µm, about 10 nm to 5 µm, about 50 nm to 5 µm, about 50 nm to 1.5 µm, about 100 nm to 1.5 µm, about 100 nm to 1,000 nm, about 200 nm to 1,000 nm, about 200 nm to 800 nm, or about 300 nm to 800 nm.

The methods can include transferring one or more elements to an elastomeric substrate. The transfer can be accomplished using a temporary substrate to transfer the elements, using a transfer tape to transfer the elements, stamping the elements onto the elastomeric substrate, or other variations thereof. The method can include encapsulating one or more of the layers or elements with a protective layer or barrier layer.

Methods of Contact Sensing and Manipulation of Material Properties

Methods are provided for contact sensing and manipulation of material properties using any one of the devices described herein. The methods can include applying the device to a material surface. The material can be any of the materials described above, including a biomaterial, a ceramic, a glass, a metal, a polymer, and combinations thereof. In some embodiments the material surface is a biomaterial surface such as skin, a serosal surface, and organ or organ component surface, and exposed tissue surface (via a surgical or other procedure) or a luminal surface. The surface can be a serosal surface on the surface of an organ examples include but are not limited to heart, a liver, a lung, kidney, brain and GI tract stomach and intestine.

The devices can be formed or semi-formed in vivo or generally at the location and time of placement. For example, the elastomeric substrate can be initially in a fluent or semi-fluent state and then stimulated to render it non-fluent at the location and time of placement. In other implementations, actuating and sensing elements may be positioned on a material (e.g., skin) and an elastomeric material applied over the elements to for an elastomeric substrate that secures the actuating and sensing elements at the location.

The methods can include receiving an output or output signal from a sensing element in the device in response to manipulation of the material. The output or output signal can be utilized to determine a property of the material. The material property can be pH, surface tension, electrical conductivity, hardness, flexural modulus, flexural strength, plasticity, shear modulus, shear strength, Young's modulus, surface roughness, temperature, thermal conductivity, or a combination thereof. The output or output signal can be an output voltage, an output current, an output resistance, or a combination thereof.

The method can include interpreting the output of the device, recording or storing the output signal on the device, transmitting the output signal from the device to a second device, displaying the output signal on the device, or performing a function in response to the output signal. The transmitting can include transmitting the signal or the interpreted results to a second device connected via a wired connection to the device or to a remote device wirelessly. For example, the device can include processing circuitry (e.g., including a processor and memory) that can be configured to control manipulation of the actuating elements and receive the output from the sensor elements. In some embodiments, the processing circuitry can be configured to convert the output of the sensor elements to a digital signal for wireless transmission to a remote user device such as a computer, smartphone, tablet, etc. for further processing and evaluation of the material properties. In other embodiments, the processing signal can be configured to evaluate the output from the sensor elements to determine a material property of the material. The determined property may then be transmitted to the remote user device for access by the user through an interface.

The processing circuitry to can be integrated into the device. For example, the processing circuitry can be miniaturized to reduce the size. Wireless communications between the device and a user device can be provided by a transceiver of the processing circuitry. For example, the transceiver can be configured to support radio frequency (RF) communications using a WiFi, Bluetooth, or other appropriate wireless communication link between the device and the remote user device. The device can include a power source to support the processing circuitry. For example, a battery and power regulation circuitry can be included to supply power. The processing circuitry can be configured to control activation of the actuation element or elements. Activation of the actuation element manipulates the material. Manipulation of the material can generate a variation in the output of the sensing element.

The processing circuitry can include analog-to-digital (A/D) converters configured to convert an analog output of one or more sensing elements to a corresponding digital representation for evaluation and/or transmission of the output information. The processing circuitry can be configured to evaluate the output of sensor elements to determine a property of the material. For example, the processing can determine a condition of the material property based upon a previously determined relationship between the output of the sensor element and the material property. The device can be configured to perform one or more functions in response to the determination. For instance, treatment may be applied to the material to change the material property. The device can also transmit information about the material property to a remote user device for access by the user through an interface on the user device. In other implementations, the output information can be transmitted to a remote user device for processing to determine the material property. Indications of the material property can be provided to the user device for presentation to a user through an interface. In some cases, the user device can communicate a control signal to the device to initiate one or more functions in response to the determination.

The device can perform a function in response to the output or output signal from the sensing element. For example, the device can apply a therapeutic, prophylactic, or diagnostic agent locally to a biochemical tissue. For example, sensing a change in the dryness of a tissue surface, the device may administer an emollient. The device can alert a user in response to a change in an output signal, e.g. signaling a change in a property of a biochemical tissue the device may alert the wearer. This could be used, for example, to alert a diabetic patient to a changing glucose level.

Methods of contact sensing of a material property are provided including (i) applying the device to a surface of a material, (ii) activating one or more actuation element to manipulate the material; (iii) and receiving an output from the sensing element in response to the manipulation of the material. The material can be the skin. The property can be indicative of a physiological state or a change in a physiological state of the material, for example a change in the physiological state of the skin or of the tissue beneath the skin. The physiological state can be the hydration level, the healing progress, or the disease state. For example the disease state can be the level of fibrosis of the tissue or the presence of a lesion in the tissue. For example, the methods can include detection of lesions, e.g. pre-cancerous lesions or diabetic ulcers, before they can be detected using convention methods, e.g. before they can be detected visually. The methods can include following the disease progression and/or the healing progression of a tissue. For example, the disease progression can be the progression of skin fibrosis (or the fibrosis of an internal tissue) in a patient with scleroderma. The healing progression can be the progression of healing in the skin and underlying tissue of a burn patient. The methods can include detecting the progression of fibrosis in any tissue, for example in heart, liver, lungs, intestine, or other soft tissue. The methods can include detecting the disease progression in a patient with endomyocartial fibrosis, atrial fibrosis, cirrhosis, pulmonary fibrosis, cystic fibrosis, Crohn's disease, or other fibrotic diseases and disorders.

In some embodiments the devices can be used on the skin to detect skin or subdermal abnormalities before they are visible or otherwise detectable on the surface of the skin. For example, the devices can be used to detect changes in the material properties of skin in response to a lesion forming under the skin such as are common with skin cancer, an infiltrative process or an infection. The devices can also be used to detect wounds or tissue damage under the skin, for example the formation of diabetic wounds on the foot or ankle of a patient with diabetes.

The material can be a ceramic, a glass, a metal, a polymer, and combinations thereof. For example, the material can be a polymer e.g. a thermoplastic polymer, a thermoset polymer, an elastomer, a rubber, a natural polymer, or a copolymer or combination thereof. The material can be a tube or hose under pressure and the device can be used to monitor failure of the device.

EXPERIMENTAL METHODS AND EXAMPLES

Fabrication of PZT Actuator and Sensor Arrays

Fabrication of the actuator and sensor arrays began with formation of a 500 nm thick film of PZT (INOSTEK) by sol-gel techniques on an oxidized silicon wafer. See, e.g., "Conformal piezoelectric energy harvesting and storage from motions of the heart, lung, and diaphragm" by Dagdeviren et al., *Proc. Natl. Acad. Sci.*, 111, 1927-1932 (2014); and "Conformable amplified lead zirconate titanate sensors with enhanced piezoelectric response for cutaneous pressure monitoring" Dagdeviren et al., *Nat. Commun.*, 5, (2014). See FIGS. 1A-1G. The actuator layers included a 260×1300 $\mu m^2$ bottom electrode (Pt/Ti; 300 nm/20 nm), a 200×1000 $\mu m^2$ PZT layer, and 140×940 $\mu m^2$ top electrode (Au/Cr; 200 nm/10 nm). The sensor layers included a 160×660 $\mu m^2$ bottom electrode (Pt/Ti; 300 nm/20 nm), 100×500 $\mu m^2$ PZT layer, and 60×460 $\mu m^2$ top electrode (Au/Cr; 200 nm/10 nm). Photolithography with standard photoresist (PR, AZ5214E) defined the top Au/Cr electrode structure. The Au and Cr layers were etched with gold etchant (TFA, Transene Company Inc., USA) and CR-7 chrome etchant (OM Group, USA), respectively. Wet chemical etching with a solution of $HNO_3$:$BHF$:$H_2O$ (Nitric acid:Buffered Hydrofluoric Acid: DI water ratio of 4.51:4.55:90.95) through a hard baked (80° C. for 5 min, 110° C. for 30 min and 80° C. for 5 min) mask of photoresist (PR) (AZ4620, Clariant) defined a corresponding pattern in the PZT See FIG. 2B. Etching with a solution of $HCl$:$HNO_3$:$H_2O$ (DI water)=3:1:4 at 95° C. and a similar PR mask (See FIG. 2E) patterned the bottom Pt/Ti electrode structure. Another hard-baked PR mask protected the PZT during elimination of the underlying $SiO_2$ layer with diluted hydrofluoric acid ($H_2O$:49% HF=1:3 by volume). Immersion in an acetone bath at room temperature for ~3 h washed away the PR (See FIG. 1B).

Figures 2A, 2B, 2C, 2D, 2E, 2F, 2G, 2H, 2I, 2J, 2K, 2L:
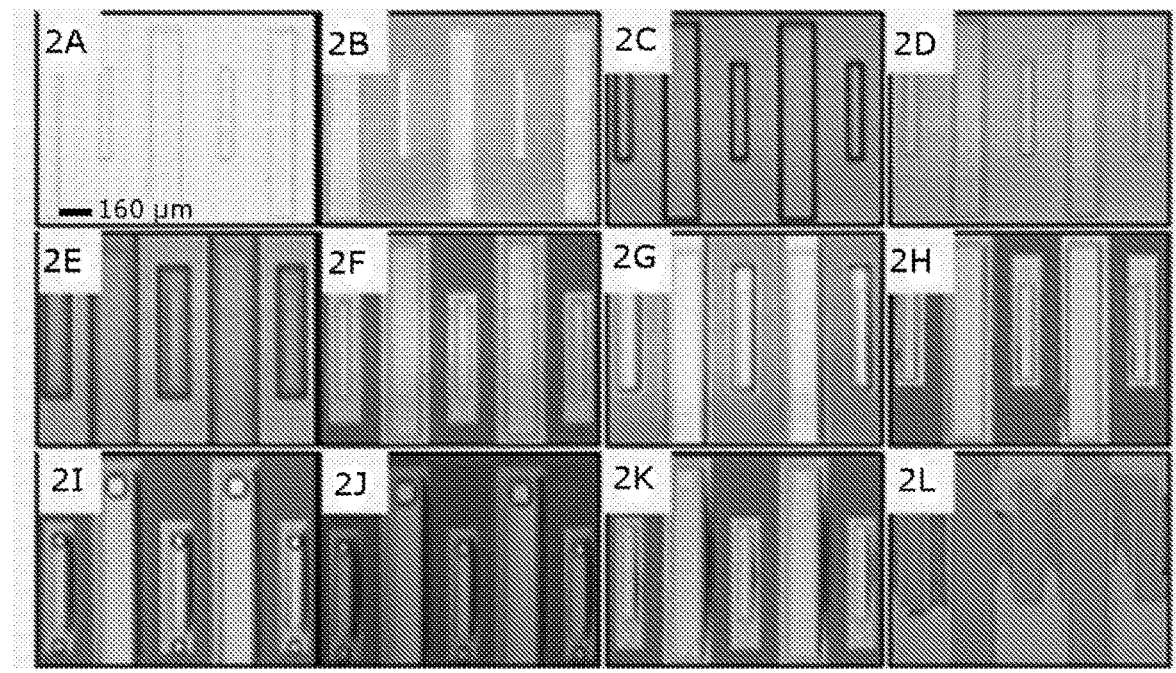
FIGS. 2A-2P are optical micrographs of various structures at various stages of fabricating the CMS systems.
FIG. 2B is an optical microscope image of a pattern of Au formed by etching.
FIG. 2C is an optical microscope image of a photoresist patterned for etching the underlying layer of PZT.
FIG. 2D is an optical microscope image of a PZT layer after selective etching.
FIG. 2E is an optical microscope image of a photoresist patterned for etching the underlying layer of Pt.
FIG. 2F is an optical microscope image of a Pt layer after selective etching.
FIG. 2G is an optical microscope image of a photoresist patterned for undercutting the $SiO_2$ layer with diluted HF.
FIG. 2H is an optical microscope image of a structure after etching with HF.
FIG. 2I is an optical microscope image of a photoresist patterned for defining contact holes through the polyimide (PI).
FIG. 2J is an optical microscope image of a pattern after etching the PI.
FIG. 2K is an optical microscope image of a PZT sensor and actuator arrays on a temporary substrate.
FIG. 2L is an optical microscope image of the remaining materials on the temporary substrate after retrieving the arrays with a PDMS stamp.
Figure 2M:
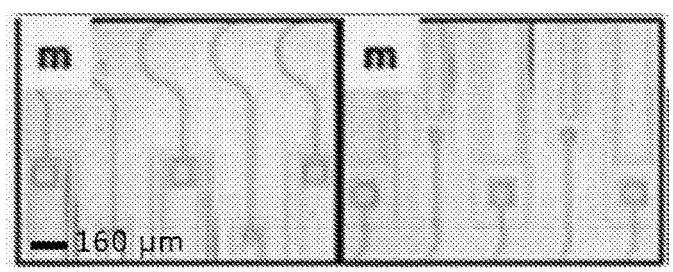
FIG. 2M is an optical microscope image of a photoresist patterned on Au to define serpentine interconnections to the arrays.
Figure 2N:
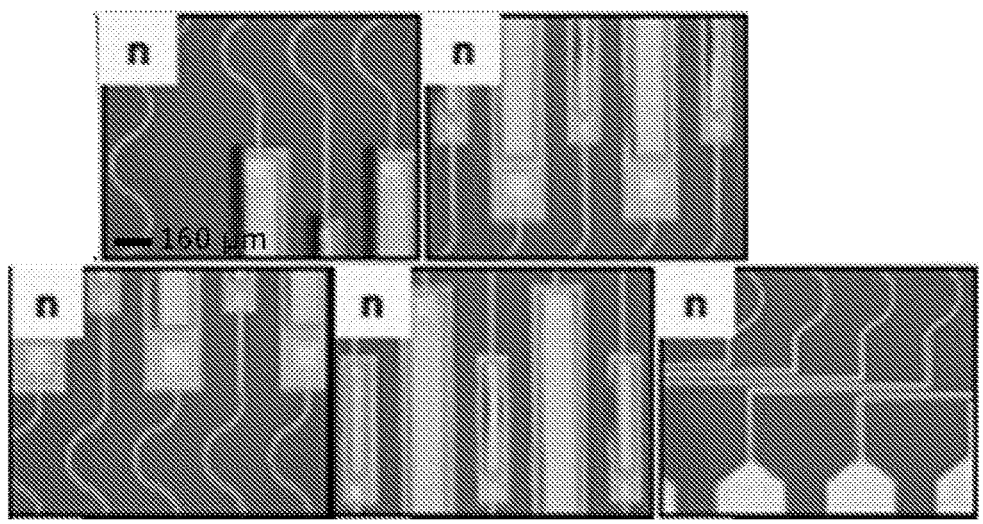
FIG. 2N are optical microscope images of a serpentine interconnections formed by etching the Au.
Figure 2O:
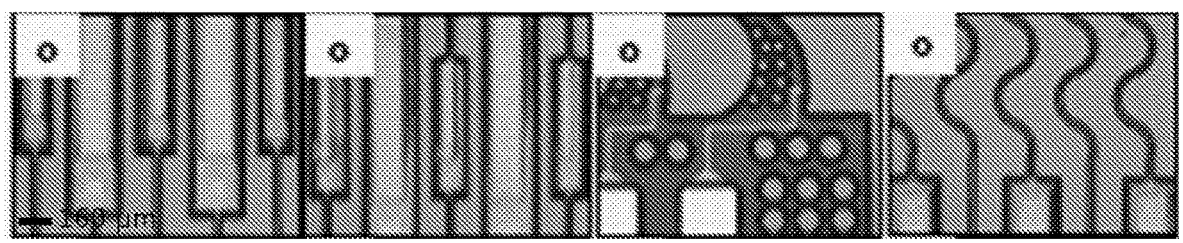
FIG. 2O are optical microscope images of a photoresist patterned mask for defining the PI encapsulation.
Figure 2P:
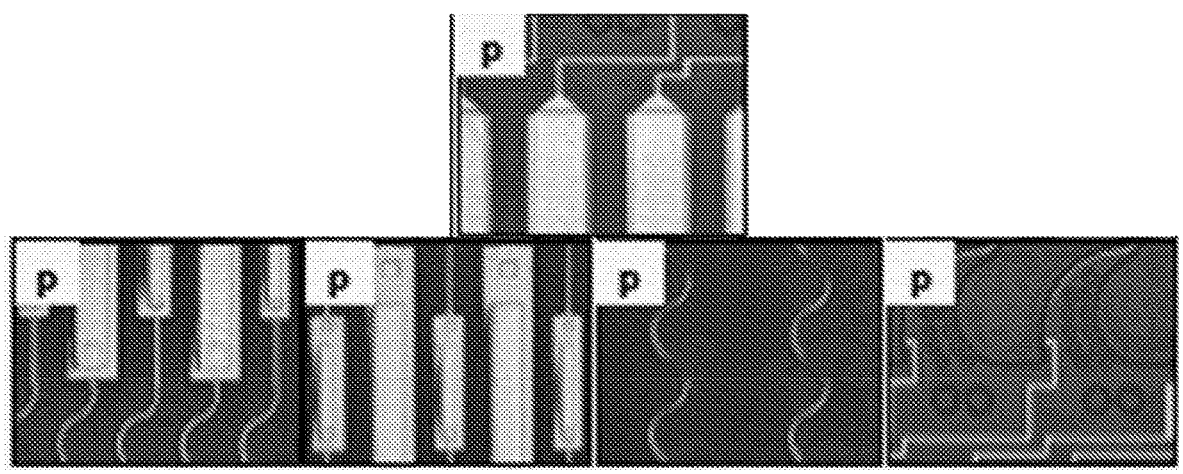

Application and removal of a piece of thermal tape (REVALPHA, Nitto Denko) retrieved the PZT devices from the silicon wafer (See FIG. 1C). A separate wafer coated with a 50 nm thick layer of poly(methyl methacrylate) (PMMA 495 A2, 3,000 rpm. for 30 sec, baked on a hotplate at 180° C. for 2 min) and a 1.2 µm thick layer of PI (from poly(pyromellitic dianhydride-co-4,40-oxydianiline)amic acid solution; 4,000 rpm. for 30 sec, pre-cured on a hotplate at 150° C. for 1 min) served as a temporary substrate. Heating at 250° C. for 1 min partially cured the PI to provide a tacky surface. Transfer (See FIG. 1D) occurred by laminating the tape with PZT devices onto this substrate, heating to ~150° C. (on hot plate) and then removing the tape. Baking at 250° C. for 1 h in a vacuum oven at 10 mT completed the curing of the PI.

A uniform 1.2 µm thick layer of PI was spin cast and cured (250° C. for 1 h) on the PZT devices protected their top surfaces. Openings through the PI formed by reactive ion etching (March RIE) through a pattern of PR provided access to the metal electrode contacts (See FIGS. 2I and 2J). Evaporation and photolithographic patterning of Au/Cr (200 nm/10 nm) defined metal interconnects. Another patterned 1.2 µm thick PI layer was formed an encapsulation layer that left the PMMA layer exposed for removal by immersion in acetone at 100° C. (See FIG. 1E). Thermal tape again served a vehicle for retrieving the devices (See FIG. 1F). A layer of Ti/$SiO_2$ (4 nm/40 nm) evaporated onto the exposed backside of the devices provided an adhesive layer for bonding onto a 20 µm thick film of silicone (Ecoflex 00-30, SMOOTH-ON; weight ratio of 1A:1B) on a substrate of poly(vinylalcohol) (PVA; A-30031, Best Triumph Industrial Ltd) temporarily held to a glass slide by a layer of polydimethylsiloxane (PDMS, Sylgard 184). Transfer from the thermal tape used procedures similar to those described previously (See FIG. 1G). The mounting process involved placing the PZT sensor and actuator arrays against the skin and then gently washing away the PVA with water.

Directional Modulus Mapping

A sensor was aligned to a protractor, e.g. with a 2 cm radius (R) printed on a transparent film (AF4300, 3M) and mounted in a rotatable fashion to serve as a tool for directional modulus mapping. The CMS was rotated clockwise (C) or anti-clockwise (A) with an angle increment of 15°. The distance, w, between the center of protractor and the edge of the first sensor in the array defined the mapping area. A 3M Tegaderm™ Film laminated on the top surface prevented motion during measurement.

Confocal Microscopy

Imaging through the depth of skin involved a Leica SP2 Visible Laser Confocal Microscope (oil immersion, numerical aperture 1.40, lateral optical resolution 240 nm) with a 63× objective and 633 nm laser illumination. Glass slides (170 µm thick) served as supports for the skin samples. Three-dimensional (3D) reconstruction used standard software tools (Amira Software 5.0.2). The detection bandwidth (±10 nm) and gain were fixed for all samples, to facilitate comparisons. Human skin has autofluorescence due to collagen structure, thus no fluorophore was needed.

Poling the PZT

Poling involved application of an electric field (~100 kV/cm) at 150° C. for 2 h to PZT thin films between bottom and top contacts of Ti/Pt (20 nm/300 nm) and Cr/Au (10 nm/200 nm), respectively.

Device Operation

A recording system having a lock-in amplifier (SR830, Standard Research Systems, USA), a multiplexer (FixYourBoard.com, U802, USA), and a laptop computer enabled collection of data from the sensors and application of driving voltages to the actuators. A flexible ribbon cable (HST-9805-210, Elform, USA) connected arrays of six sensors to a multiplexer, for sequential interrogation.

Preparation of Artificial Skin Samples

Artificial skin samples consisted of a mixture of commercially available materials: Dragon Skin (Dragon Skin® 30, Smooth-On, Inc), Silc Pig (Silc Pig, Flesh tone silicone pigment, Smooth-On, Inc) and Ecoflex (Eco Flex® 30, Smooth-On, Inc). The Dragon Skin (1:1 weight ratio of part A and part B) was mixed with Silc Pig (3% by weight) and then placed on the forearm of a male volunteer where it was allowed to cure under ambient conditions for ~1 h. Removing the material and placing it in a plastic petri dish with the textured side up allowed it to be used as a mold. Ecoflex (1:1 weight ratio of A:B) was then mixed with Silc Pig (3% by weight), placed in a vacuum chamber for 0.5 h, and then poured on the top of the Dragon Skin sample. Peeling the cured material away after curing for 12 h at room temperature yielded samples of artificial skin.

Scanning Electron Microscopy and Image Preparation

Scanning electron microscopy (HITACHI S-4800) provided images of devices mounted on artificial skin. The colorization process used the color burn function in Adobe Photoshop CS6, with the following RGB values for the different layers: Gold (218, 165, 32), PZT (57, 206, 72), PI (243. 111. 39), Skin (190, 142, 122).

Nanoindentation

Skin embedded in epoxy resin was cut in 100 nm sections using a Leica UC-6 ultra-microtome (Wetzlar, Germany), leaving a polished surface for indentation testing. Testing occurred at 45%+/−5% humidity and 20° C., with a Tribo- Scope nanoindenter (Hysitron, Minneapolis, Minn.) mounted on a Multimode atomic force microscope (AFM) controlled by NanoScope IIIa electronics (Veeco, Santa Barbara, Calif.). The tip radius determined by examination with an SEM agreed (within 90%) with this calibrated value. A force with a trapezoidal time profile applied to the skin surface generated a load-displacement curve that allowed quantitation of elastic modulus and hardness. Consecutive measurements were separated by 2 μm to minimize the influence of prior indentations.

Dynamic Mechanical Analysis

Figure 11:
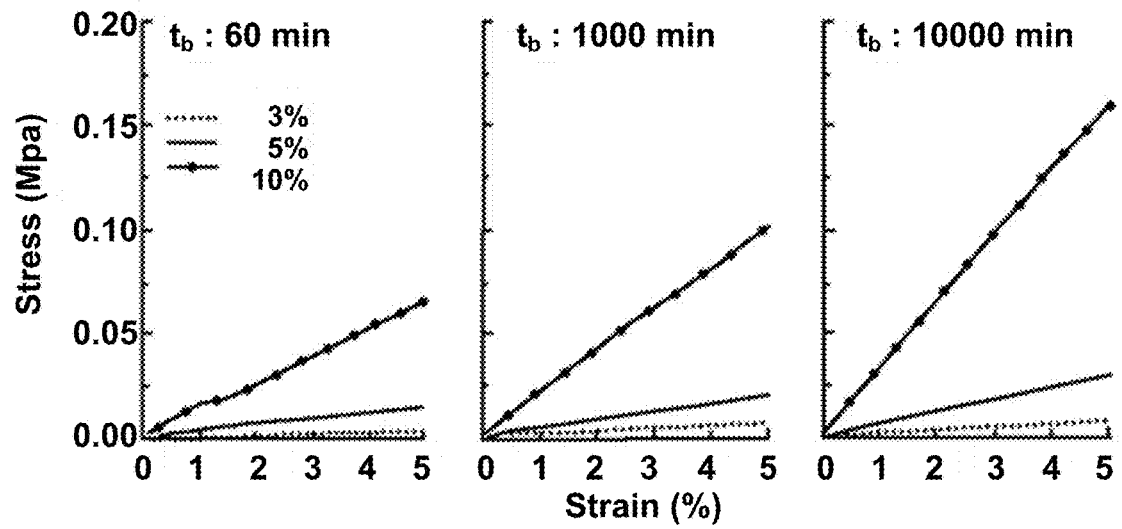
FIG. 11 depicts the stress-strain responses measured by quasi-static dynamic mechanical analysis of various formulations of PDMS. Measurement results are for different amounts of crosslinker, by weight (pink: 3%, green: 5%, blue: 10%) cured at 70° C. for 60, 1000, and 10,000 minutes (from left to right).

Dynamic mechanical analysis (Q800 DMA, TA Instruments) allowed measurement of quasi-static stress-strain curves of a set of substrates of polydimethylsiloxane (PDMS, Sylgard 184, Dow Corning) formed using different conditions to yield a range of Young"s moduli (See FIG. 11). Each PDMS substrates had dimensions of 3.5×6.0×2.0 mm3 (width×length×thickness). The measurements used the DMA film tension clamp in ambient conditions, with a strain rate of 10%/min to a maximum value of 100%.

In Vitro Biocompatibility Assessment

Experiments involved human epithelial keratinocytes (HEK) purchased from Life Technologies (HEKa; Grand Island, N.Y., USA), cultured in T-75 tissue culture flasks with Medium 154 medium (Life Technologies) supplemented with Human Keratinocyte Growth Supplement (Life Technologies) and 1% Pen/Strep Amphotericin B (Lonza, Allendale, N.J., USA). The complete culture medium was stored at 4° C. for use within 4 weeks from the time of preparation. HEK cells were sub-cultivated and cultured in an incubator for all studies (37° C., 5% $CO_2$, and 95% relative humidity). Cell utilized for seeding on the sensor surface were passage 2-5 before seeding on sensor surface. The biocompatibility studies involved seeding HEK (~20,000) onto strips of sensor devices (1 cm$^2$ pieces, sterilized under UV light for 30 min on each side) and incubating them for 1 or 3 days as outlined above, with medium change every 48 h. On day 1, cells were stained using an actin cytoskeleton/focal adhesion staining kit (Millipore, Mass., USA). Cells were fixed with 4% paraformaldehyde for 15 min, washed, then, permeabilzed with 0.05% Triton-X for 5 min, washed and then blocked with 1% protein standard (fractionated bovine serum albumin) in PBS at pH 7.4. Cells were then incubated with tetramethyl rhodamine isothicyanate (TRITC) conjugated Phalloidin for 1 h to selectively label F-actin. After rinsing, cells were then mounted in a vector shield with DAPI (Sigma-Aldrich, St. Louis, Mich., USA) and imaged using a Nikon C1Si Laser Scanning Confocal Fluorescence Microscope. Optical micrographs showing Actin and DAPI staining of HEK on a device following 24 hours of culture and Live/Dead staining were examined to determined adherence and toxicity.

Scanning electron microscopy (SEM, FEI Inspec S, Thermo, Rockford, Ill., USA) revealed the extent of adherence of cells to the sensor substrates. For this purpose, following 24 hrs of culture HEK were fixed in 5% Glutaraldehyde in PBS, pH 7.4, subjected to a graded series of water and ethanol (100% fixator → 3:1 → 1:1 → 1:3 → 100% Distilled water → 3:1 → 1:1 → 1:3 → 100% Ethanol) at 5 min for each step and then critical point dried (Polaron model 3100, Energy Beam Sciences). Specimens were then mounted on aluminum stubs, sputter-coated with gold (5-8 nm, Hummer Sputtering System, Anatech, Hayward, Calif., USA) and imaged at voltages between 5 and 15 kV with an aperture spot size of 3. The viability, proliferation, and cytotoxicity of HEK were determined by a two-color fluorescence LIVE/DEAD viability (Invitrogen) assay, Lactate Dehydrogenase (LDH) assay (Thermo, IL, USA), and MTT assay. For the LIVE/DEAD assay, HEK grown on sensor strips for 1 day were prepared and stained according to standard protocols (Sigma Aldrich, St. Louis, Mo., USA). Briefly, culture dish wells were aspirated, washed and a working solution (containing 5 mL 1×PBS, 10 μl of 2 mM EthD-1, and 2.5 μl of 4 mM Calcein AM) was then added to cover each of the samples. Submerged samples were incubated for 30 minutes at 37° C. The working solution was then removed, and the samples were rinsed once with 1×PBS, then mounted in Flouroshield and immediately imaged by fluorescence microscopy (Nikon C1Si).

The LDH cytotoxicity assay involved mixing 50 μl medium from HEK grown for 1 and 3 days with a 50 μl reaction mixture (prepared according to the manufacture"s recipe) in a 96 wells plate and incubating for 30 min at room temperature. A stop solution (50 μl) was then added and the optical absorbance was immediately measured at 490 and 680 nm. The mean percent of healthy cells were reported with standard errors of the mean. For the MTT assay, 100 μl of a 5 mg/mL solution of thiazol blue tetrazolium bromide (Alfa Aesar, Ward Hill, Mass.) was added to cells in a 24-well plate. After 3.5 h of incubation at 37° C., 5% $CO_2$, and 95% relative humidity, the well contents were removed and 300 μl of dimethyl sulfoxide was added to each well. The well plate was rocked slowly for 10 min and the contents of each well were then transferred to a 96 well plate where the absorbance was determined at 590 nm and 620 nm. True absorbance was calculated by subtracting the 590 nm reading from the one at 620 nm. As a positive control, 5% SDS was added to cells seeded in control tissue culture plate wells 1 h prior to removal of the tiazol blue terazolium bromide and the cell media from some of the wells. All readings were compared to cells seeded in 24 well plates on the tissue culture surface. Results correspond to the percentage absorbance compared to the values of the tissue culture plates. To demonstrate feasibility for external placement, temporary use, and to ensure that there was no alteration in the functional groups on the surfaces of the sensors after cultured with cells and submerged in cell media for 7 days, attenuated total reflectance-Fourier transform infrared spectroscopy (ATR-FTIR) (Thermo Nicolet 370-FT-IR, Thermo Scientific, Waltham, Mass., USA) was utilized to obtain the infrared transmittance before and after the sensors had been cultured with HEK. The spectrum was collected with 32 points. The ATR-FTIR collected on the device before and after 7 days incubation with cells exhibit no significant change.

Ex Vivo Modulus (Material Property) Assessment

Freshly excised bovine hearts and lungs (n=3) were utilized for determination of regional material properties using the piezoconstructs. The heart was selected as a prototypic solid organ as differing regions have clear material property differences based on differing histoarchitecture, variable thickness and perfusion. Further the curvilinearity and complex geometry served as a stringent test for the efficacy of the constructs. Constructs were laminated on the LV, RV, apex sites of the hearts and the surface of lung. The intimate integration between curly, soft tissue and conformal constructs on silicone substrate was driven by van der Waals forces alone, without application of adhesive layer, thereby leading to a conformal, precise, completely noninvasive measurement. All animal studies were approved by the Institutional Animal Care and Use Committee at the University of Arizona.

In Vivo Modulus (Material Property) Assessment

Forty human volunteers were utilized for the described studies. Ten volunteers were (5 female, 5 male) were recruited for studies on normal skin, with all of these free of visible skin lesions. Thirty patients with a range of dermatologic conditions (15 female, 15 male) including: fibrous histiocytoma, lichenoid keratosis, seborrheic keratosis, actinic keratosis, squamous cell carcinoma, basal cell carcinoma, compound nevus, hemangioma, fibroepithelial polyp, superficial perivascular & interface lymphocytic dermatitis, erosive dermatitis, severely atypical compound melanocytic proliferation, and bullous pemphigoid were studied, as seen in FIGS. 5A-5E, 6A-6E, and 7A-7D. All subjects (normals and patients) were volunteers for this study, were informed of risks and benefits and provided informed consent.

Neutral Mechanical Plane and Bending Stiffness

For the multilayer structure with n layers subjected to pure bending, the cross-section remains planar after bending in the classical beam theory. The neutral mechanical plane, located by the distance $y_{neutral}$ from the bottom surface of the multilayer structure (FIG. 15) is given by:[1]

$$\overline{EI} = \sum_{k=1}^{n} \overline{E}_k h_k \left[ \left( y_{neutral} - \sum_{j=1}^{k} h_j \right)^2 + \left( y_{neutral} - \sum_{j=1}^{k} h_j \right) h_k + \frac{1}{3} h_k^2 \right]. \quad (S2)$$

where $\overline{E}_k = E_k/(1-v_k^2)$ and $h_k$ are the plane-strain modulus and thickness of the $k^{th}$ layer, respectively, with k=1 for the bottom layer. The bending stiffness of the structure is given by:

$$y_{neutral} = \frac{\sum_{k=1}^{n} \overline{E}_k h_k \left( \sum_{j=1}^{k} h_j - \frac{h_k}{2} \right)}{\sum_{k=1}^{n} \overline{E}_k h_k}, \quad (S1)$$

Figure 15:
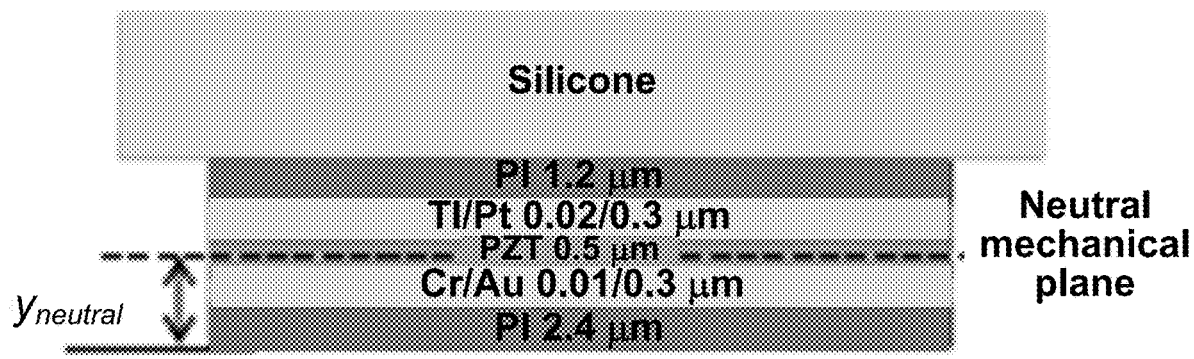
FIG. 15 is a schematic cross sectional illustration of the layout of the sensors/actuators in one CMS device, with the location of the neutral mechanical plane highlighted.
Figure 26:
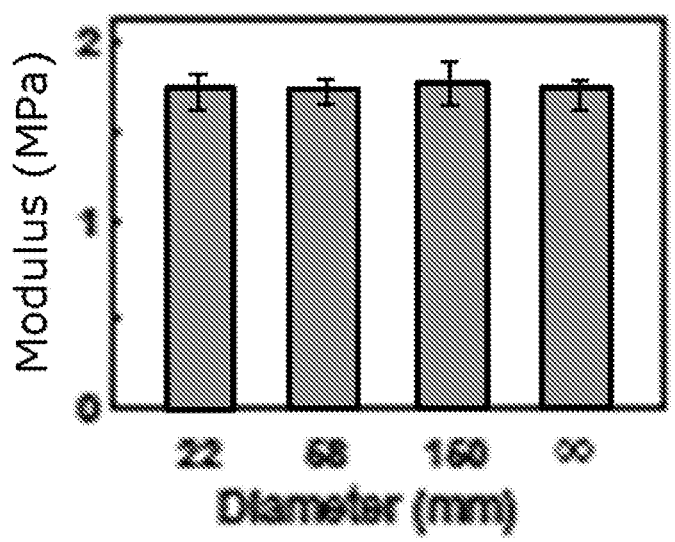
FIG. 26 is a graph of sensor voltage and computed modulus values for PDMS substrate (E=1800 kPa) with various diameters demonstrating the effects of bending on the PZT CMS measurement with on cylindrical substrates having a diameter of curvature of 22 mm, 59 mm, 150 mm, and ∞, respectively.

For the structure in FIG. 15, the Young's modulus of elastomer substrate (silicone, 60 kPa) is much smaller than those of the other layers of the device by 5 to 7 orders of magnitude. The elastomer layer has a negligible effect on the effective bending stiffness and the neutral mechanical plane of the cross section. For the thickness given in FIG. 15 and the plane-strain modulus of PI ($\overline{E}_1 = \overline{E}_7 = 2.83$ GPa), Au ($\overline{E}_2 = 96.7$ GPa), Cr ($\overline{E}_3 = 292$ GPa), PZT ($\overline{E}_4 = 42.1$ GPa), Pt ($\overline{E}_5 = 196$ GPa) and Ti ($\overline{E}_6 = 124$ GPa), the neutral mechanical plane is at $y_{neutral} = 2.99$ μm, which is located around the middle of the PZT layer. The corresponding bending stiffness is $\overline{EI} = 4.55 \times 10^{-8}$ Nm. The location of the neutral mechanical plane layout with respect to the PZT is important. For the bending radius varying from 22 mm to 150 mm (22 mm, 58 mm, 150 mm) in FIG. 26, the corresponding strain in PZT layer is less than 0.002%, which is negligible as compared to the strain field induced by voltage. The results have been validated by the output voltage of the sensors (FIG. 26). Therefore, the sensor voltages are almost the same when laminated on the flat and curvature surfaces.

Piezoelectric Analysis

The constitutive model of piezoelectric material gives:

$$\begin{Bmatrix} \sigma_{11} \\ \sigma_{22} \\ \sigma_{33} \\ \sigma_{23} \\ \sigma_{31} \\ \sigma_{12} \end{Bmatrix} = \begin{pmatrix} c_{11} & c_{12} & c_{13} & 0 & 0 & 0 \\ c_{12} & c_{11} & c_{13} & 0 & 0 & 0 \\ c_{13} & c_{13} & c_{33} & 0 & 0 & 0 \\ 0 & 0 & 0 & c_{44} & 0 & 0 \\ 0 & 0 & 0 & 0 & c_{44} & 0 \\ 0 & 0 & 0 & 0 & 0 & (c_{11}-c_{12})/2 \end{pmatrix} \begin{Bmatrix} \varepsilon_{11} \\ \varepsilon_{22} \\ \varepsilon_{33} \\ 2\varepsilon_{23} \\ 2\varepsilon_{31} \\ 2\varepsilon_{12} \end{Bmatrix} - \begin{Bmatrix} 0 & 0 & e_{31} \\ 0 & 0 & e_{31} \\ 0 & 0 & e_{33} \\ 0 & e_{15} & 0 \\ e_{15} & 0 & 0 \\ 0 & 0 & 0 \end{Bmatrix} \begin{Bmatrix} E_1 \\ E_2 \\ E_3 \end{Bmatrix}, \quad (S3)$$

$$\begin{Bmatrix} D_1 \\ D_2 \\ D_3 \end{Bmatrix} = \begin{pmatrix} 0 & 0 & 0 & 0 & e_{15} & 0 \\ 0 & 0 & 0 & e_{15} & 0 & 0 \\ e_{31} & e_{31} & e_{33} & 0 & 0 & 0 \end{pmatrix} \begin{Bmatrix} \varepsilon_{11} \\ \varepsilon_{22} \\ \varepsilon_{33} \\ 2\varepsilon_{23} \\ 2\varepsilon_{31} \\ 2\varepsilon_{12} \end{Bmatrix} - \begin{pmatrix} k_{11} & 0 & 0 \\ 0 & k_{22} & 0 \\ 0 & 0 & k_{33} \end{pmatrix} \begin{Bmatrix} E_1 \\ E_2 \\ E_3 \end{Bmatrix}, \quad (S4)$$

where $\sigma_{ij}$, $\varepsilon_{ij}$, $E_i$, $D_i$ represent the stress, strain, electrical field and electrical displacement, respectively, and $c_{ij}$, $e_{ij}$, $k_{ij}$ are the elastic, piezoelectric and dielectric parameters of the material. The subscript "3" denotes the polarization (vertical, FIG. 15) direction of the PZT layer.

When subjected to the actuator voltage $U_A$, the electric field intensity in polarization direction is $E_3 = U_A/h_{PZT}$, where $h_{PZT}$ is the thickness of the PZT layer. For plane-strain deformation $\varepsilon_{22} = \varepsilon_{12} = \varepsilon_{23} = 0$, electric field boundary condition $E_1 = E_2 = 0$ and the approximate traction-free condition $\sigma_{33} = 0$ (by neglecting the traction from the softer substrate), equation (S3) gives:

$$\begin{cases} \sigma_{11} = \frac{(c_{11}c_{33} - c_{13}^2)\varepsilon_{11} + (c_{13}e_{33} - c_{33}e_{31})E_3}{c_{33}} \\ \sigma_{22} = \frac{(c_{12}c_{33} - c_{13}^2)\varepsilon_{11} + (c_{13}e_{33} - c_{33}e_{31})E_3}{c_{33}} \\ \varepsilon_{33} = \frac{e_{33}E_3 - c_{13}\varepsilon_{11}}{c_{33}} \end{cases} \quad (S5)$$

Under bending the strain $\varepsilon_{11}$ can be written as $\varepsilon_{11} = \kappa z + \varepsilon_{11}^0$, where the curvature $\kappa$ and membrane strain $\varepsilon_{11}^0$ are determined by the requirement of vanishing membrane force and bending moment, i.e., $$\sum_{k}^{n} F_k = \sum_{k}^{n} \int_{h_k} \overline{E}_k \varepsilon_{11} dz = 0, \quad \sum_{k}^{n} M_k = \sum_{k}^{n} \int_{h_k} \overline{E}_k \varepsilon_{11} z dz = 0. \quad (S6)$$

The normal strain along polarization direction in the $k^{th}$ layer can be expressed as $$\varepsilon_{33} = -v'_k \varepsilon_{11}, \quad (S7)$$

where $v'_k=v_k/(1-v_k)$ is the plane-strain Possion's ratio of the $k^{th}$ layer. The expansion of the actuator, $\Delta u=\beta_1 \cdot U_A \cdot e_{33}/c_{33}$ (equation (2)), is obtained by the integration of $\varepsilon_{33}$, where the dimensionless parameter $\beta_1$ depends on the material and thickness of the multilayer structure discussed above, and $\beta_1=1.420\times 10^5$ for the material and dimensions in FIG. 15.

Interfacial Crack and Sensor Output Voltage

Figure 10A:
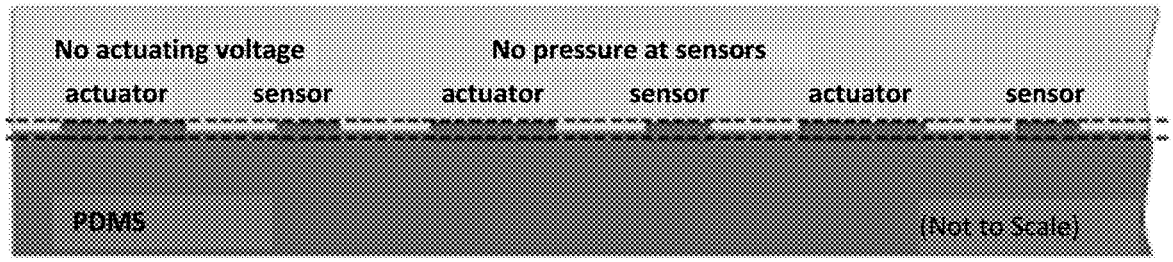
FIGS. 10A-10C depict schematic cross sectional illustrations of mechanics principles associated with theoretical modeling of the device physics.
Figure 10B:
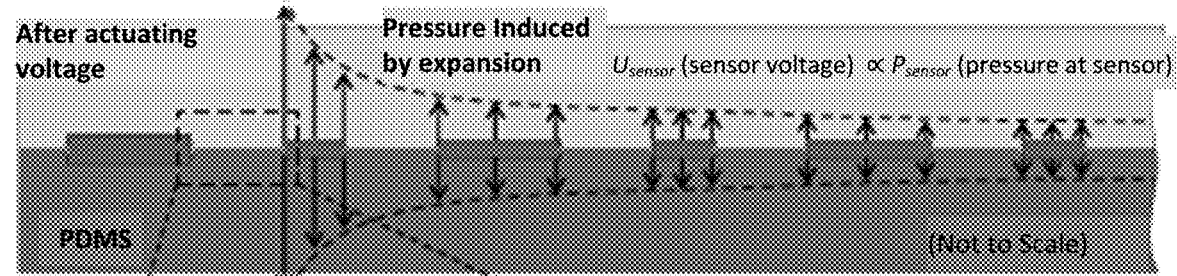
Figure 10C:
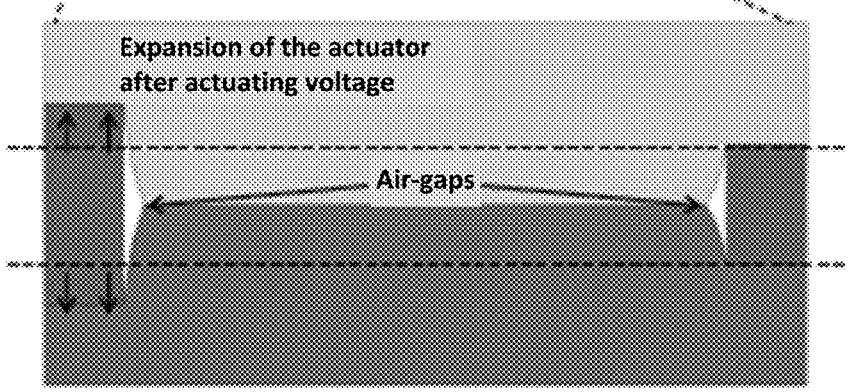
Figure 29:
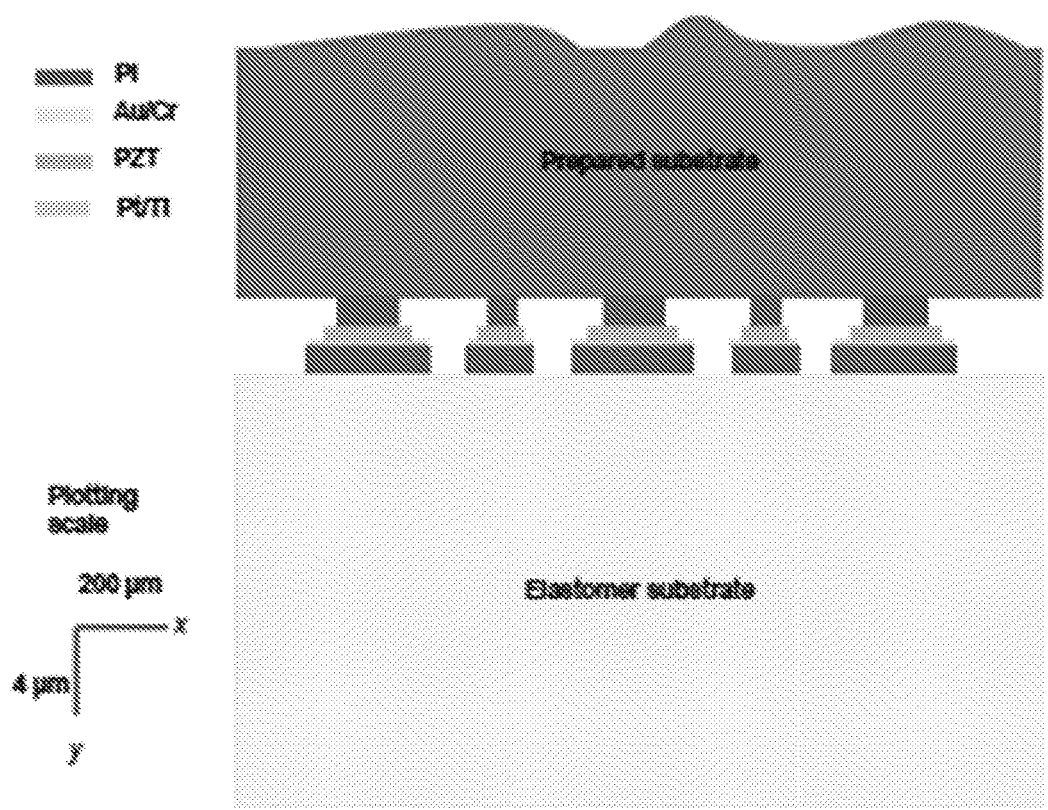
FIG. 29 is a cross-sectional illustration of the multi-layer structure of the sensors/actuators, for the condition that the elastomer layer and prepared substrate do not adhere. As depicted, the plotting scales in the vertical and horizontal directions are different.

As shown in FIG. 10C, the air-gaps form at each terminal of the PZT actuator/sensor after the contact of the elastomer and prepared substrate. The actuator/sensor with two terminals can be modeled as an interfacial crack, and all the cracks are collinear. The displacement boundary conditions are given in the main text (equation (1)). As mentioned in the "Methods" section, the actuators and sensors consist of elastomer substrate (silicone)/bottom encapsulation (PI)/bottom electrodes/PZT/top electrodes/top encapsulation (PI) (FIG. 29). The area of the bottom encapsulation is about 2.5 times as large as that of the top encapsulation. Therefore the effective modulus of the elastomer layer is much larger than that of the prepared substrate, and does not appear in the analysis according to interfacial fracture mechanics[2].

The collinear interfacial cracks with the boundary conditions are solved analytically by approximating the stress over each actuator/sensor by its average stress. This gives the average stress on the $i^{th}$ sensor, $p_{S,i}=\eta_i \cdot \Delta u \cdot E_{P.S}/2a$ (equation (3) in the main text), where the parameter $\eta_i$ is dimensionless, and $\eta_1=1.072\times 10^{-2}$, $\eta_2=3.098\times 10^{-3}$, $\eta_3=1.114\times 10^{-3}$, $\eta_4=5.683\times 10^{-4}$, $\eta_5=3.437\times 10^{-4}$ and $\eta_6=2.300\times 10^{-4}$ for the positions in FIG. 1D. For the pressure $p_{S,i}$ on the $i^{th}$ sensor and the stress and electric displacement fields $\sigma_{33}^i=p_{S,i}$ and $D_3^i=0$ (where the superscript "i" denotes the $i^{th}$ sensor), equations (S3) and (S4) give:

$$\begin{cases} \sigma_{11}^i = c_{11}\varepsilon_{11}^i + c_{13}\varepsilon_{33}^i - e_{31}E_3^i \\ p_{S,i} = c_{13}\varepsilon_{11}^i + c_{33}\varepsilon_{33}^i - e_{33}E_3^i \\ 0 = e_{31}\varepsilon_{11}^i + e_{33}\varepsilon_{33}^i + k_{33}E_3^i \end{cases} \quad (S8)$$

Similar to above, the strain $\varepsilon_{11}^i$ can be written as $\varepsilon_{11}^i=\kappa_i z+(\varepsilon_{11}^0)_i$, where the curvature $\kappa_i$ and membrane strain $(\varepsilon_{11}^0)_i$ are determined by the requirement of vanishing membrane force and bending moment in equation (S6). Equation (S8) then give the strains ($\varepsilon_{11}^i$ and $\varepsilon_{33}^i$) and the electric field intensity ($\varepsilon_3^i$). The output voltage of the $i^{th}$ sensor is obtained in the main text as $U_{S,i}=\beta_2 \cdot p_{S,i} \cdot h_{PZT}/e_{33}$ (equation (4)), where the dimensionless parameter $\beta_2$ depends on the material and geometry of the multilayer structure, and $\beta_2=3.467\times 10^{-3}$ for the material and dimensions in FIG. 15. For plane-strain deformation $\varepsilon_{22}=\varepsilon_{12}=\varepsilon_{23}=0$ and $\sigma_{33}^i=p_{S,i}$ (in the $k^{th}$ layer), the normal strain along polarization direction in the $k^{th}$ layer can be expressed as $(\varepsilon_{33}^i)=[1-(v'_k)^2]p_{S,i}/\overline{E}_k-v'_k\varepsilon_{11}^i$, where $\overline{E}_k$ and $v'_k$ are plane-strain modulus and Possion's ratio, respectively (see above). The expansion $\Delta u_{S,i}$ of the $i^{th}$ sensor is obtained by integrating of $(\varepsilon_{33}^i)_k$ as:

$$\Delta u_{S,i} = \zeta_i \frac{e_{33}}{c_{33}} U_A, \quad (S9)$$

where the parameter $\zeta_i$ is dimensionless, and $\zeta_1=-2.135\times 10^{-2}$, $\zeta_2=-6.172\times 10^{-3}$, $\zeta_3=-2.220\times 10^{-3}$, $\zeta_4=-1.132\times 10^{-3}$, $\zeta_5=-6.849\times 10^{-4}$ and $\zeta_6=-4.583\times 10^{-4}$ for the positions in FIG. 1F. From equation (2) (in the main text) and equation (S9), the ratio of expansion of the active actuator to that of any other sensors is in the range $|\Delta u/\Delta u_{S,i}|=|\beta_1/\zeta_i|=6.651\times 10^6 \square 3.098\times 10^8$.

For a substrate with the Young's modulus determined by DMA, the output voltage of the most left sensor, obtained from equation (5), agrees well with the measured values from experiments (FIG. 12A) for the actuator voltage ranging from 2 V to 5 V with an increment of 1 V.

The effect of shear stress at the device/prepared substrate interface is studied by comparing the experiment for the bare device (without the PDMS sample) to that for the substrate and PDMS sample having the same moduli. For the former (no PDMS sample) there is no crack opening such that any measured sensor voltage would result from the interfacial shear. For the latter, the effect of interfacial shear is the same as that for the former (because the PDMS sample has the same moduli as the substrate), but the crack opening due to expansion of actuator/sensor comes into play. In fact, its sensor voltage in experiments is much larger (by orders of magnitude) than that from the bare device (without PDMS sample) case. This clearly shows that the effect of interfacial shear is indeed negligible as compared to that for crack to opening (unless there is only bare device). This is consistent with the prior analyses of stiff devices on compliant substrates[3-6].

Viscoelastic Analysis

The relaxation modulus of PDMS can be expressed via the Prony series in the time domain as:

$$E(t) = E_0\left[1 - \sum_{i=1}^{N} g_i(1 - e^{-t/\tau_i})\right], \quad (S10)$$

where $E_0$ represents the initial modulus, $g_i$, $\tau_i$ and N are the parameters and number of terms in the Prony series. The limit of $E(t\to\infty)$ gives the fully relaxed modulus $$E_\infty = E_0\left(1 - \sum_{i=1}^{N} g_i\right).$$

The Laplace transform gives the frequency-dependent relaxation modulus, $$E(\omega) = E_\infty \frac{1 - \sum_{i=1}^{N} \frac{g_i}{1+\tau_i^2\omega^2} + j\sum_{i=1}^{N} \frac{g_i\tau_i\omega}{1+\tau_i^2\omega^2}}{1 - \sum_{i=1}^{N} g_i}, \quad (S11)$$

where, $j=\sqrt{-1}$, and $\omega=2\pi f$ is the angular frequency. The real and imaginary parts of the above equation represent the storage and loss moduli, respectively. The phase shift is defined by $\tan\delta=E_{loss}/E_{storage}$. The relaxation ratio ($g_i$) has been reported in the literature[9, 10], $g_1=0.137$, $g_2=0.0921$, and $g_3=0.315$. The relaxation time ($\tau_i$) is determined in the main text, which gives $\tau_1=0.0235s$, $\tau_2=0.00165s$, and $\tau_3=0.000281s$. The elastic modulus of PI is 5 orders of magnitude larger than that of the elastomer layer. Therefore, the bottom encapsulation may shield the viscoelastic effect of the device substrate on the output of the device.

Conformal Contact

The surface profile of the skin can be generally represented by:

$$w(x) = \frac{h_{skin}}{2}\left[1 + \cos\left(\frac{2\pi x}{\lambda_{skin}}\right)\right], \quad (S12)$$

where $h_{skin}$ and $\lambda_{skin}$ represent the roughness and wavelength of the skin, respectively. Since the skin is much more compliant than the device, it conforms to the device, which leads to the normal traction on the skin surface:[11]

$$T(x) = \frac{\pi \bar{E}_{skin} h_{skin}}{2\lambda_{skin}} \cos\left(\frac{2\pi x}{\lambda_{skin}}\right), \quad (S13)$$

where $\bar{E}_{skin}$ represents the plane-strain modulus of the skin. The deformation energy (per unit length) of the skin is:

$$\bar{U}_{skin} = \frac{1}{\lambda_{skin}} \int_0^{\lambda_{skin}} T(x) w(x) dx = \frac{\pi \bar{E}_{skin} h_{skin}^2}{8\lambda_{skin}}. \quad (S14)$$

The adhesion energy (per unit length) is[1]

$$\bar{U}_{adhesion} = -\frac{\gamma}{\lambda_{skin}} \int_0^{\lambda_{skin}} \sqrt{1 + (w')^2}\, dx \approx -\gamma\left(1 + \frac{\pi^2 h_{skin}^2}{4\lambda_{skin}^2}\right), \quad (S15)$$

where $\gamma$ is the work of adhesion between the skin and the device. The total energy is obtained from equations (S14) and (S15) as $$\bar{U}_{total} = \frac{\pi \bar{E}_{skin} h_{skin}^2}{8\lambda_{skin}} - \gamma\left(1 + \frac{\pi^2 h_{skin}^2}{4\lambda_{skin}^2}\right). \quad (S16)$$

Conformal contact of the device and skin requires the total energy less than zero, its value for unadhered state, i.e., $\bar{U}_{total} < 0$, which gives the maximum roughness for conformal contact $$\left(\frac{1}{8} - \frac{\pi \gamma}{4\lambda_{skin} \bar{E}_{skin}}\right) h_{skin}^2 \leq \frac{\gamma \cdot \lambda_{skin}}{\pi \bar{E}_{skin}}. \quad (S17)$$

For the skin roughness[12] $h_{skin}=5\sim10$ μm, $\lambda_{skin} \approx 7 h_{skin}$, $\bar{E}_{skin} \approx 130$ KPa and equation (S17) clearly holds such that the device and skin have intimate contact, and the device remains essentially flat. Therefore, the sensor's output voltage is independent of the roughness of the skin.

Characterization of a Conformal Modulus Sensor

FIGS. 1A-1G, 2A-2P, and 3 provide schematic diagrams and images of an exemplary conformal modulus sensor (CMS). The ultrathin architectures of the active elements together with the serpentine configurations of the metal traces that establish electrical connection to them yield low modulus, stretchable mechanics when supported by a thin elastomer (Ecoflex 00-30, SMOOTH-ON; weight ratio of 1A:1B, 60 kPa, 20 μm thick). The resulting device was able to directly couple to the surface of the skin and other biological tissues by van der Waals forces alone. Application and removal of the device occurs non-invasively, over multiple cycles of use, without significant change in measurement accuracy. The rectangular structures are capacitor-type components, each of which incorporates a layer of piezoelectric material (PZT, 500 nm thick) between bottom (Ti/Pt, 20 nm/300 nm) and top (Cr/Au, 10 nm/200 nm) electrodes, with an encapsulation layer of polyimide. Such elements serve as both mechanical actuators and sensors. See the section entitled "Neutral Mechanical Plane and Bending Stiffness" for details. Studies with human epithelial keratinocytes indicate that the devices are biocompatible and that the cell culturing process does not change their surface properties (See FIGS. 4A-4B).

Figure 3:
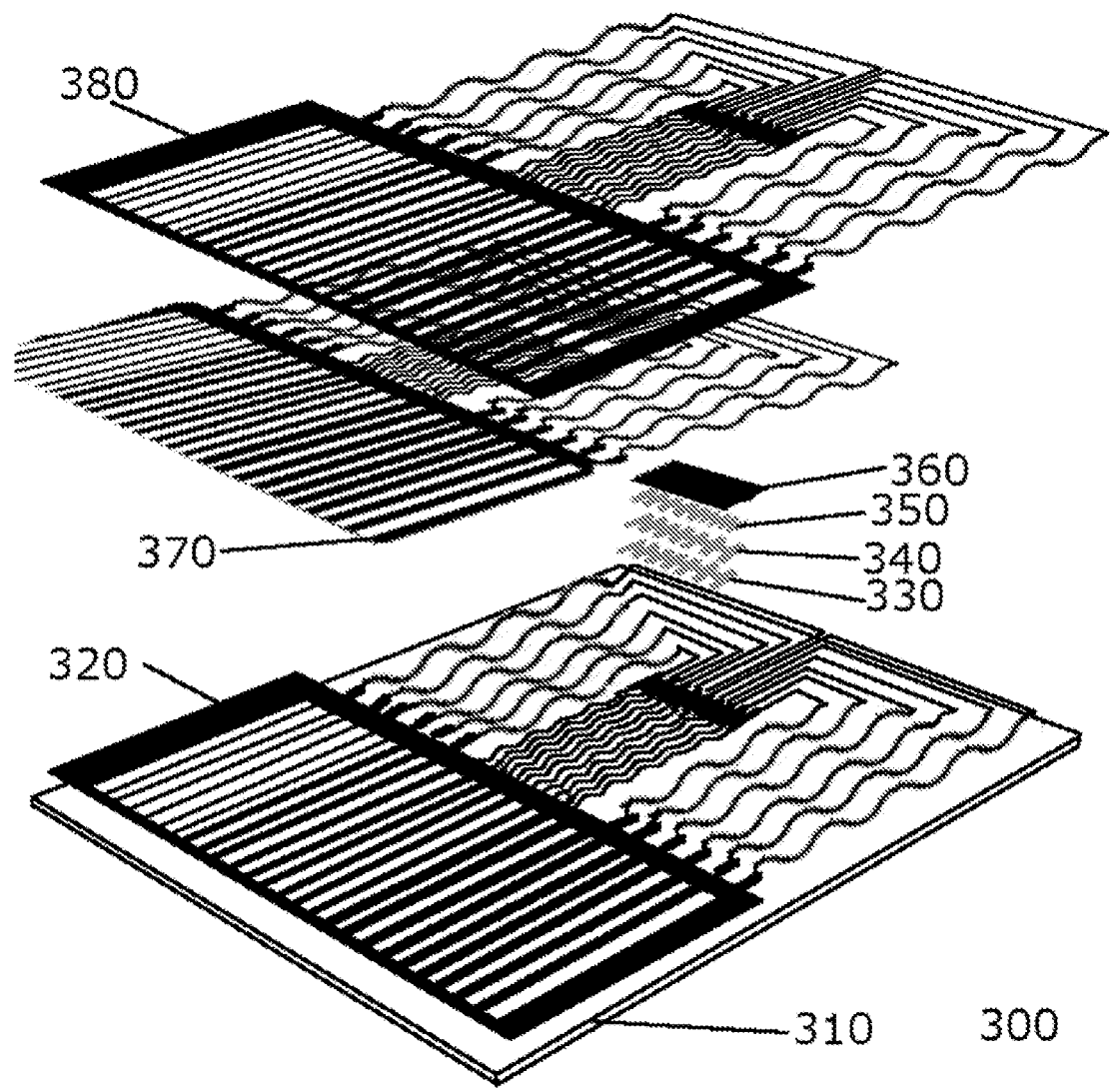
FIG. 3 is an exploded view of a thin compliant modulus sensors (CMS) based on nanoribbons of PZT in arrays of mechanical actuators and sensors (A-s & S-s).
Figure 4A:
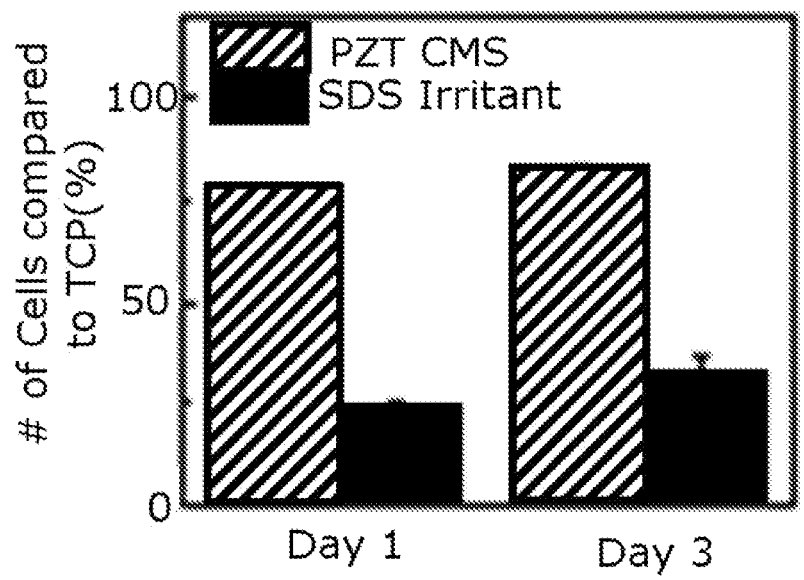
FIG. 4A depicts the results of an MTT assay of human epithelial keratinocyte (HEK) on a device after 1 and 3 days of culture as a percentage of cells grown on tissue culture plate. Cells incubated with 5% SDS served as a positive control.
Figure 4B:
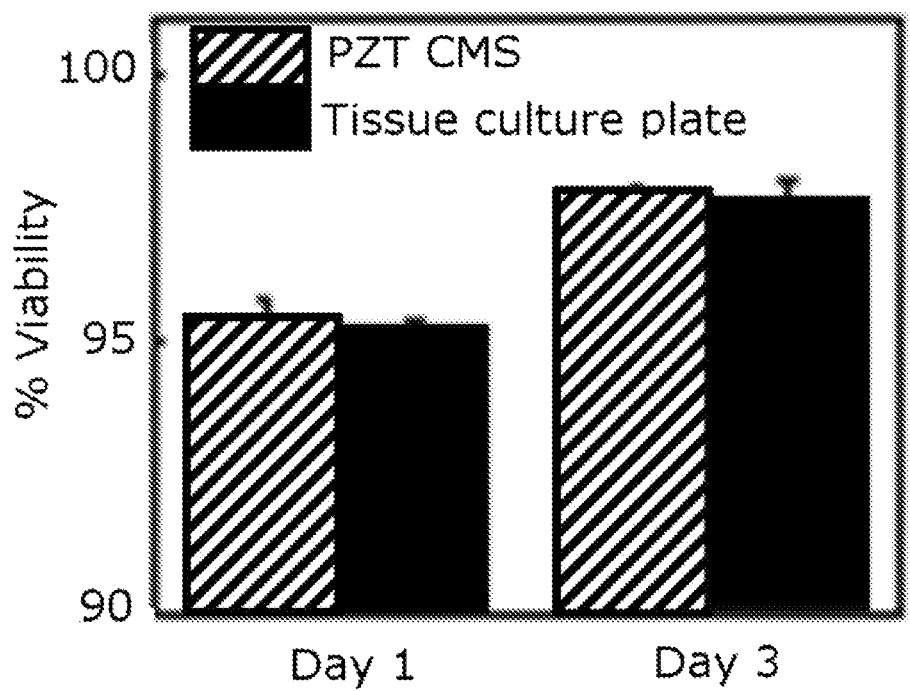
FIG. 4B depicts the cell viability on a device and on a tissue culture plate after 1 and 3 days of culture.
Figure 5A:
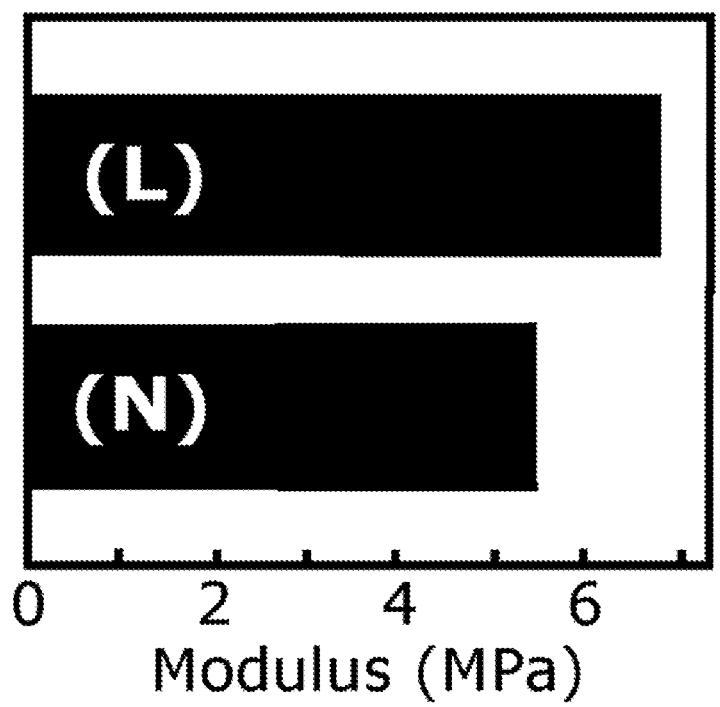
FIGS. 5A-5E depict the in vivo modulus values obtained from various body locations for normal (N) and lesion (L) skin.
Figure 5B:
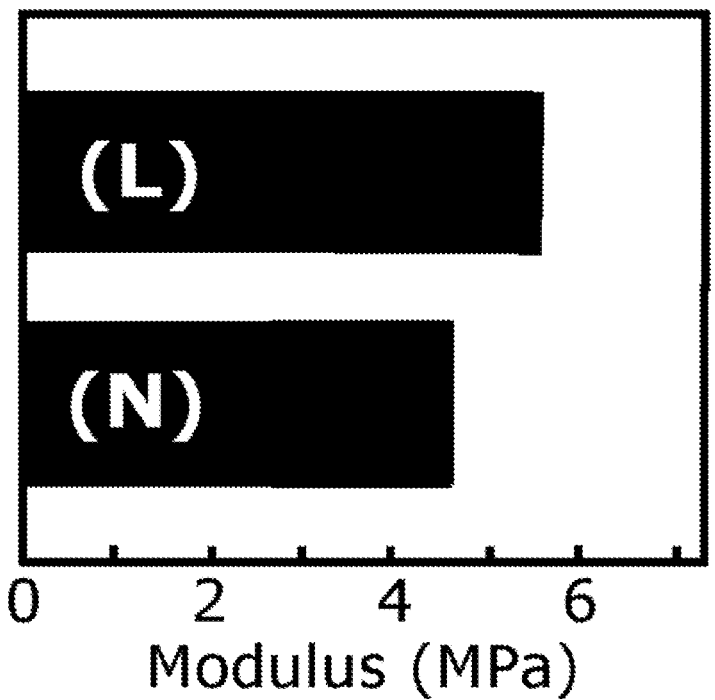
Figure 5C:
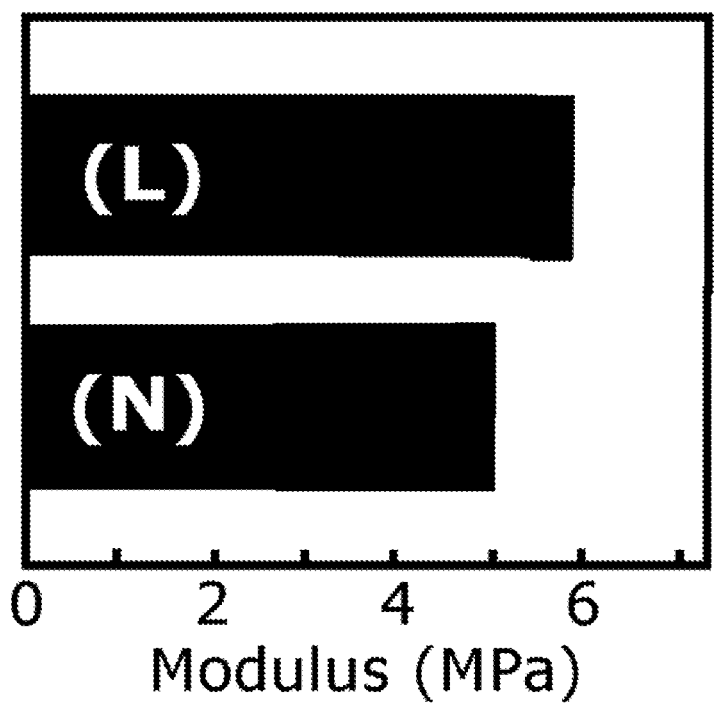
Figure 5D:
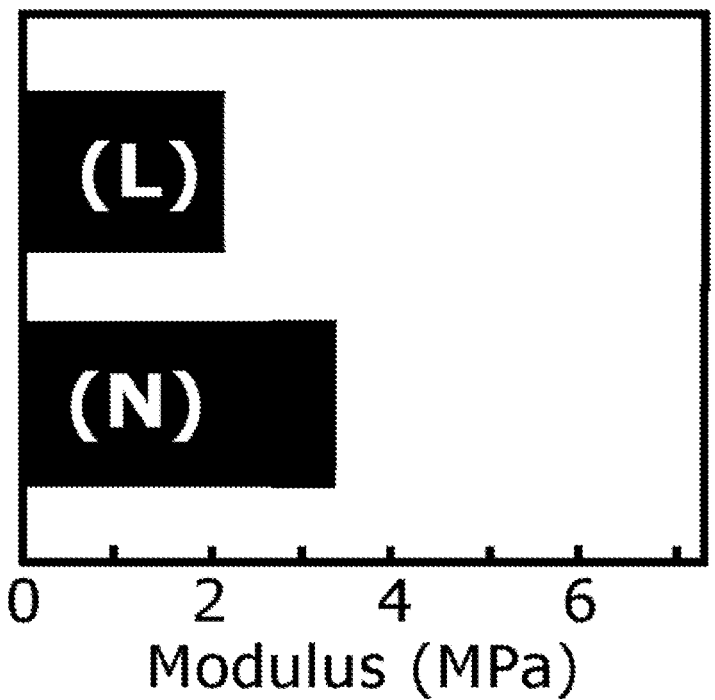
Figure 5E:
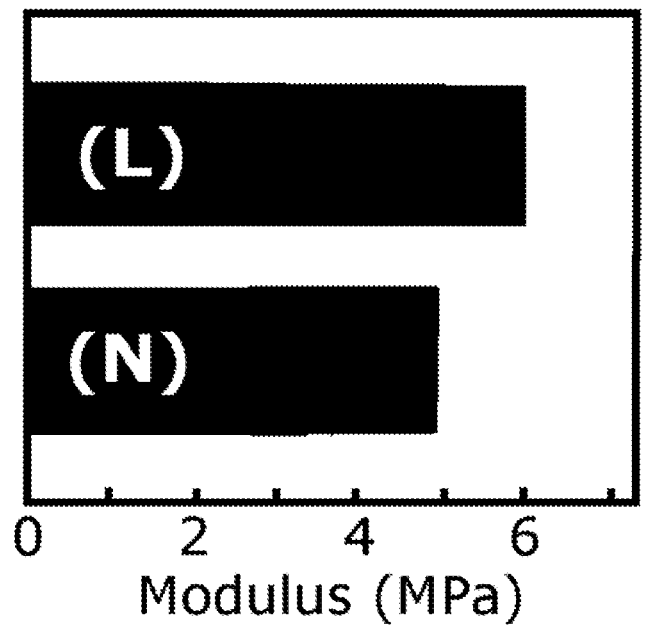
Figure 6A:
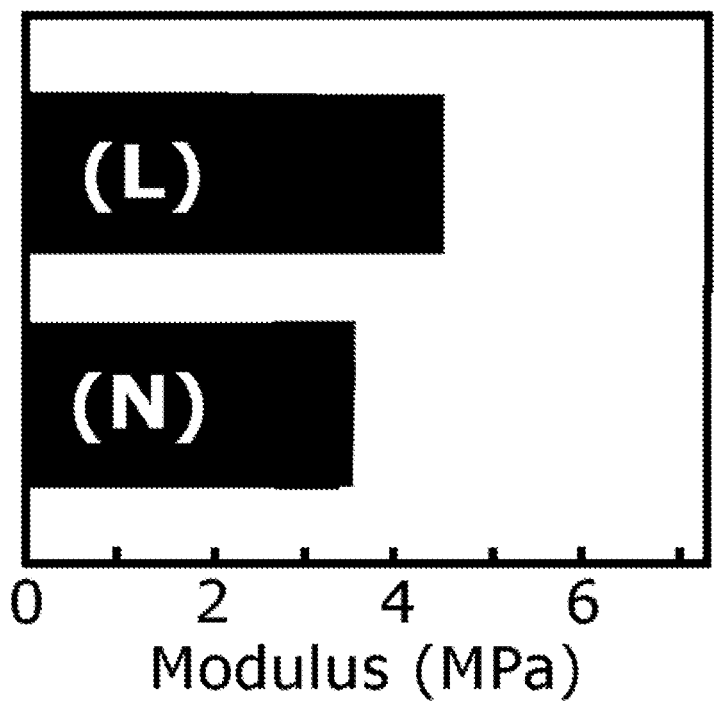
FIGS. 6A-6E depict in vivo modulus values obtained from various body locations for normal (N) and lesion (L) skin.
Figure 6B:
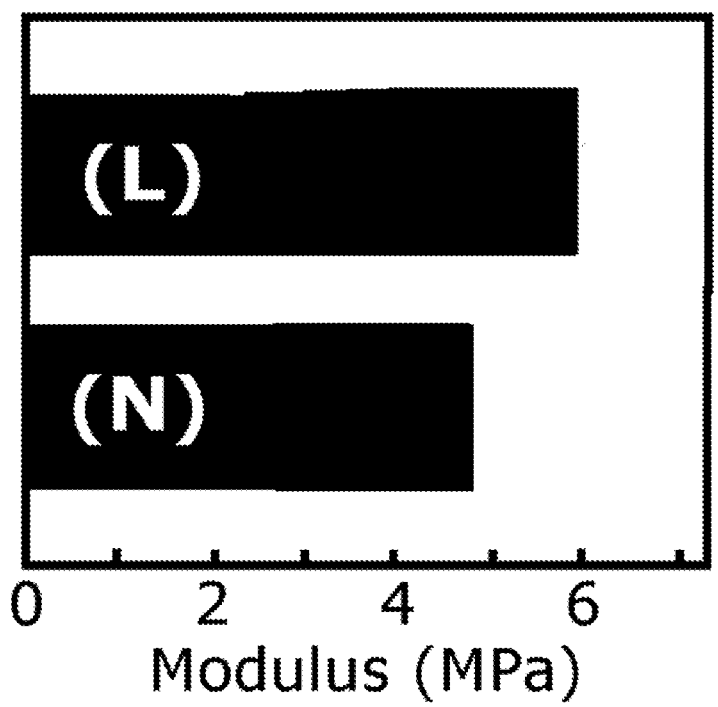
Figure 6C:
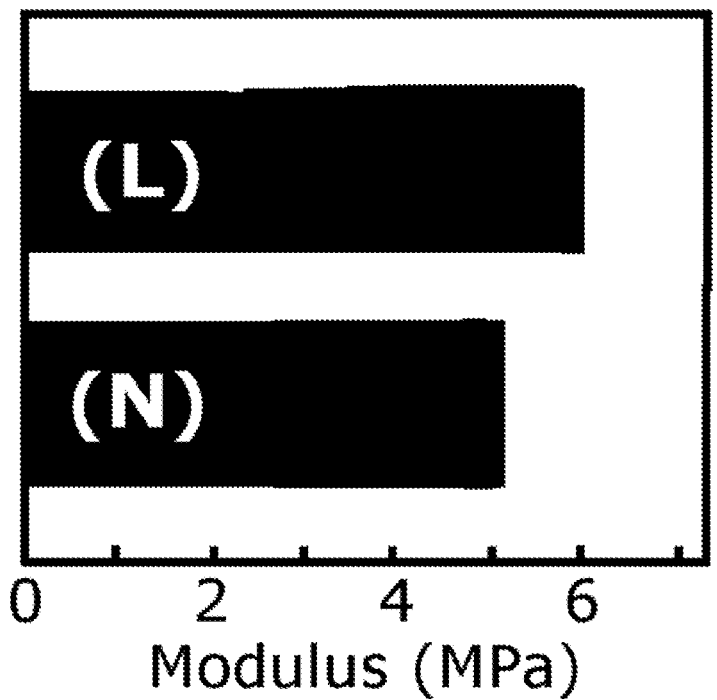
Figure 6D:
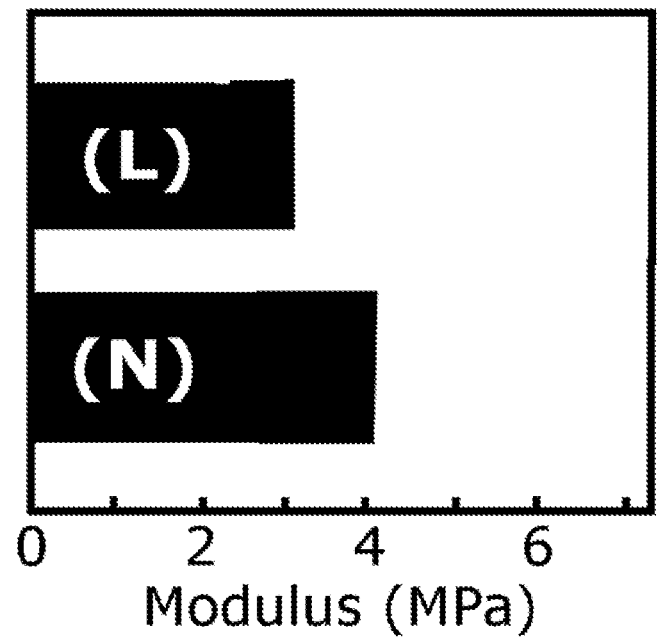
Figure 6E:
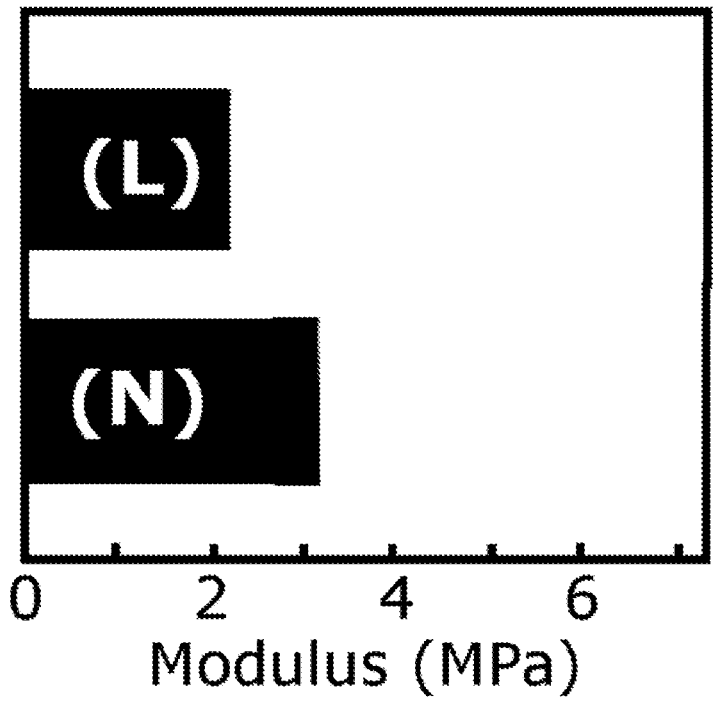
Figure 7A:
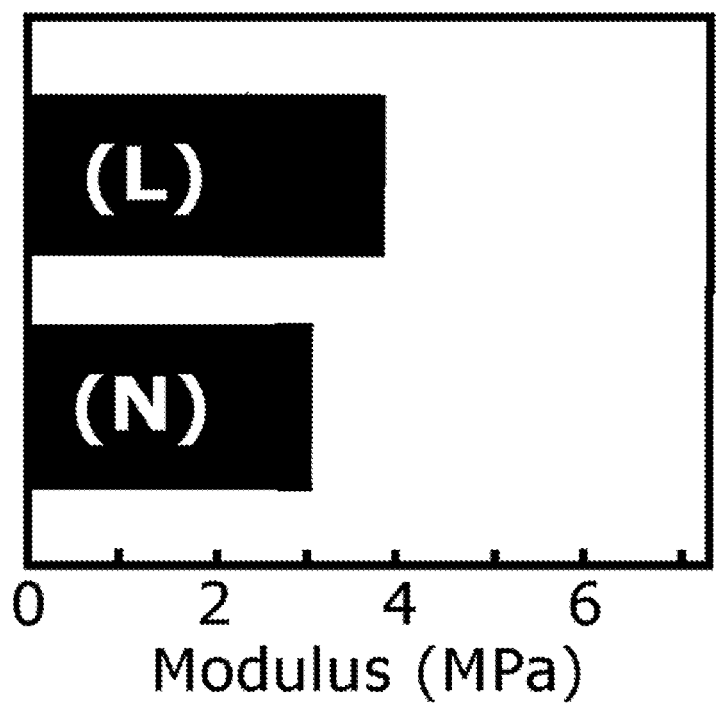
FIGS. 7A-7D depict in vivo modulus values obtained from various body locations for normal (N) and lesion (L) skin.
Figure 7B:
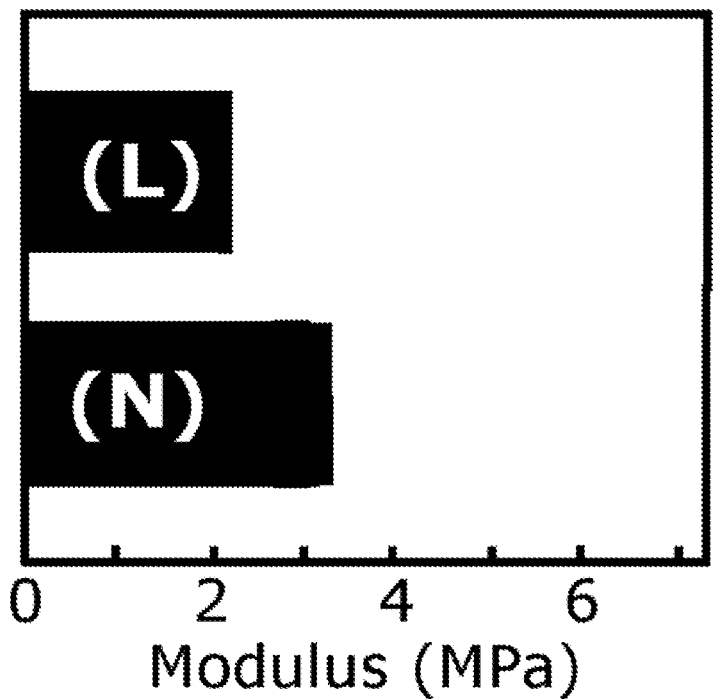
Figure 7C:
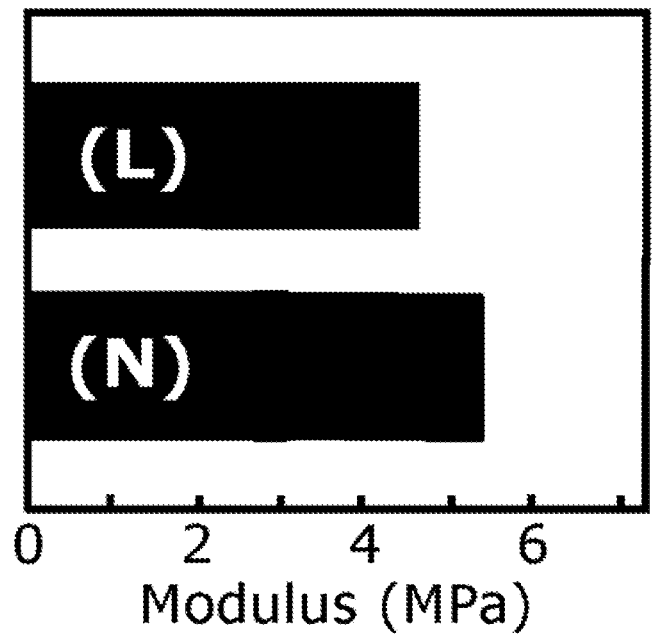
Figure 7D:
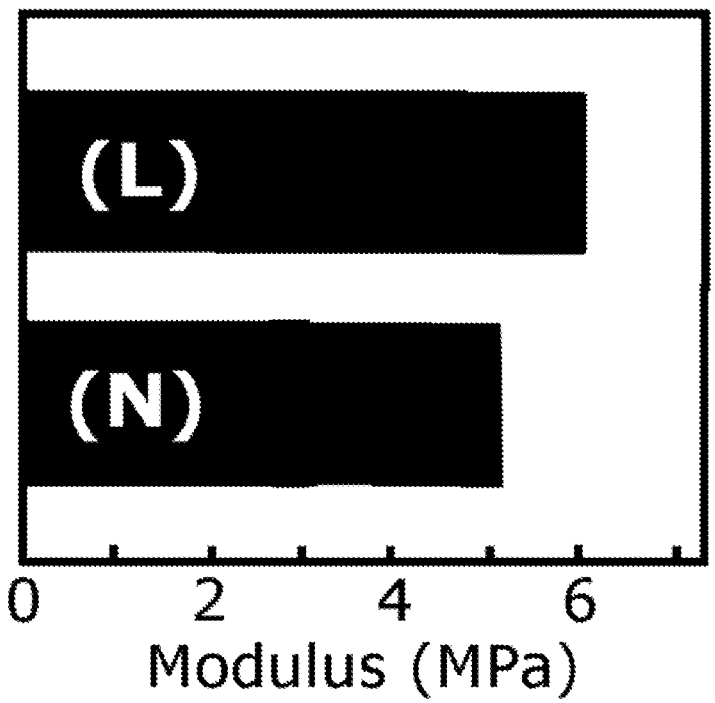
Figure 8A:
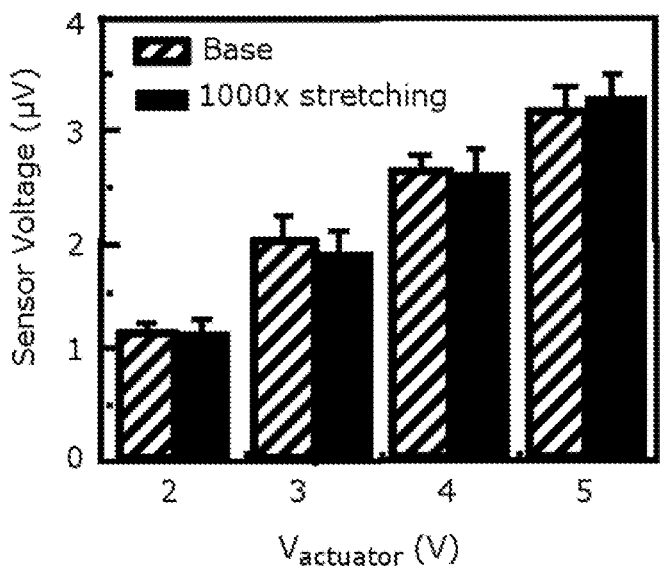
FIGS. 8A-8B depict characteristics of a PZT CMS under cyclical application of tensile strain.
Figure 8B:
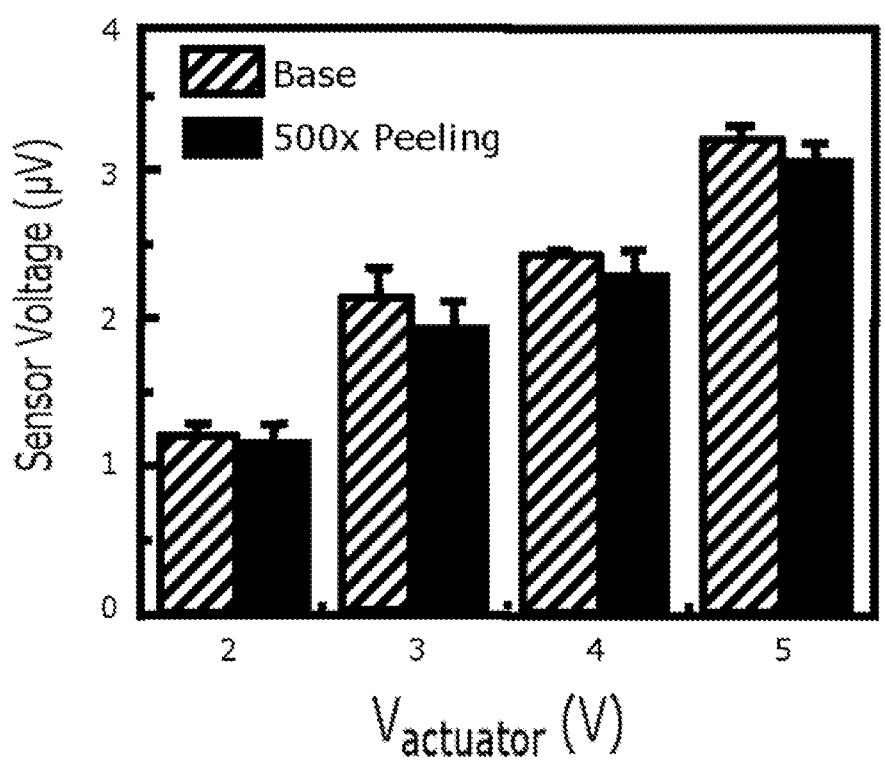
Figures 9A, 9B, 9C, 9D, 9E, 9F:
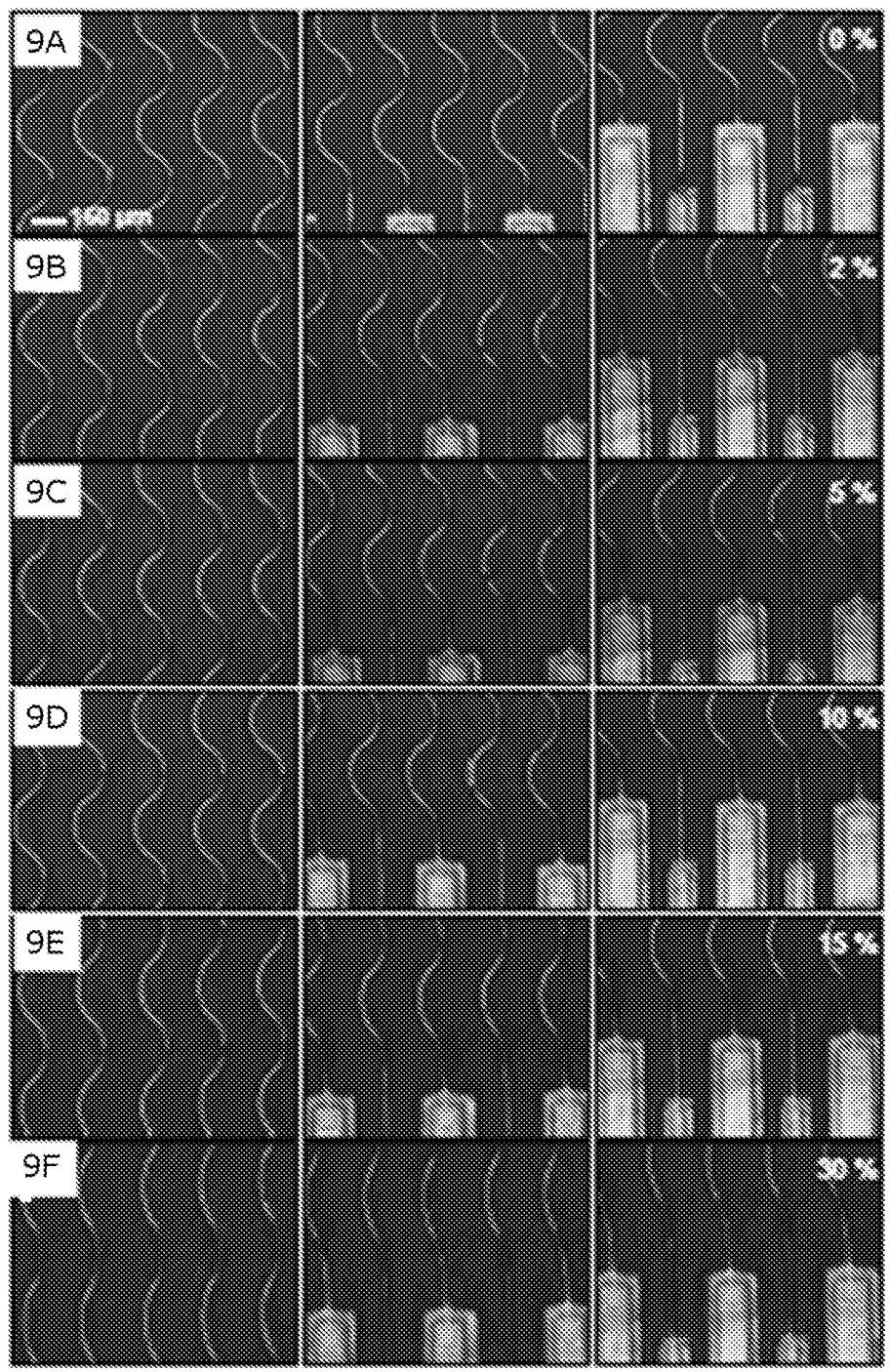
FIGS. 9A-9F depict optical micrographs of serpentine interconnections and arrays of sensors and actuators at various levels of tensile strain.

The exemplary CMS module contains seven actuators (each with lateral dimensions of 200×1000 μm2) and six sensors (each with lateral dimensions of 100×500 μm2) as shown (without the elastomer substrate) mounted on an artificial skin surface. An exploded view of an exemplary CMS module is depicted in FIG. 3. The CMS device 300 contains an array of seven actuators (each with lateral dimensions of 200×1000 μm2) and six sensors (each with lateral dimensions of 100×500 μm2) formed from a bottom electrode layer 330 (in this case Pt is used as a bottom electrode), a piezoelectric actuating/sensing layer 340 (the piezoelectric in this case is PZT), and a top electrode layer 350 (in this example Au is used as the top electrode) with a PI encapsulation layer 360. A layer of gold serpentine interconnects 370 allows each of the sensors and actuators to be addressed. The entire device is encapsulated a top 380 and bottom 320 layer of polymer such as PI and the entire device can be coupled to the surface of a substrate 310. The device could be directly coupled to a surface such as silicone, glass, or skin through Van der Waals interactions. Both the serpentine interconnections and the sensors/actuators) conform to this textured surface, even without the elastomer, as was confirmed by scanning electron microscope (SEM) images. The bending stiffness per width (4.55× 10$^{-8}$ Nm) and the position of the neutral mechanical plane (near the middle of the PZT layer) can be obtained analytically, as described above. For a bending radius as small as 0.3 mm, the maximum strains in the PZT and the polyimide are only 0.1% and 1%, respectively. Measurements indicate stable performance characteristics under hundreds of cycles of bending (See FIGS. 8A-8B) and uniaxial strains as high as 30% (See FIGS. 9A-9F).

Characterization of Mechanical Properties of Skin

With the device conformally mounted on the skin, application of a sinusoidally varying voltage (angular frequency ω) to a selected actuator induces mechanical motions in the PZT and associated device structures including the elastomer backing and, through physical contact, the underlying skin. These motions mechanically couple, through the skin and the elastomer, to the adjacent sensor elements. Detecting the voltage response (amplitude and phase) of each sensor at the actuation frequency determines the extent of this coupling. By neglecting the effects of interfacial shear stress, an approximate theoretical model can be constructed (See FIGS. 10A and 10B) to describe the response, and to relate it, explicitly, to the mechanical properties of the skin. Here, as shown in FIG. 10C, the interfaces between the PZT elements and the skin can be treated as interfacial cracks. A constant voltage $U_A$ (same as the amplitude of the sinusoidally varying voltage used in experiment) applied to a given element (actuator, A) induces an expansion ($\delta_{active-A}$) that is 6 to 8 orders of magnitude larger than that of any other element (sensor, S) in the array ($\delta_{A/S}$); the latter is therefore negligible, i.e., $$\begin{cases} \delta_{active-A} = \Delta u \\ \delta_{A/S} = 0 \end{cases} \quad (1)$$

where, $\Delta u$ is obtained analytically as $$\Delta u = \beta_1 \frac{e_{33}}{c_{33}} U_A. \quad (2)$$

where, $c_{33}$ and $e_{33}$ are the elastic and piezoelectric parameters of the PZT, respectively, and the dimensionless parameter $\beta_1$ depends on the materials and geometries associated with the multilayer structure of the device, but is approximately independent of the modulus of the sample under test, provided that this sample has a moduli much smaller than that of the actuator (e.g. six orders of magnitude difference between PZT and the skin). See the section entitled "Piezoelectric Analysis" for details.

The stress induced by the actuator on each of the other elements in the array can be characterized by its average stress ($p_{S,i}$ for the $i^{th}$ sensor element in the array) according to:

$$p_{S,i} = \eta_i \frac{\Delta u \cdot E_{P.S.}}{2a}, \quad (3)$$

where $E_{P.S.}$ and 2a represent storage (elastic) modulus of the skin (or, more generally, the substrate under test) and the width of the sensor, respectively. An expression for the dimensionless parameter $\eta_i$ appears above. The output voltage of the $i^{th}$ element is then obtained $$U_{S,i} = \beta_2 \frac{p_{S,i} \cdot h_{PZT}}{e_{33}}, \quad (4)$$

where, $h_{PZT}$ represents the thickness of the PZT layer, and the dimensionless parameter $\beta_2$ depends on the materials and geometries associated with the multilayer structure of the device. See the section entitled "Interfacial Crack and Sensor Output Voltage". Substitution of equations (2), (3) into equation (4) leads to $$U_{S,i} = \alpha_1 \frac{h_{PZT}}{2a} \frac{E_{P.S.}}{c_{33}} U_A \quad (5)$$

where $\alpha_1 = \beta_1 \cdot \beta_2 \cdot \eta_i$ decays exponentially with location of the $i^{th}$ sensor element, i.e $$\frac{\alpha_i}{\alpha_1} \propto e^{-(j-1)}. \quad (6)$$

Due to the dynamic nature of the measurement process, viscoelastic effects can be important. In general, the dependence of the storage (elastic) modulus on $\omega$ can be expressed as a Prony series, according to $$E_{P.S.}(\omega) = E_\infty \frac{1 - \sum_{i=1}^{N} \frac{g_i}{1 + \tau_i^2 \omega^2}}{1 - \sum_{i=1}^{N} g_i}, \quad (7)$$

where $E_\infty$ is the fully relaxed modulus (when $\omega=0$), and $g_i$ and $\tau_i$ are the relaxation ratio and relaxation time in the Prony series, respectively. See, e.g., *Theory of Viscoelasticity: An Introduction* by Christensen, R. (Elsevier, 1982).

Relaxation times range from micro-seconds to seconds for the skin, which we assume to be much shorter than those for the constituent materials of the CMS. For the range of frequencies (100~1000 Hz) and biological samples examined here, we neglect viscoelastic effects in the device. For consistency, we used this same approximation in the control studies described next.

Figure 12A:
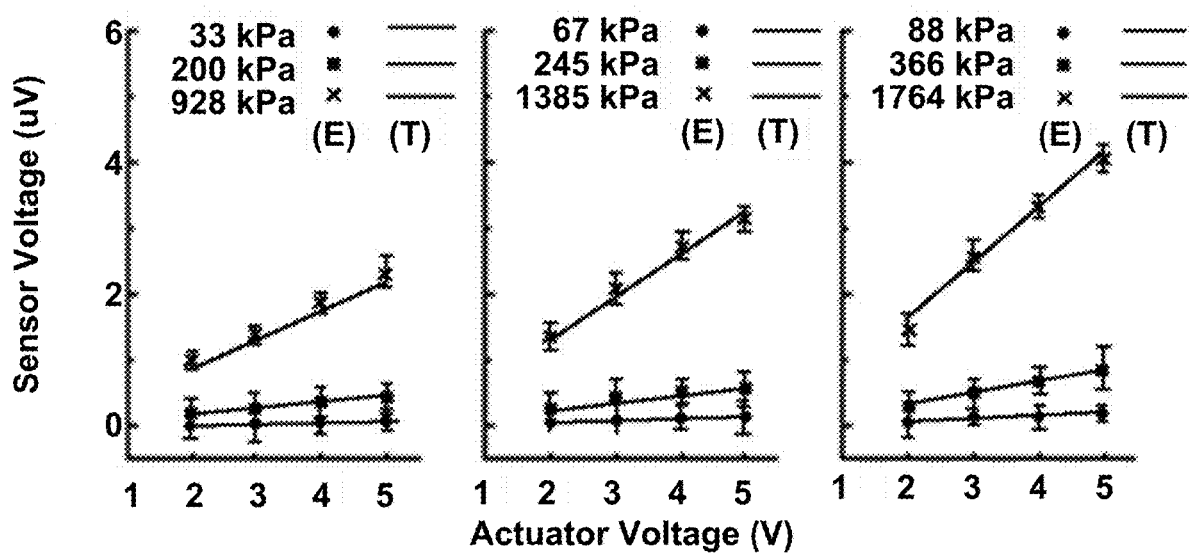
FIGS. 12A-12E depict experimental and theoretical studies of the measurement physics of a conformal modulus sensor. Here, and in all other cases, the symbols and lines correspond to experimental (E) and theoretical (T) results, respectively.
Figure 12B:
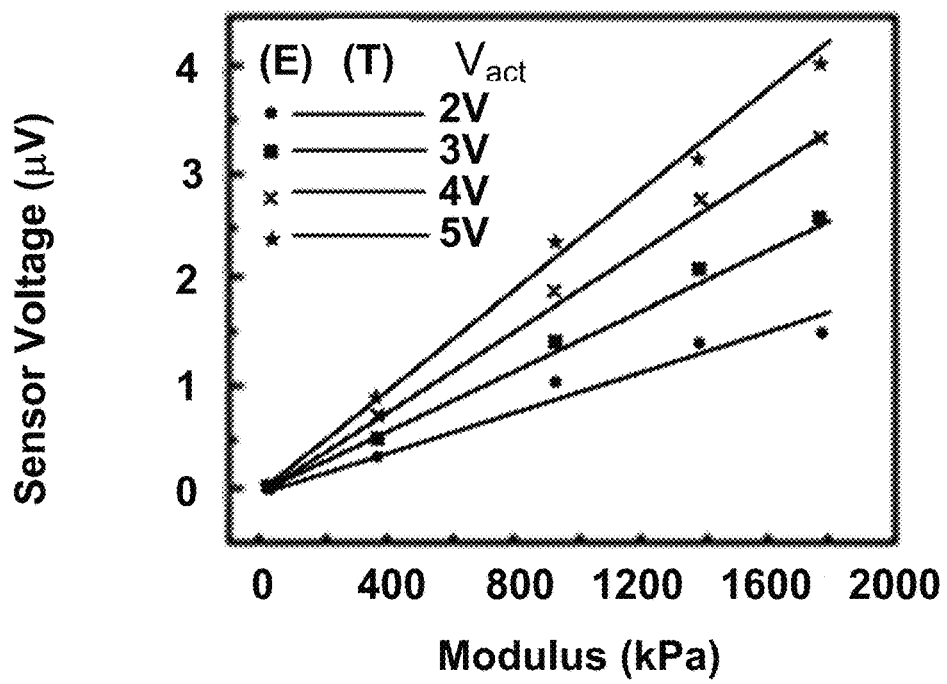
Figure 12C:
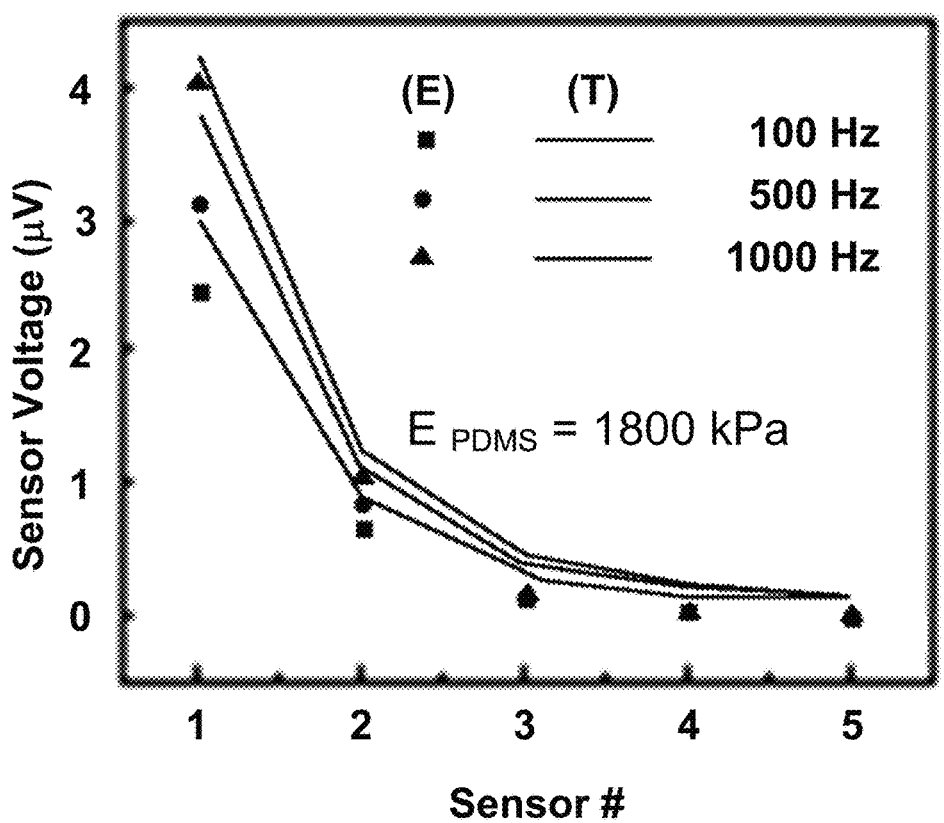
Figure 12D:
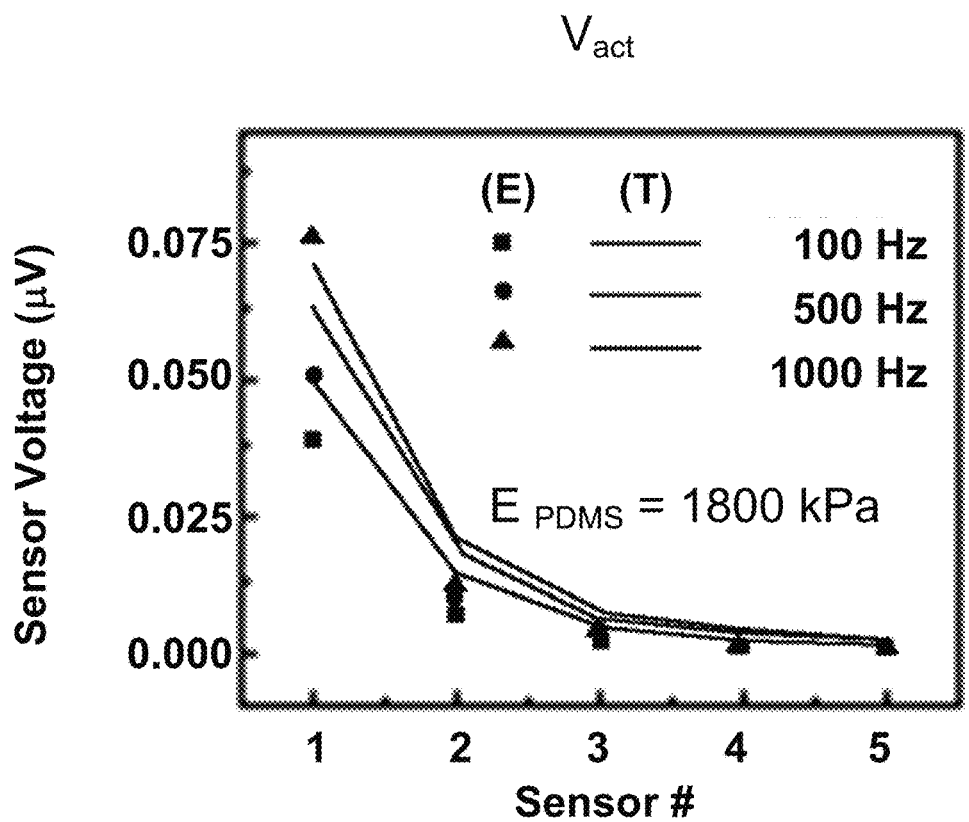

Experiments designed to examine these predicted relationships involved a set of samples of polydimethylsiloxane (PDMS, Sylgard 184, Dow Corning) formulated to yield a range of Young"s moduli (See FIG. 11) relevant to skin and other soft biological tissues. The data recording system was a lock-in amplifier (SR830, Standard Research Systems, USA), a multiplexer (FixYourBoard.com, U802, USA), and a laptop computer for determining both the amplitude of the voltage response of each sensor in the array and its phase shift ($\delta$) relative to the sinusoidal voltage applied the actuator. Measurements at 1000 Hz show that the amplitudes of the sensor voltages vary linearly with the actuator voltages (FIG. 12A) and with the Young"s modulus (separately evaluated using a dynamic mechanical analyzer; Q800 DMA at 0 Hz) of the sample under test (FIG. 12B), consistent with equation (5). The amplitudes decay in an approximately exponential fashion with distance, as expected based on equation (6). The amplitude for each sensor can be used with equation (5) to define a value of $E_{P.S.}$. The phase shift then defines the loss modulus according to $Et_{loss}=E_{P.S.}$ tan($\delta$), where the loss modulus is given above. Measurements at different actuation frequencies (100 Hz, 500 Hz and 1000 Hz) yield the frequency dependence of these two moduli (FIGS. 12C and 12D). With relaxation ratios $g_i$ in the Prony series taken from the literature, the fully relaxed modulus $E_\infty$ and relaxation times $\tau_i$ (for N=3) can be determined from the thirty sensor data points (5 sensors on two different PDMS formulations, with fully relaxed moduli of 30 kPa and 1800 kPa, at three measurement frequencies) via the following relation, which results from equations (5) and (7):

$$U_{S,i} = \alpha_i \frac{h_{PZT}}{2a} U_A \frac{E_\infty}{c_{33}} \frac{1 - \sum_{i=1}^{N} \frac{g_i}{1 + \tau_i^2 \omega^2}}{1 - \sum_{i=1}^{N} g_i} \quad (8)$$

Figure 12E:
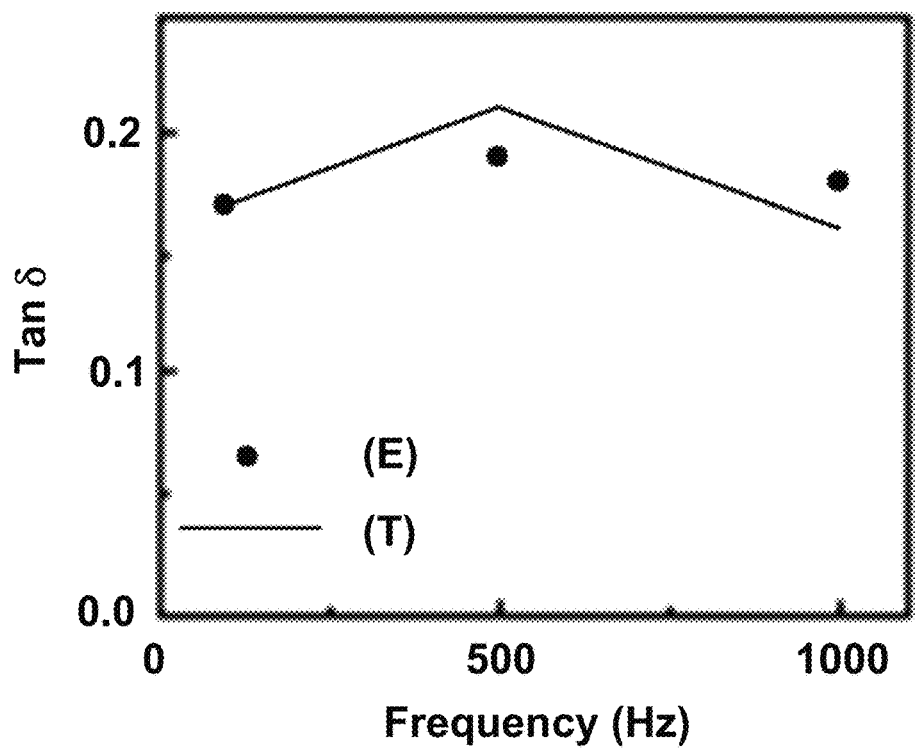

(see details above). The fully relaxed moduli agree well with those measured independently by DMA at ~0 Hz. The $\tau_i$ determined in this manner, together with the relaxation ratios $g_i$, give the phase shifts $\delta$, which agree well with the values determined from experiment (FIG. 12E).

Figures 13A, 13B, 13C:
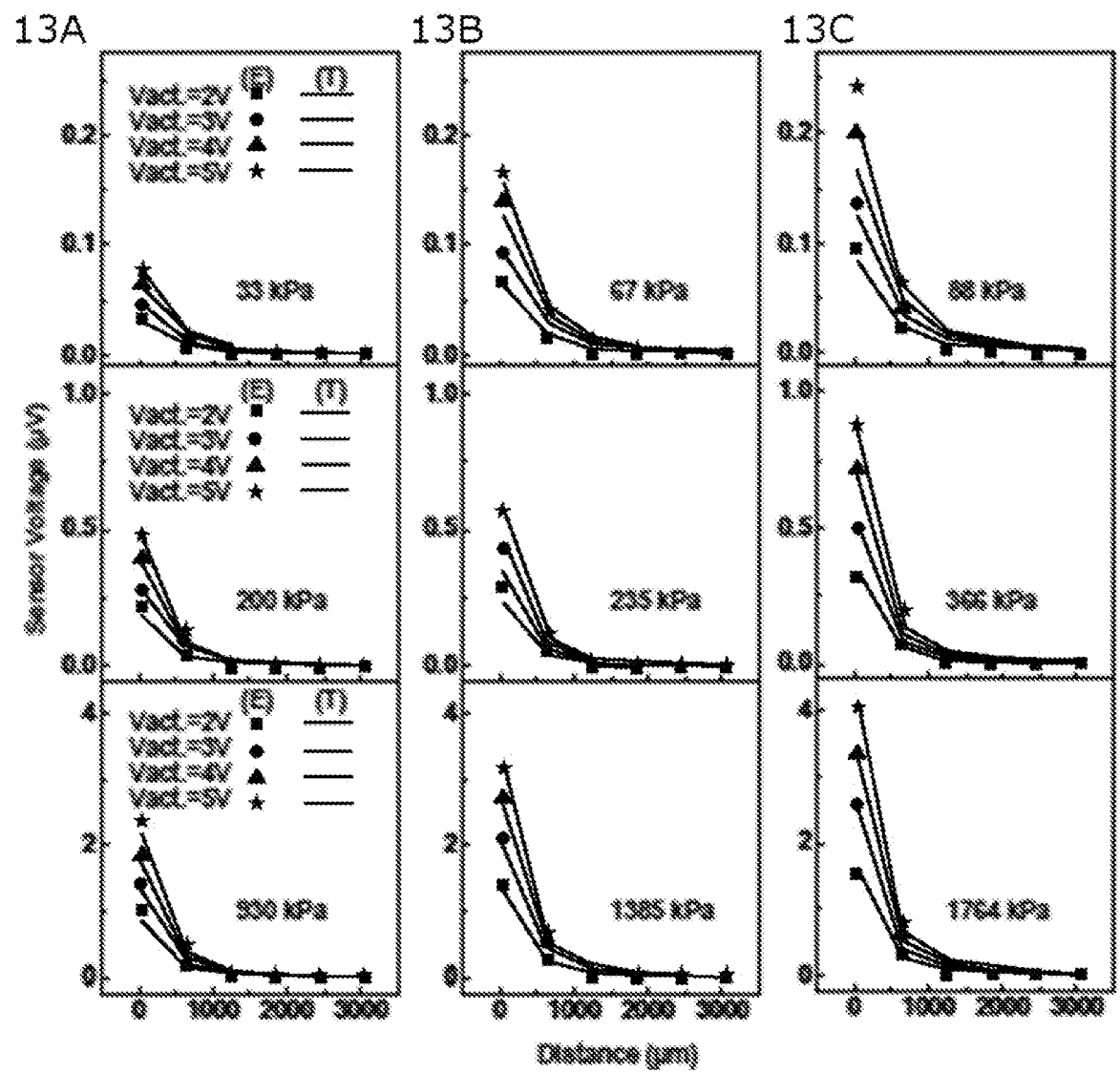
FIGS. 13A-13C depict the data from a PZT CMS device used for in vitro characterization of PDMS test samples with various modulus values. The experimental and theoretical results are shown as symbols and lines, respectively.
Figure 14:
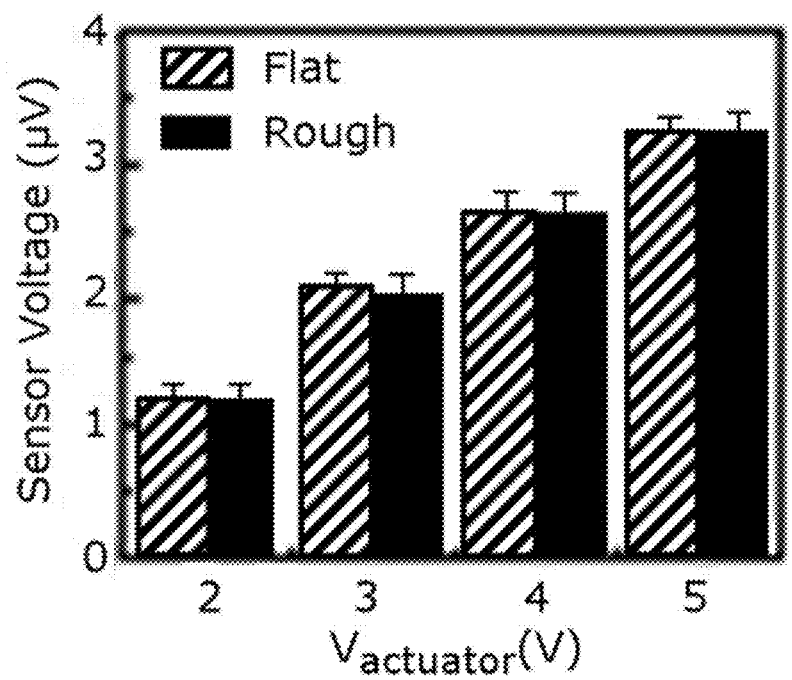
FIG. 14 is a graph of sensor voltage as a function of actuator voltage for a PZT CMS for the cases of flat and rough substrates. The error bars represent the standard errors.

For the Prony series obtained above and an actuation frequency of 1 kHz, the fully relaxed moduli can be obtained in the same way for nine different PDMS formulations (when applied to the outputs of each of the sensors; See FIGS. 13A-13C). All results agree well with those determined independently by DMA at ~0 Hz, as shown in FIGS. 12A and 12B. Consistent with the previous examples, the output voltages are linearly proportional to the modulus of the sample under test, over the entire range, from 30 kPa to 1800 kPa. Application to the rough surfaces of artificial skin structures formed by molding these same formulations of PDMS yielded similar results (See FIG. 14). Here, as well as in cases of large-scale curvature, the neutral mechanical plane layout with respect to the PZT is important (See FIG. 15). See section entitled "Conformal Contact".

Figure 16A:
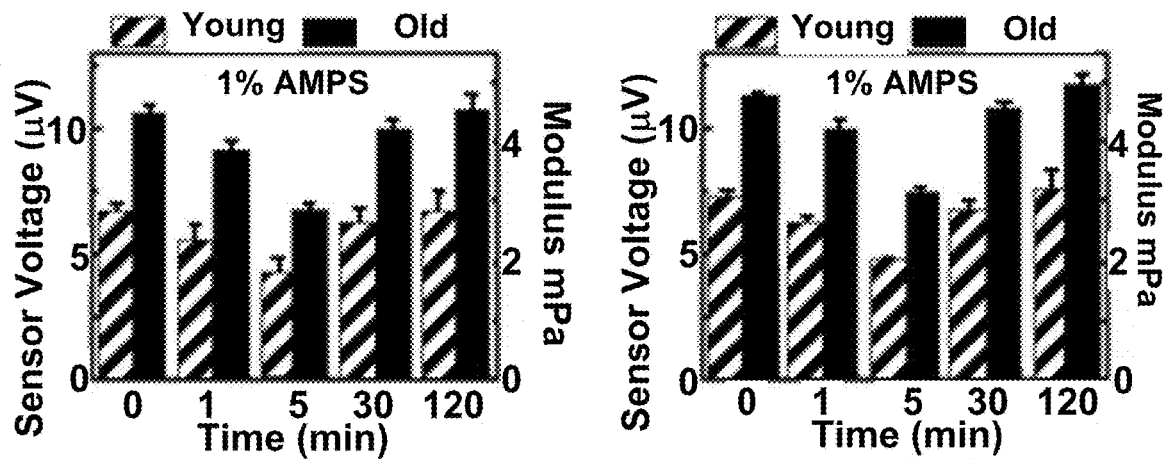
FIGS. 16A-16C depict modulus measurements on ex vivo female and male skin samples as a function of time before and after application of a moisturizing lotion.
Figure 20A:
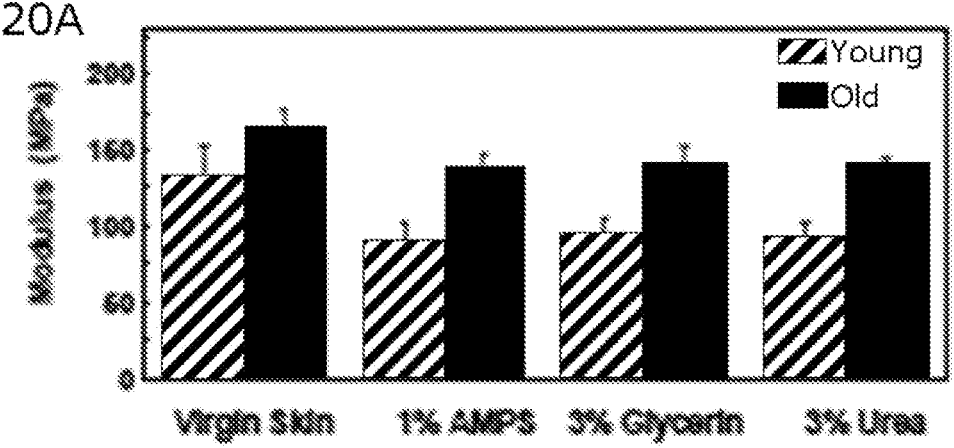
FIGS. 20A-20B depict nanoindentation measurements on ex vivo skins.
Figure 20B:
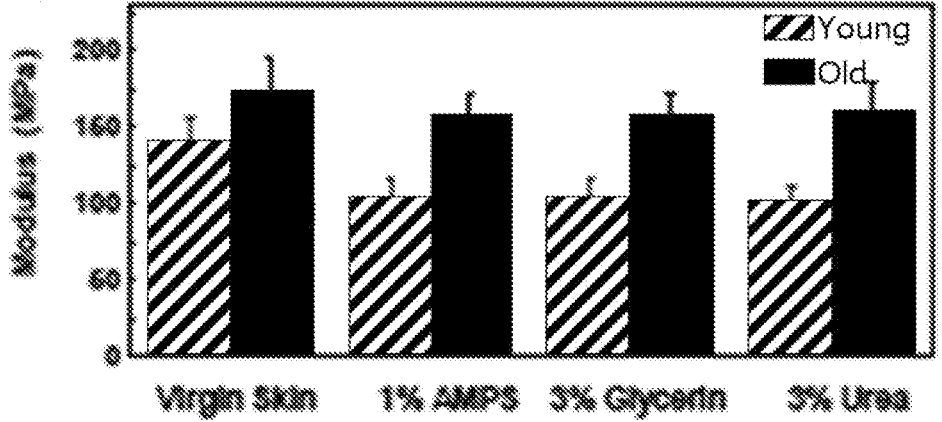

These findings establish the CMS as a versatile tool for characterizing the mechanical properties of soft materials. The following examines use with biomaterials, with a focus on the storage modulus evaluated at a given frequency. As a demonstration of utility with skin, CMS data obtained from ex vivo samples reveal the effects of moisturizing agents and hydration state, in systematic experiments that involve measurements before and at various times after application of solutions containing 1% AMPS (acrylamidomethylpropane sulfonic acid), 3% Glycerin, and 3% Urea. Results for AMPS (supplied by L"Oreal Inc.) applied on ex-vivo abdominal skin samples from 35 and 66 year old females (left graph), and 33 and 69 year old males (right graph), appear in FIG. 16A. FIGS. 19A-19D summarizes similar results for 3% Glycerin and 3% Urea. (In all cases, error bars correspond to calculated standard error.) Consistent with expectation and previous reports, the modulus of the skin generally increases with age, and is typically higher in males (3.01 MPa and 4.72 MPa for the 33 and 69 year old cases, respectively) than females (2.79 MPa and 4.46 MPa for 35 and 66 year old, cases, respectively). The magnitudes of the moduli lie between those measured using ultrasonic methods or nanoindentation on ex-vivo abdominal skin embedded in epoxy resin (See FIGS. 20A-20B see Methods and Tables 1 and 2) and determined in the small strain regimes with techniques based on tension, torsion or suction. See Table 3. In all cases, however, the percentage variations in moduli with gender are similar, with the exception of reports using suction, which suggest that female skin can exhibit slightly higher modulus than male skin. Effects of age in both males and females are similar to those in other literature reports. As skin ages, it becomes thinner, stiffer, and less flexible.

TABLE 1

Modulus values of ex-vivo human abdominal skin using nanoindentation and CMS.

| Subjects | $E_{CMS}$(MPa) | $E_{indentation}$(MPa) |
|---|---|---|
| Young Female: 35 years old | 2.7946 ± 0.1924 | 130.3773 ± 23.1960 |
| Young Male: 33 years old | 3.0108 ± 0.1740 | 140.1820 ± 16.5427 |
| Old Female: 66 years old | 4.4636 ± 0.1320 | 163.2340 ± 12.5963 |
| Old Male: 69 years old | 4.7164 ± 0.1010 | 172.4880 ± 22.8257 |

TABLE 2

Percentage variations in moduli of ex-vivo human abdominal skin between genders and age using nanoindentation and CMS. (* The site of the skin is not mentioned.)

| | Gender Male vs. Female | | Age Old vs. Young | |
|---|---|---|---|---|
| | Young | Old | Male | Female |
| % Variation for CMS | 7.1808 ± 0.1266 | 5.3600 ± 0.0509 | 39.1631 ± 0.0792 | 37.3913 ± 0.0984 |
| % Variation for Nanoindentation | 6.9942 ± 0.2959 | 5.365011 ± 0.2095 | 18.7294 ± 0.2503 | 20.1286 ± 0.25551 |

TABLE 3

Variation in skin (human) modulus between genders as measured by CMS and various techniques from literature.

| Reference | Sites | Young's Modulus (MPa) | Method |
|---|---|---|---|
| Silver et al. | Female* | 0.6 | Tension |
| | Male* | 2.1 | |
| Stark et al. | Female* | 0.26 | Tension |
| | Male* | 0.83 | |
| Diridollu et al. | Female - Forehead | 0.25 | Suction |
| | Male - Forehead | 0.21 | |
| | Female - Forearm | 0.12 | |
| | Male - Forearm | 0.11 | |
| Barel et al. | Female - Forearm | 0.16 | Suction |
| | Male - Forearm | 0.14 | |
| | Female - Forehead | 0.32 | |
| | Male - Forehead | 0.25 | |
| | Female - Temporal | 0.31 | |
| | Male - Temporal | 0.20 | |
| Sanders | Female - Forearm | 0.037 | Torsion |
| | Male - Forearm | 0.032 | |
| Levequ et al. | Female - Forearm | 1.2 | Torsion |
| | Male - Forearm | 4.3 | |
| This study | Female - Forearm | 3.41 | CMS |
| | Male - Forearm | 3.55 | |

Figure 16B:
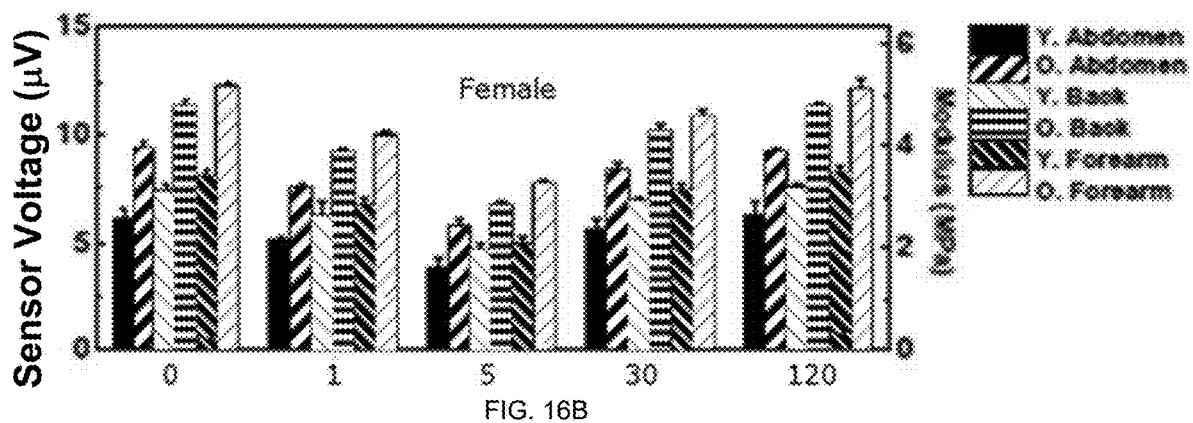
Figure 16C:
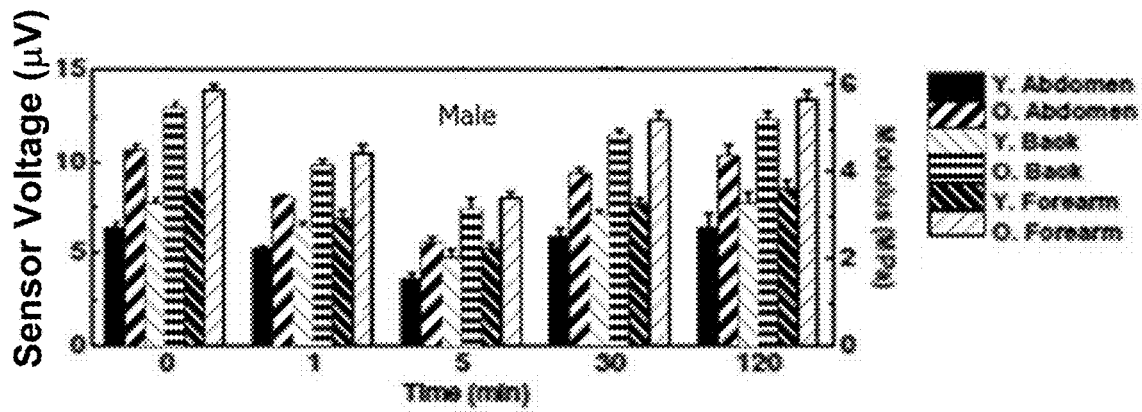
Figures 17A, 17B, 17C, 17D:
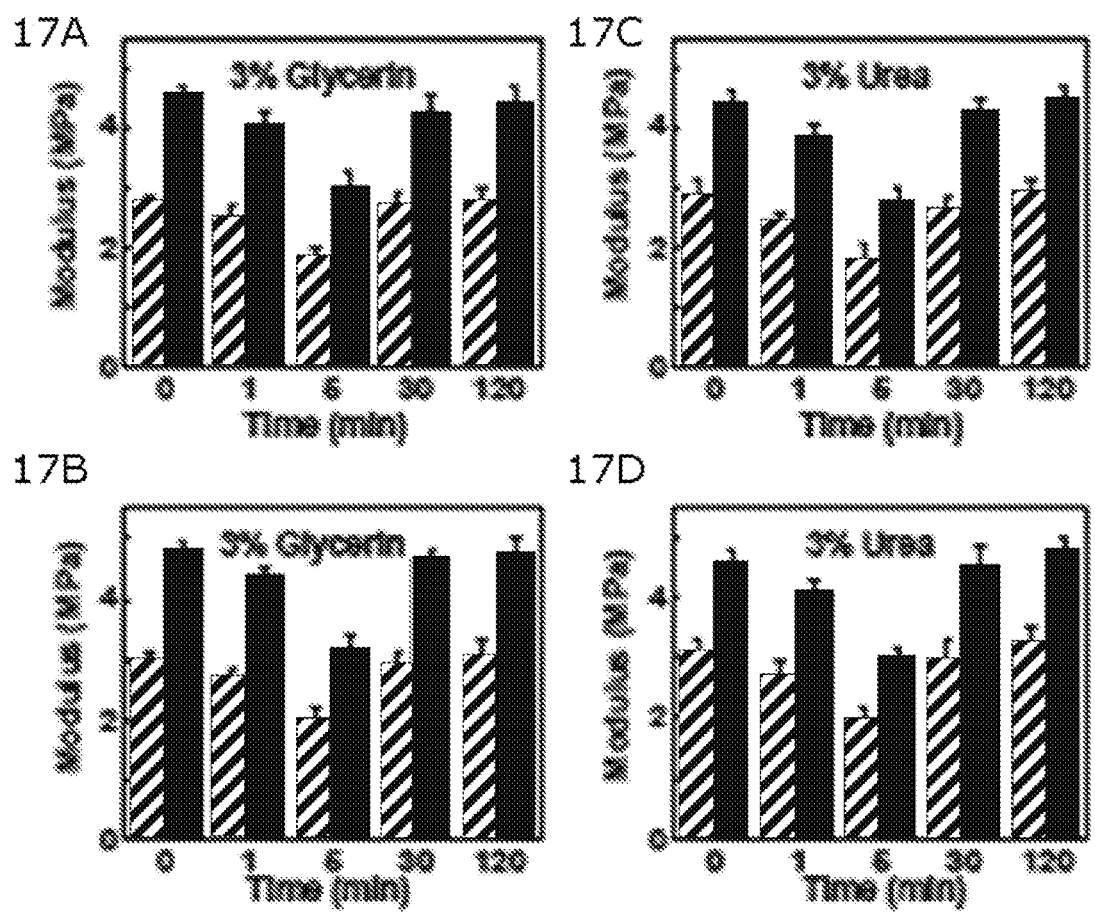
FIGS. 17A-17D depict the ex vivo evaluation of the modulus values of female and male abdominal skin before and at various time points after the application of 3% Glycerin and 3% Urea solution.
Figures 18A, 18B, 18C, 18D, 18E, 18F:
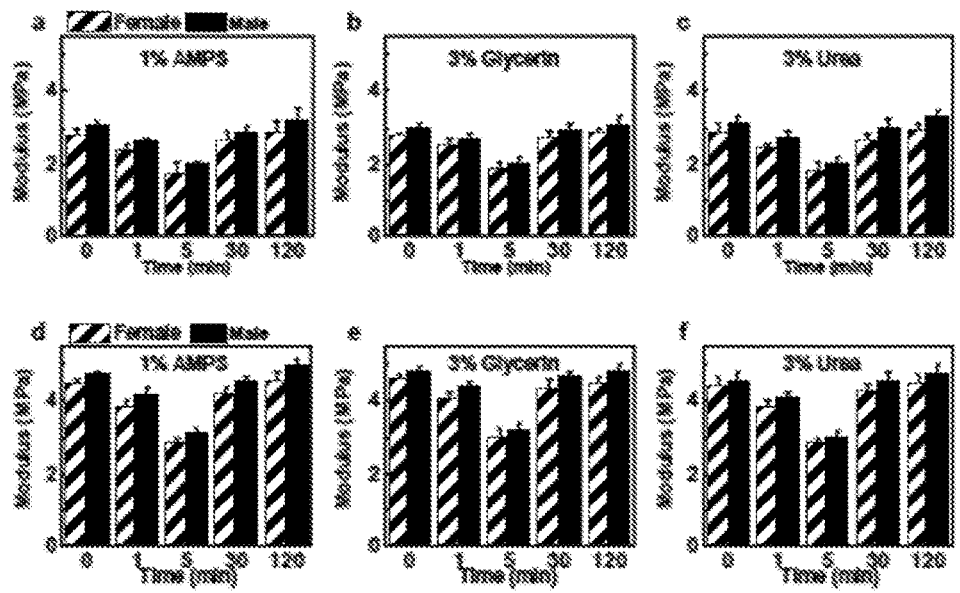
FIGS. 18A-18F depict ex vivo evaluation of the modulus values of female and male abdominal skin before and at various time points after the application of 1% AMPS, 3% Glycerin and 3% Urea solution.
Figure 19A:
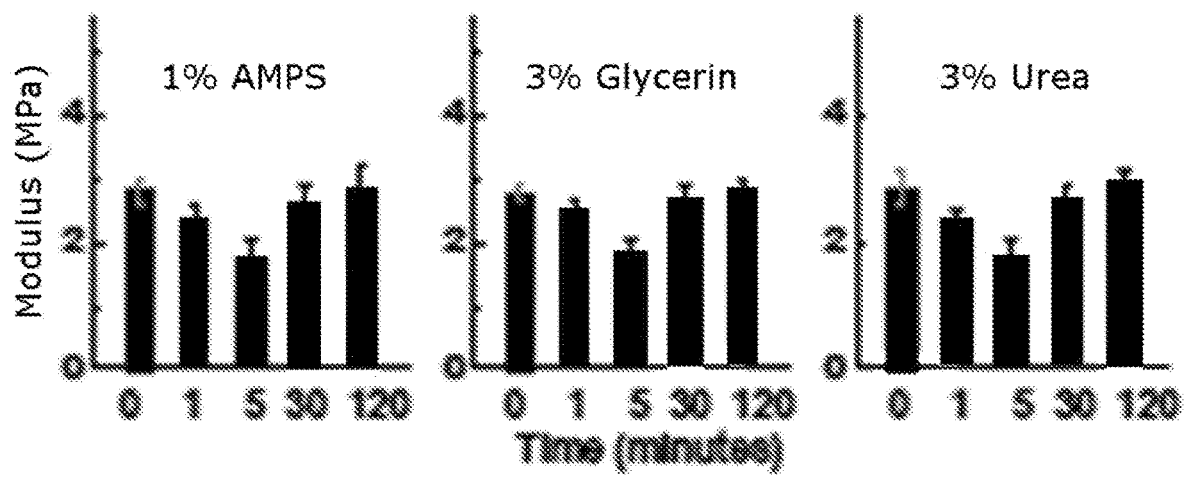
FIGS. 19A-19D depict ex vivo evaluation of the modulus values of female and male abdominal skin before and at various time points after the application of 1% AMPS, 3% Glycerin and 3% Urea solution.
Figure 19B:
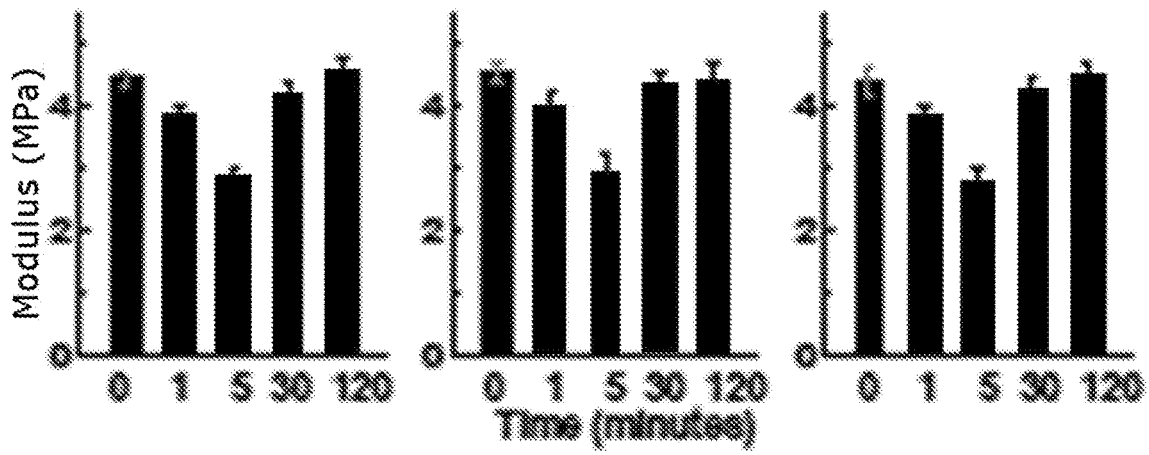
Figure 19C:
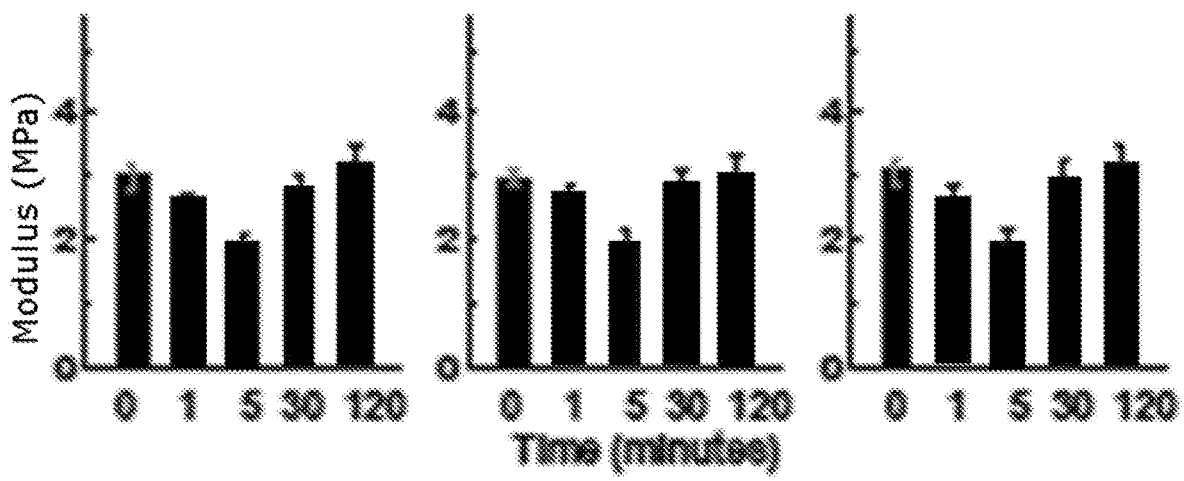
Figure 19D:
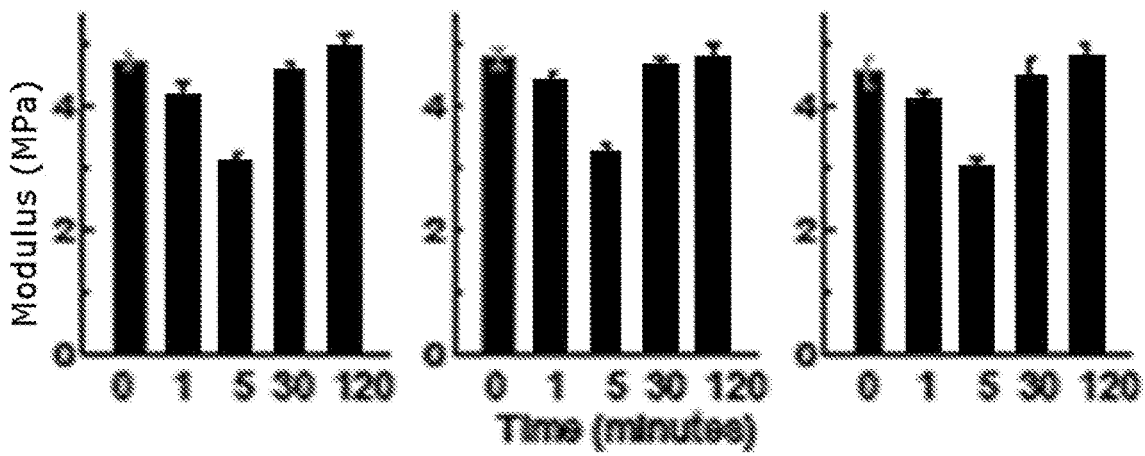

Moisturizing agents tend to improve and/or restore the intrinsic properties of skin by modifying the mechanical and tribological behaviors. The AMPS solution offers the hydrating effects of glycerol and the plasticizing effects of urea due to strong interactions between the skin and the protein components of the solution. The CMS data show that the plasticizing effect induces a temporary (~5 min) reduction of the Young's modulus, with a return to the initial state within ~2 hours, consistent with previous observations based on nanoindentation. Although the modulus varies with position across the body, the overall trends with application of AMPS are similar, as summarized for measurements in vivo on skin in FIGS. 16B and 16C. Visible laser confocal microscope images (Leica SP2) highlight the structural changes induced by moisturizers. Visible laser confocal microscope images, in angled and cross sectional views, of ex vivo young female abdominal skin before and after the application of 1%

AMPS revealed that the application of 1% AMPS causes an increase in the thickness of the ex-vivo abdominal skin (young female) by ~80%, qualitatively consistent with related studies. Skin from the old female, young male, and old male yield similar findings, as confirmed by the laser confocal microscope 3D images. The changes in fluorescence intensity revealed decreases in the density of collagen due to swelling of the skin from uptake of the moisturizing agent.

Figures 21A, 21B, 21C, 21D, 21E, 21F:
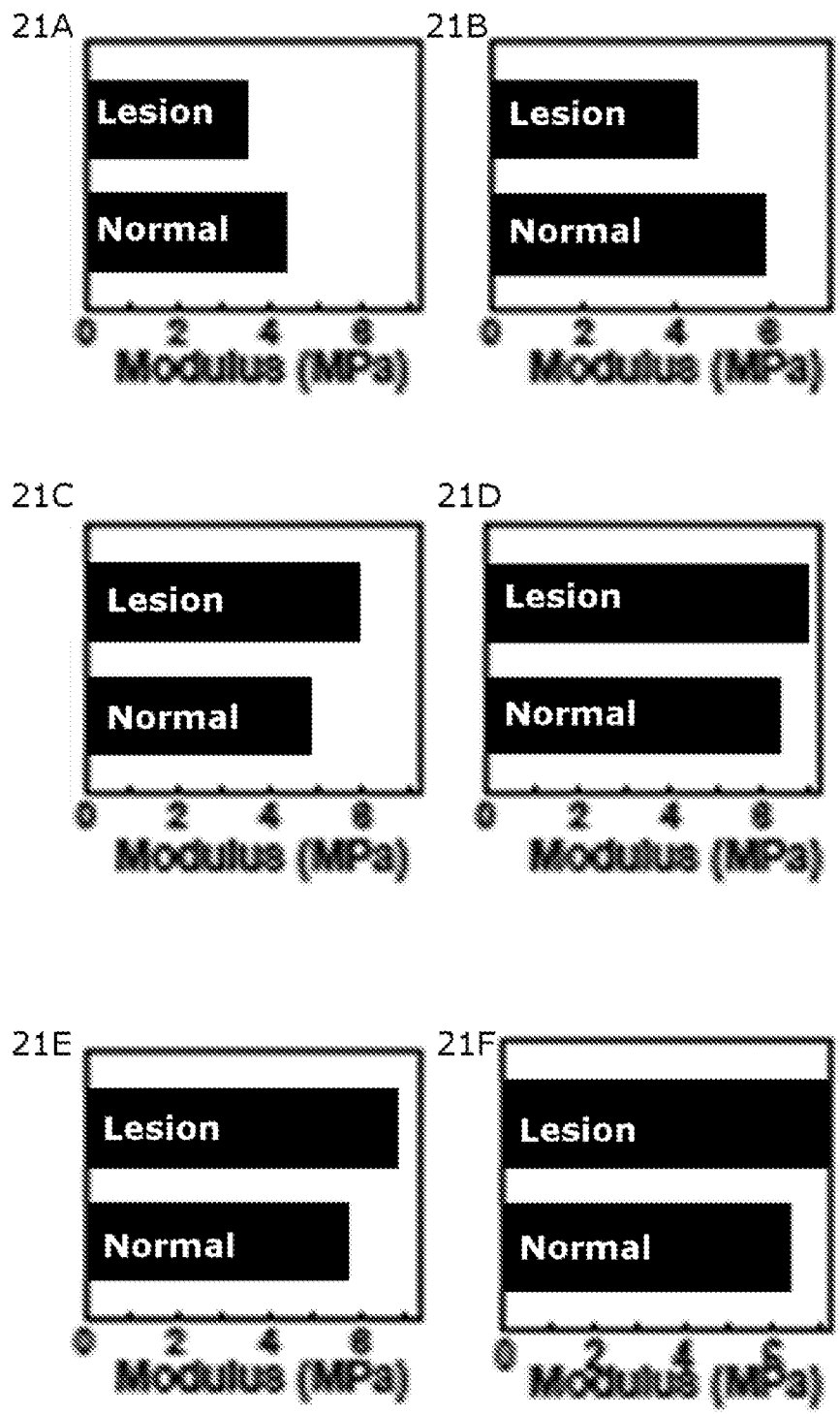
FIGS. 21A-21F depict the compliant modulus sensors mapping of pathologies located on various body regions.
Figures 22A, 22B, 22C, 22D:
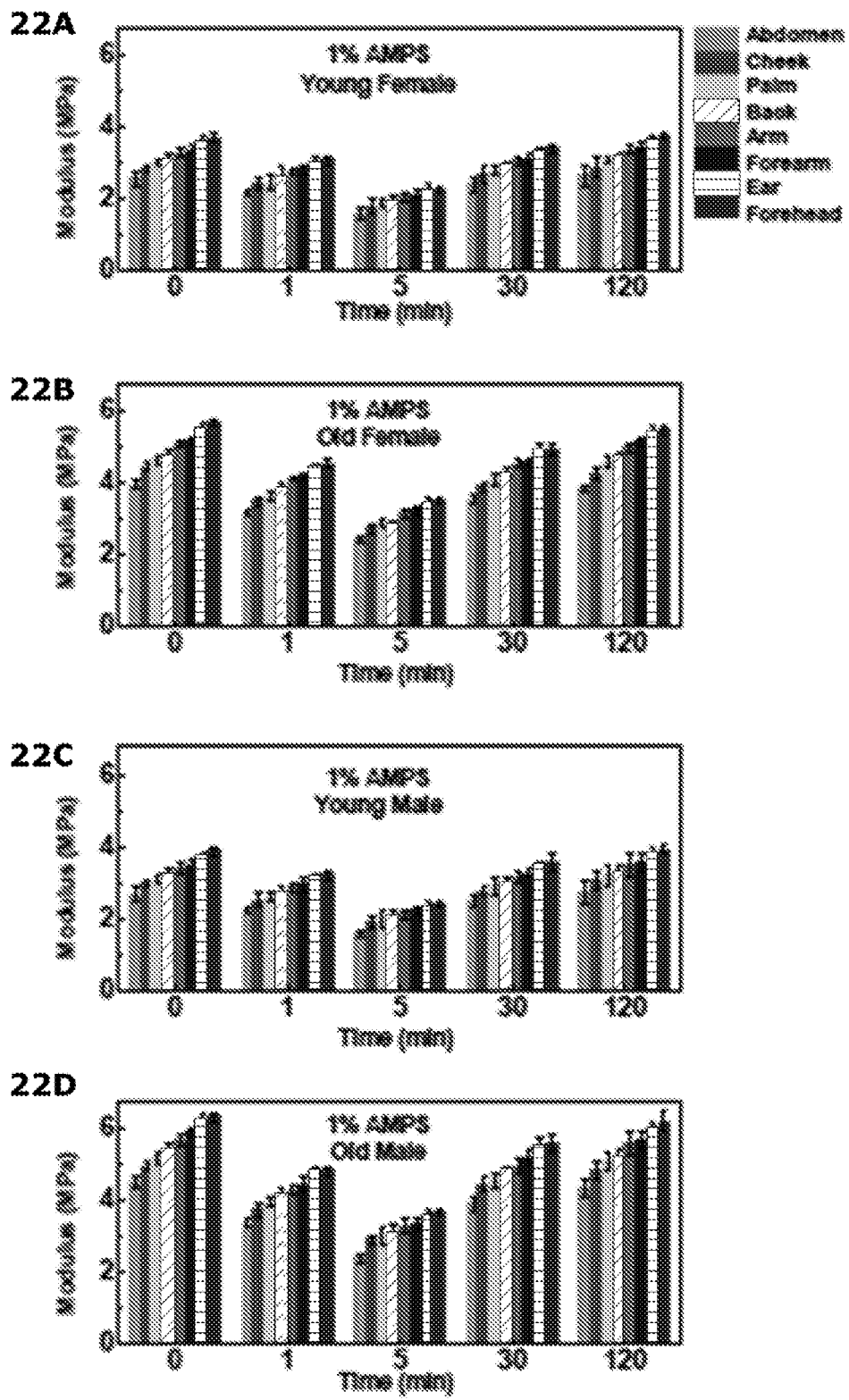
FIGS. 22A-22D depict in vivo evaluation of the modulus values of female and male skin before (0 min) and at various time points after the application of 1% AMPS solution.
Figures 23A, 23B, 23C, 23D:
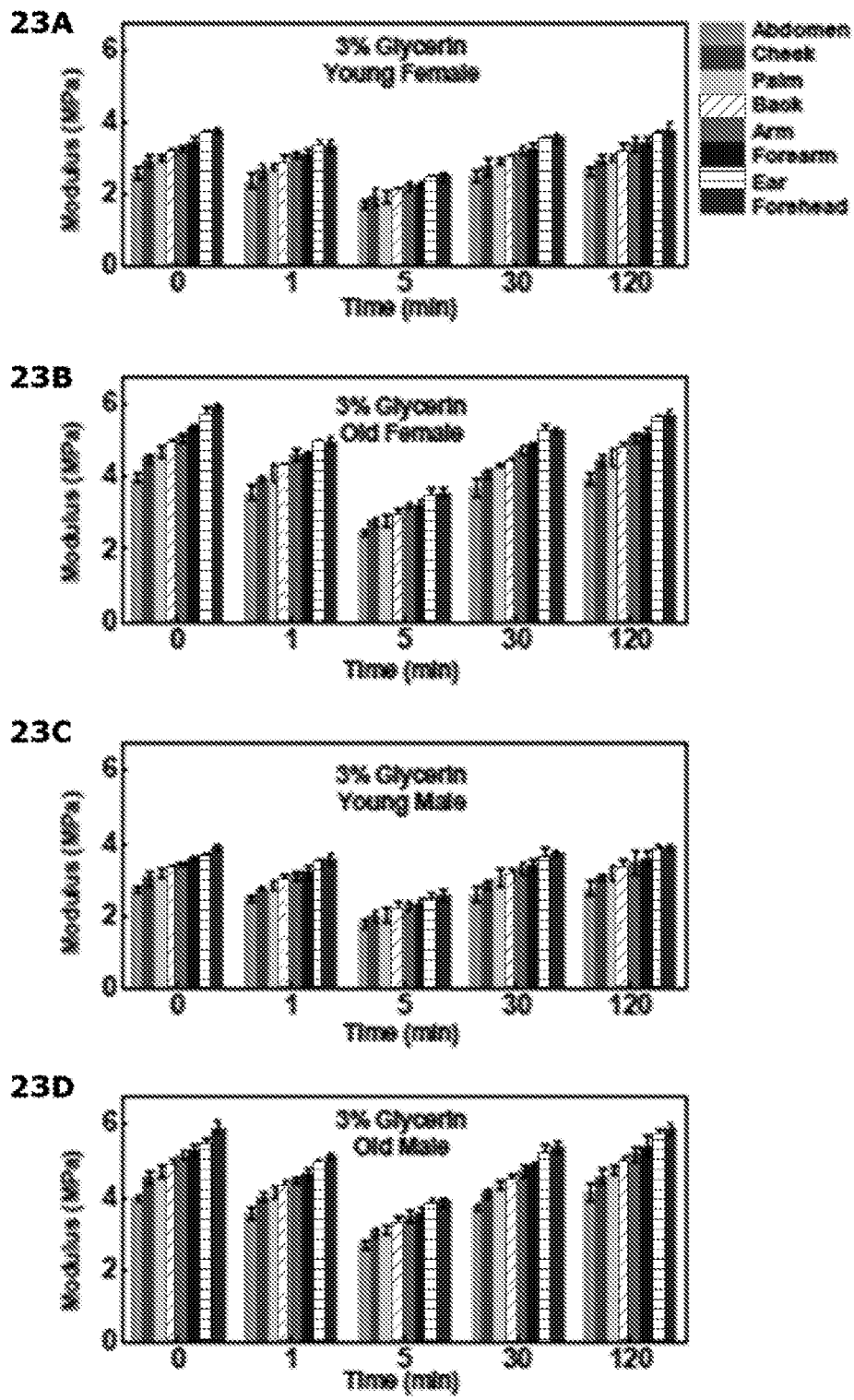
FIGS. 23A-23D depict in vivo evaluation of the modulus values of female and male skin before (0 min) and at various time points after the application of 3% Glycerin solution.
Figures 24A, 24B, 24C, 24D:
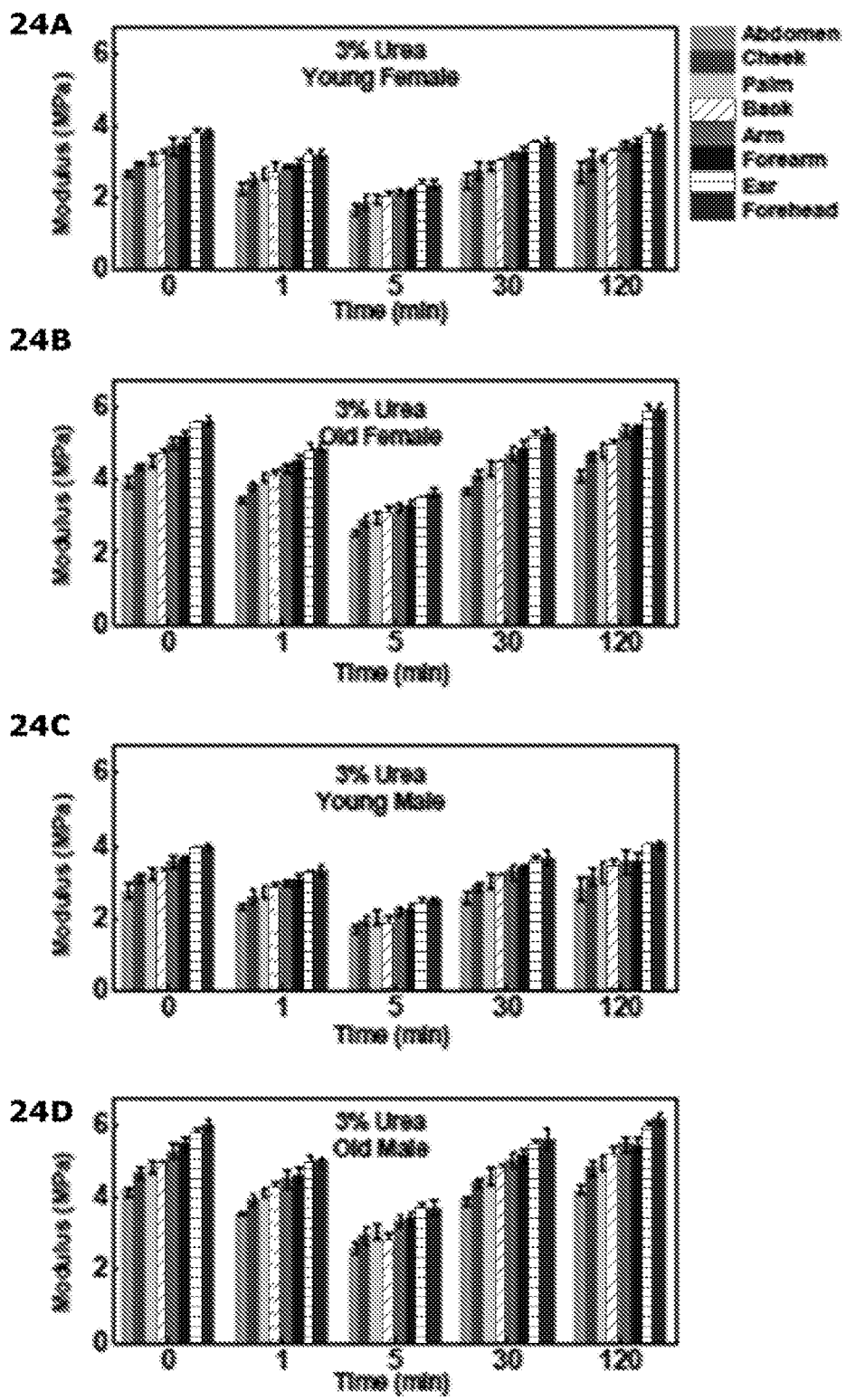
FIGS. 24A-24D depict in vivo evaluation of the modulus values of female and male skin before (0 min) and at various time points after the application of 3% Urea solution.
Figures 25A, 25B:
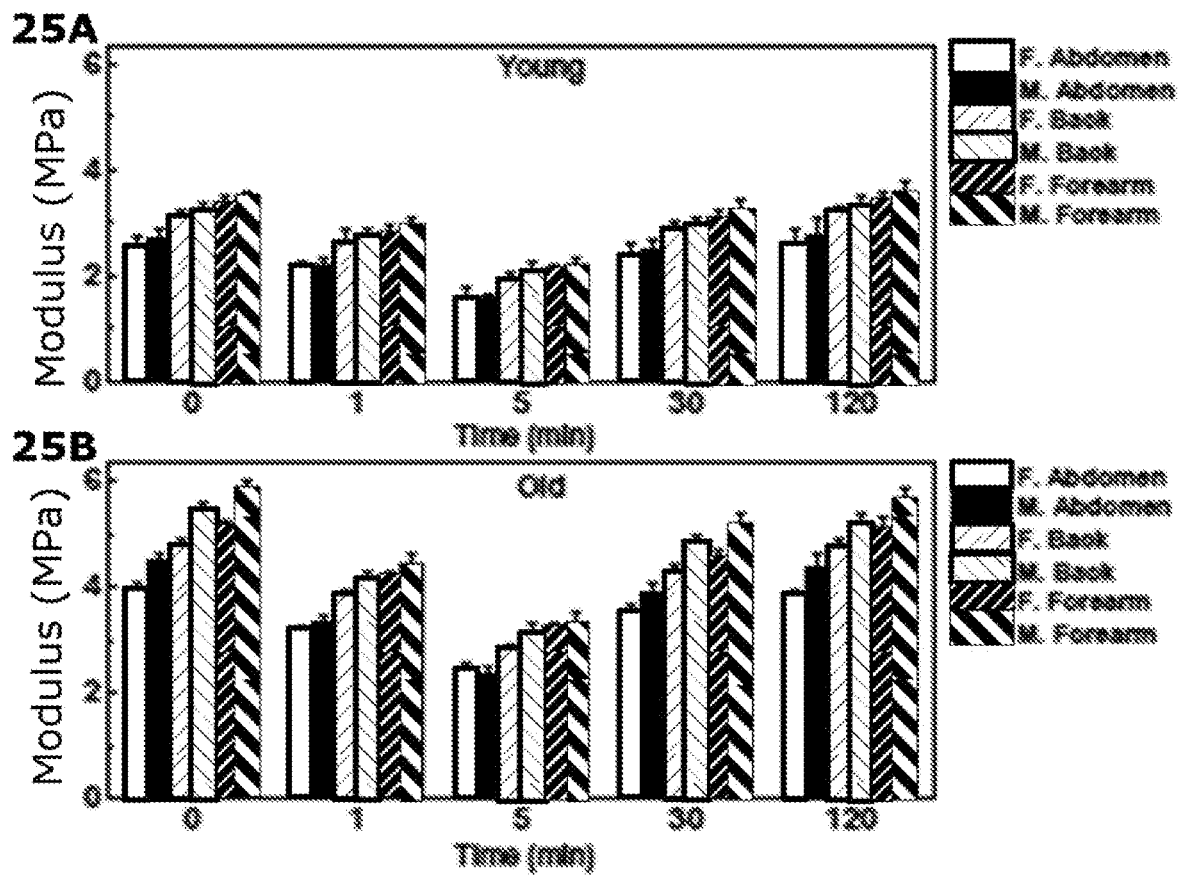
FIGS. 25A-25B depict in vivo evaluation of the modulus values of female and male skin before (0 min) and at various time points after the application of 3% AMPS solution. Three skin locations for female and male cases are shown: F. vs. M. Abdomen (Female vs. Male Abdomen), F. vs. M. Back (Female vs. Male Back), F. vs. M. Forearm (Female vs. Male Forearm).
Figure 27A:
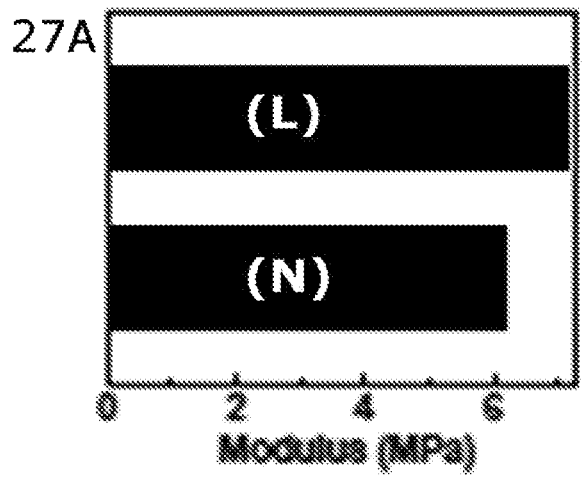
FIGS. 27A-27C are graphs of the modulus values obtained from lesion (L) and normal (N) skin near and at the locations of skin cancers on, from top to bottom, the nose, finger, and lip of a patient.
Figure 27B:
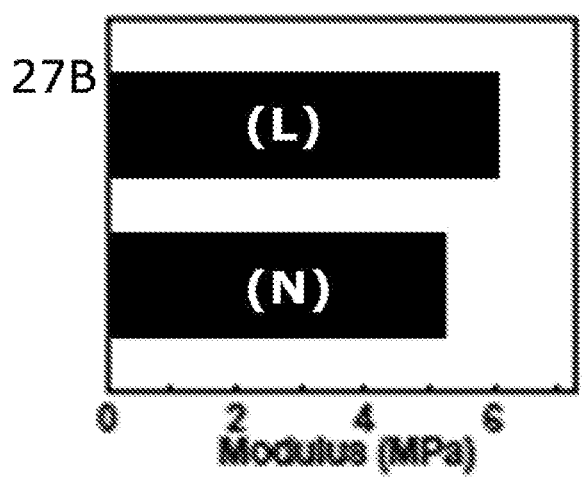
Figure 27C:
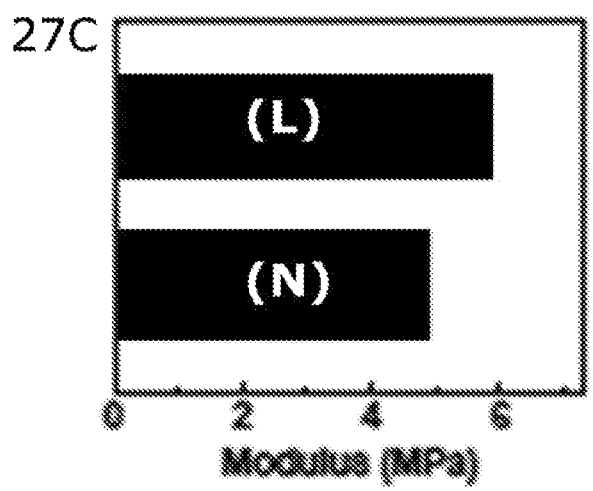

Moduli measured in-vivo show similar trends with age, gender and application of moisturizing solutions. Here, however, the skin has the correct balance of extracellular and intracellular fluid, with no insensible fluid loss, compared to ex-vivo. As a result, in-vivo tissues have lower moduli than those of well-maintained ex-vivo samples. As an example of an important in-vivo application, CMS measurements can reveal localized changes in skin properties near lesions sites on a cohort of patients. This mode of operation has value in clinical examination, where skin tumors are typically noted to be stiffer than healthy tissue and can frequently be detected through physical palpations with detectable differences in mass, stiffness and viscoelasticity. Such differences manifest as a result of physical and molecular mechanisms underlying tumor progression, and can be utilized as biomarkers to assess the metastatic potential of cancer cells. Results obtained from dermatologic malignancies in 30 patient volunteers indicate that skin lesions in the breast and leg regions have lower moduli than in their healthy skin counterparts (FIGS. 21A-21B); however, skin covering the nose and forehead regions have values higher than healthy skin counterparts (FIGS. 21C-21D). Such variability may be due to structural changes associated with frailty or skin thickness alterations as a result of aging. Nevertheless, the computed modulus values and output voltages for measurements at different locations of the body (See FIGS. 22A-22D, 23A-23D, and 24A-24D) provide a framework for mapping the stiffness of skin. Comparisons between young and old, for female and male, appear in 62. A summary of CMS performance on healthy and diseased skin is in FIGS. 5A-5E, 6A-6E, 7A-7D. Because the NMP lies near the middle of the PZT layers, bending induces only minor changes in device operation (FIGS. 15 and 26). As such, curved contours of the body such as the nose, finger, and upper lip may be readily wrapped for measurement (See FIGS. 27A-27C).

Figure 30:
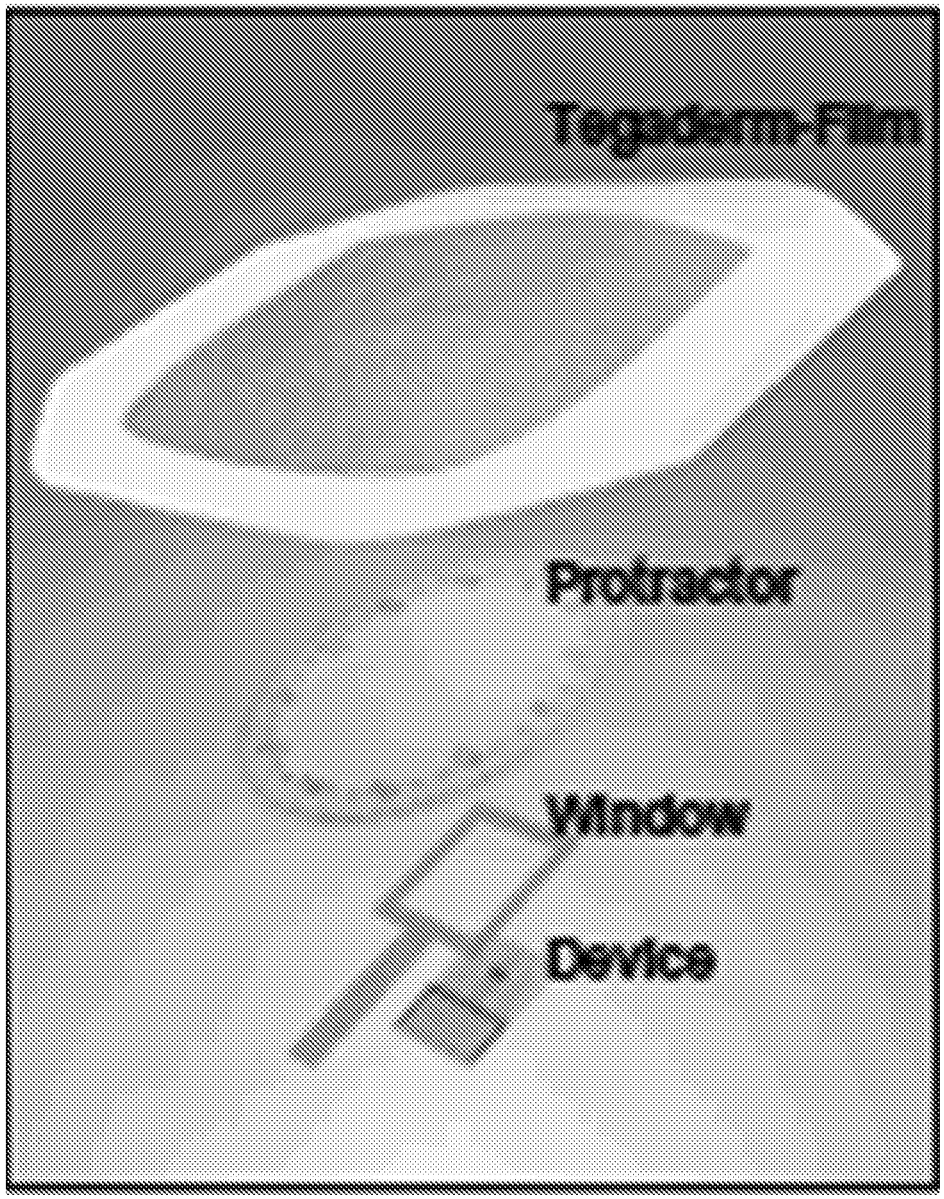
FIG. 30 is an exploded-view schematic illustration of a rotatable CMS system.

The devices can also provide directional and spatial mapping of regional stiffness differences, via measurement modes that exploit the reversibility of the soft contact between the CMS and the skin. The results described here used a protractor (~2 cm radius) printed on a transparent film (AF4300, 3M), with a rotatable segment (See FIG. 30). See Methods for details. Aligning the modulus sensor to the window element and loosely connecting it with a thread enables calibrated rotations in the clockwise and anticlockwise directions. Application of an adhesive film (3M Tegaderm™ Film) on top of the entire structure prevents movement during recording.

Figure 28A:
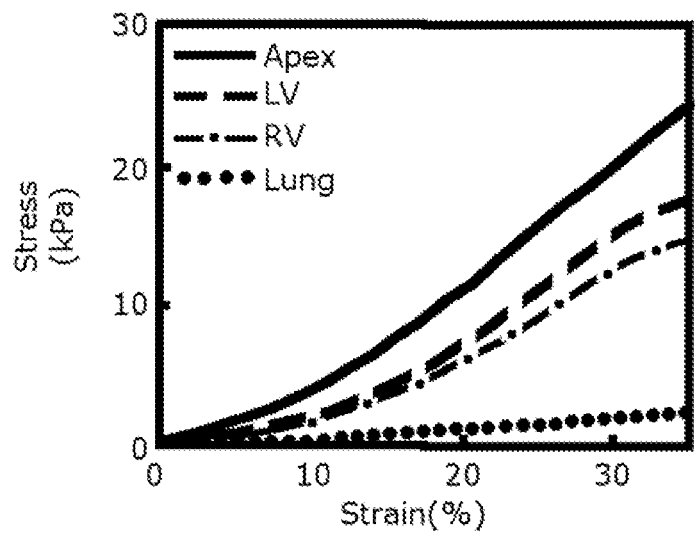
FIGS. 28A-28C depict ex vivo CMS measurements on bovine organs.
Figure 28B:
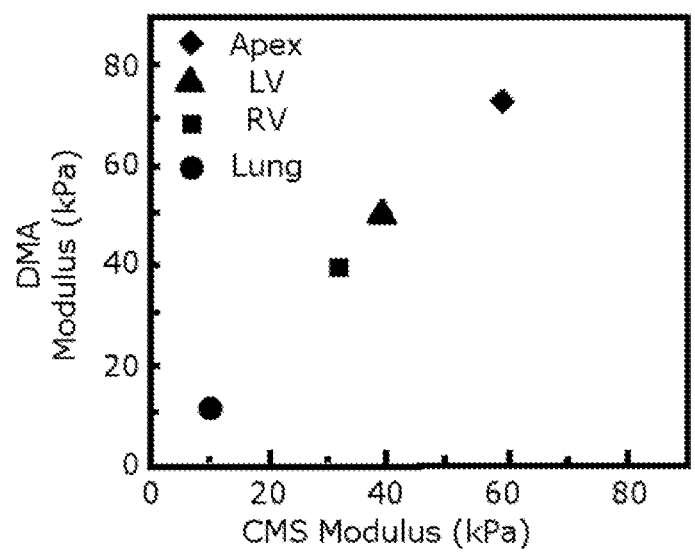
Figure 28C:
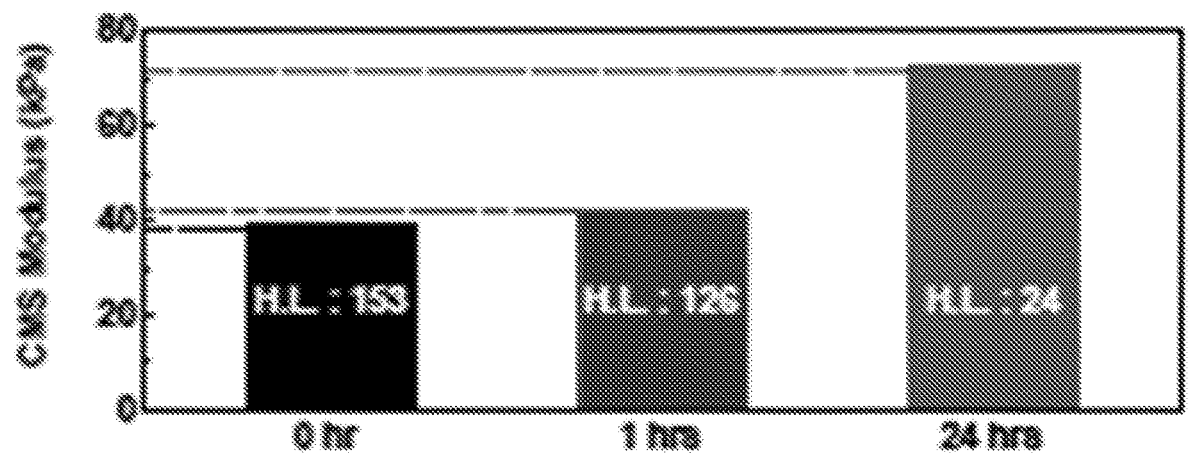

The same CMS platforms can be applied to biological tissues other than the skin. Measurements from the apex of bovine heart, as well as the left (LV) and right (RV) ventricle, and lung appear in FIGS. 28A-C. Stress-strain curves via DMA recorded from tissue samples ~2 h after explanation (FIG. 28A) establish an estimate of the modulus values for these samples. FIG. 28B compares these results to the CMS output voltages. The apex of the heart exhibits the highest modulus, as might be expected due to the crisscrossing and confluence of multiple cardiac muscle and fibrous bands in this region. The differences between moduli measured by DMA and CMS may arise from the absence of blood supply over the time required to prepare samples for DMA, which can lead to a relative dehydration state, i.e. a decrease of both intra- and extra-cellular fluid, resulting in slightly stiffer mechanical properties. This time dependence can be tracked explicitly, by use of a CMS, as in FIG. 28C. A commercial moisture meter (MoistureMeterSC Compact, Delfin Inc) establishes the change in the hydration level (H.L.) of the explanted LV contained in a scintillation vial with cap opened half of a turn, at room temperature (native state), 1 h, and 24 h after desiccation in a 60° C. dry incubator. The findings and observations demonstrate correlations between modulus, visible color and dehydration state.

The concepts in materials and characterization methods introduced here demonstrate rapid, "on patient" measurements and spatial mapping of mechanical properties of the skin and other vital organs. For dermatologic investigation, the protocols of measurement are non-invasive and rapid, affording a high level of patient acceptance as evidenced in this study by near complete enrollment of approached volunteers (i.e, 30/31, ~97%), and by specific comments made by enrollees on procedure comfort and acceptability. These in vivo clinical measurements, along with those on the various control samples and ex vivo organs yield moduli that lie within an accepted range, with trends in terms of body positions and responses to moisturizing agents that are compatible with expectation, including local intra-dermal stiffness changes which correlate with intra-tissue pathology that may not be readily visible to the naked eye.

A characteristic of the exemplary sensor is the capacity to provide soft, conformal, reversible contact with the curved, textured surfaces of targeted organs. Future embodiments could incorporate high-density arrays of sensors to increase the sensitivity of focal stiffness resolution, to realize capabilities in rapidly accessible spatial resolution which could easily exceed those achievable by human touch on physical exam. Such a development would represent a significant advance as a diagnostic tool, enhancing the sensitivity of office and hospital based dermatologic screening and examination. Further, similar systems may be fashioned to measure mechanical property changes over time for clinical monitoring of a wide range of conditions, where variations are anticipated either due to alterations in pathophysiology over time or due to a response to therapy. The ability to deploy this measurement technology for internal organs of the body through catheters, trochars or endoscopes represents additional areas of opportunity. As such devices may be deployed to the ectoluminal, endoluminal or endomural surface or region for their use.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

We claim:

1. A device for contact sensing of a material property comprising:
   a thin elastomeric substrate,
   an actuating element, and a sensing element mechanically coupled to the actuating element, where the sensing element is interdigitated within the actuating element; and wherein the sensing element has an output voltage that varies linearly with an input voltage of the actuating element over a range of input voltages and a range of values for the material property.

2. The device of claim 1, wherein the sensing element is substantially aligned with the actuating element.

3. The device of claim 1, wherein the sensing element and the actuating element are separated by less than 1.0 mm.

4. The device of claim 1, further comprising a first pair of electrodes in electrical contact with the actuating element and a second pair of electrodes in electrical contact with the sensing element.

5. The device of claim 4, wherein the first pair of electrodes are in electrical contact with the actuating element via stretchable conductive interconnects, the second pair of electrodes are in electrical contact with the sensing element via stretchable conductive interconnects, or both.

6. The device of claim 1, wherein the actuating element, the sensing element, or both comprise a piezoelectric material.

7. The device of claim 6, further comprising a neutral mechanical plane passing through the piezoelectric material.

8. The device of claim 1, wherein the device comprises a plurality of the actuating elements and a plurality of the sensing elements and each of the sensing elements is mechanically coupled to one or more of the actuating elements.

9. The device of claim 8, wherein the sensing elements are interdigitated within the actuating elements.

10. The device of claim 1, wherein the sensing element has an output that is linearly proportional to the material property over a range of values.

11. The device of claim 10, wherein the sensing element is capable of producing a detectable change in the output in response to a change of at least 1% in the material property.

12. The device of claim 1, wherein the device is configured to bond to a surface of a material having a surface roughness extending over a range of roughness from 0.1 to 100 µm, and the sensing element has an output voltage that is independent of the surface roughness of the material.

13. The device of claim 10, wherein the device is configured to:
receive the output from the sensing element in response to activation of the actuating element;
determine the material property of a material based upon the output; and
initiate a response to the output.

14. A method of making the device of claim 1, comprising:
forming a top electrode by photolithography with an electrode material selected from the group consisting of Ag, Al, Au, Co, Cr, Cu, Fe, Mo, Nb, Ni, W, Zn, Zr, Ti, Pt, and combinations thereof;
deposition, patterning, or etching of a piezolelectric layer with a piezoelectric material selected from the group consisting of Berlinite (AlPO4), Sucrose (table sugar), Quartz, Rochelle salt, Topaz, Tourmaline-group minerals, Gallium orthophosphate ($GaPO_4$), Langasite ($La_3Ga_5SiOi_4$), Barium titanate ($BaTiO_3$), Lead titanate ($PbTiO_3$), Lead zirconate titanate ($Pb[Zr_xTii\char`\^]O_3$, $0<x<1$), Potassium niobate ($KNbO_3$), Lithium niobate ($LiNbO_3$), Lithium tantalate ($LiTaO_3$), Sodium tungstate ($Na2WO_3$), Zinc oxide (ZnO), $Ba_2NaNb_5O5$, $Pb_2KNb_5Oi_5$, Sodium potassium niobate ($(K,Na)NbO_3$) (NKN), Bismuth ferrite ($BiFeO_3$), Sodium niobate ($NaNbO_3$), Bismuth titanate (BUT$\char`\^$On), Sodium bismuth titanate ($Nao.sBio.5TiO_3$), polyvinylidene fluoride (PVDF), poly [(vinylidenefluoride-co-trifluoroethylene] [P(VDF-TrFE)3, and combinations thereof;

deposition, patterning, or etching of a bottom electrode with an electrode material selected from the group consisting of Ag, Al, Au, Co, Cr, Cu, Fe, Mo, Nb, Ni, W, Zn, Zr, Ti, Pt, and combinations thereof.

15. The method of claim 14, further comprising transferring the actuating element and the sensing element to the thin elastomeric substrate.

16. The method of claim 14, further comprising encapsulating one or both of the actuating element and the sensing element with a barrier layer.

17. A method of contact sensing of a material property comprising:
applying a device for contact sensing a material property to a surface of skin, wherein the device comprises a thin elastomeric substrate, an actuating element, and a sensing element mechanically coupled to the actuating element;
activating the actuating element to manipulate a material; and
receiving an output from the sensing element in response to the manipulation of the material, wherein the output is associated with the material property and the material property is indicative of a physiological state selected from the group consisting of a hydration level of the skin, a healing progress of the skin, and a disease state of the skin.

18. The method of claim 17, wherein the device binds to a surface of the material by van der Waals interactions.

19. The method of claim 17, further comprising removing the device from a surface of the material and reapplying the device to the same surface or to a second material surface.

20. The method of claim 17, further comprising:
determining one or more material properties of the material based upon the output of the sensing element, and
initiating a function in response to the one or more properties.

21. The method of claim 17, wherein the material is an organ and the material property is indicative of a physiological state selected from the group consisting of a hydration level of the organ, a healing progress of the organ, and a disease state of the organ.

\* \* \* \* \*